US009743899B2

(12) United States Patent
Moon et al.

(10) Patent No.: US 9,743,899 B2
(45) Date of Patent: Aug. 29, 2017

(54) METHOD OF DISPLAYING VIRTUAL RULER ON SEPARATE IMAGE OR MEDICAL IMAGE OF OBJECT, MEDICAL IMAGE OBTAINING APPARATUS, AND METHOD AND APPARATUS FOR DISPLAYING SEPARATE IMAGE OR MEDICAL IMAGE WITH VIRTUAL RULER

(71) Applicant: SAMSUNG ELECTRONICS CO., LTD., Gyeonggi-do (KR)

(72) Inventors: Hee-yeon Moon, Suwon-Si (KR); Seung-hoon Shin, Seoul (KR); Woo-sup Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 96 days.

(21) Appl. No.: 14/813,843

(22) Filed: Jul. 30, 2015

(65) Prior Publication Data
US 2015/0335305 A1 Nov. 26, 2015

Related U.S. Application Data

(63) Continuation-in-part of application No. 14/611,744, filed on Feb. 2, 2015, which is a continuation of
(Continued)

(30) Foreign Application Priority Data

Sep. 7, 2012 (KR) .................. 10-2012-0099547
Mar. 13, 2013 (KR) .................. 10-2013-0026812

(51) Int. Cl.
*G01T 7/00* (2006.01)
*A61B 6/00* (2006.01)
(Continued)

(52) U.S. Cl.
CPC .......... *A61B 6/5294* (2013.01); *A61B 5/1075* (2013.01); *A61B 5/743* (2013.01);
(Continued)

(58) Field of Classification Search
CPC G01N 2223/427; A61B 5/1075; A61B 5/743; G06T 2207/10116; G06T 2207/20212; G06T 2207/30004
See application file for complete search history.

(56) References Cited

U.S. PATENT DOCUMENTS 6,097,833 A 8/2000 Lobregt et al.
6,151,521 A 11/2000 Guo et al.
(Continued)

FOREIGN PATENT DOCUMENTS

CN 101004834 A 7/2007
DE 102009021311 A1 11/2010
(Continued)

OTHER PUBLICATIONS

Andre Goossen et al., "A Stitching Algorithm for Automatic Registration of Digital Radiographs", Image Analysis and Recognition (Lecture Notes in Computer Science), Jun. 25, 2008, pp. 854 to 862, XP019091347.
(Continued)

*Primary Examiner* — Hoon Song
(74) *Attorney, Agent, or Firm* — Sughrue Mion, PLLC

(57) ABSTRACT

A medical image obtaining apparatus includes: an image obtainer, which comprises an X-ray emitter configured to emit X-rays toward an object and an X-ray detector configured to detect X-rays that have penetrated the object, and is configured to obtain an image of a portion of the object based on the detected X-rays; a controller configured to generate a virtual ruler which indicates information about a location of the image, based on a rotation angle of the X-ray
(Continued)

emitter; and a display configured to display the virtual ruler on the image.

31 Claims, 27 Drawing Sheets

Related U.S. Application Data application No. 13/949,763, filed on Jul. 24, 2013, now Pat. No. 8,977,028.

(51) Int. Cl.
| | |
|---|---|
| *G06T 7/00* | (2017.01) |
| *A61B 5/00* | (2006.01) |
| *A61B 5/107* | (2006.01) |
| *G06T 11/20* | (2006.01) |
| *G06T 11/60* | (2006.01) |

(52) U.S. Cl.
CPC ............ *A61B 6/461* (2013.01); *A61B 6/463* (2013.01); *A61B 6/5241* (2013.01); *G06T 7/0012* (2013.01); *G06T 11/206* (2013.01); *G06T 11/60* (2013.01); *G06T 2207/10116* (2013.01); *G06T 2207/20212* (2013.01); *G06T 2207/30004* (2013.01)

(56) References Cited

U.S. PATENT DOCUMENTS

| | | | |
|---|---|---|---|
| 6,512,892 | B1 | 1/2003 | Montgomery et al. |
| 6,929,607 | B2 | 8/2005 | Lipman |
| 7,458,977 | B2 | 12/2008 | McGinley et al. |
| 8,319,952 | B2 | 11/2012 | Otani et al. |
| 8,396,269 | B2 | 3/2013 | Henderson et al. |
| 8,896,621 | B1 | 11/2014 | Sipher et al. |
| 2004/0101103 | A1 | 5/2004 | Warp et al. |
| 2004/0153062 | A1 | 8/2004 | McGinley et al. |
| 2005/0128291 | A1 | 6/2005 | Murakami |
| 2005/0128297 | A1 | 6/2005 | Katsuyama |
| 2005/0128465 | A1 | 6/2005 | Skultety-Betz et al. |
| 2005/0251021 | A1 | 11/2005 | Kaufman et al. |
| 2006/0008779 | A1 | 1/2006 | Shand et al. |
| 2007/0038073 | A1 | 2/2007 | Mistretta |
| 2008/0124064 | A1 | 5/2008 | Klinghult et al. |
| 2008/0146277 | A1 | 6/2008 | Anglin et al. |
| 2009/0100368 | A1 | 4/2009 | Look et al. |
| 2009/0118600 | A1 | 5/2009 | Ortiz et al. |
| 2009/0190808 | A1 | 7/2009 | Claus |
| 2010/0014780 | A1 | 1/2010 | Kalayeh |
| 2010/0056128 | A1 | 3/2010 | Hwang et al. |
| 2010/0246923 | A1 | 9/2010 | Nathaniel et al. |
| 2010/0295796 | A1 | 11/2010 | Roberts et al. |
| 2011/0043515 | A1 | 2/2011 | Stathis |
| 2011/0109650 | A1 | 5/2011 | Kreeger et al. |
| 2011/0149041 | A1 | 6/2011 | Eccles et al. |
| 2011/0169748 | A1 | 7/2011 | Tse et al. |
| 2011/0175821 | A1 | 7/2011 | King |
| 2011/0188726 | A1 | 8/2011 | Nathaniel et al. |
| 2011/0243402 | A1 | 10/2011 | Kadir |
| 2012/0005624 | A1 | 1/2012 | Vesely |
| 2012/0050543 | A1 | 3/2012 | Colla et al. |
| 2013/0016126 | A1 | 1/2013 | Wang et al. |
| 2013/0114790 | A1* | 5/2013 | Fabrizio ............... A61B 6/02 378/62 |
| 2013/0215116 | A1 | 8/2013 | Siddique et al. |
| 2014/0366057 | A1 | 12/2014 | Brockmann et al. |

FOREIGN PATENT DOCUMENTS

| | | |
|---|---|---|
| EP | 2 037 294 A2 | 3/2009 |
| JP | 2001268595 A | 9/2001 |

OTHER PUBLICATIONS

Communication dated Nov. 25, 2013, issued by the European Patent Office in counterpart European Application No. 13182807.1.
Final Office Action received in parent U.S. Appl. No. 13/949,763 issued May 22, 2014.
International Search Report dated Oct. 16, 2013, issued by the International Searching Authority in counterpart International Application No. PCT/KR2013/006548.
Notice of Allowance received in parent U.S. Appl. No. 13/949,763 issued Oct. 28, 2014.
Office Action received in parent U.S. Appl. No. 13/949,763 issued Oct. 18, 2013.
Written Opinion dated Oct. 16, 2013, issued by the International Searching Authority in counterpart International Application No. PCT/KR2013/006548.
Non-Final Office Action received in parent U.S. Appl. No. 13/949,763 issued Mar. 13, 2015.
Communication dated Dec. 29, 2015, issued by the Korean Intellectual Property Office in counterpart Korean Application No. 10-2013-0026812.
USPTO Office Action dated Dec. 16, 2016 issued in co-pending U.S. Appl. No. 14/611,744.
USPTO Office Action dated Jul. 11, 2016 issued in co-pending U.S. Appl. No. 14/611,744.
USPTO Office Action dated Feb. 11, 2016 issued in co-pending U.S. Appl. No. 14/611,744.
USPTO Office Action dated Sep. 17, 2015 issued in co-pending U.S. Appl. No. 14/611,744.
USPTO Office Action dated Mar. 13, 2015 issued in co-pending U.S. Appl. No. 14/611,744.
Communication dated Jan. 20, 2017, issued by the European Patent Office in counterpart European Application No. 15170520.9.
Communication dated Feb. 24, 2017, issued by the State Intellectual Property Office of P.R. China in counterpart Chinese Application No. 201310404267.2.

\* cited by examiner

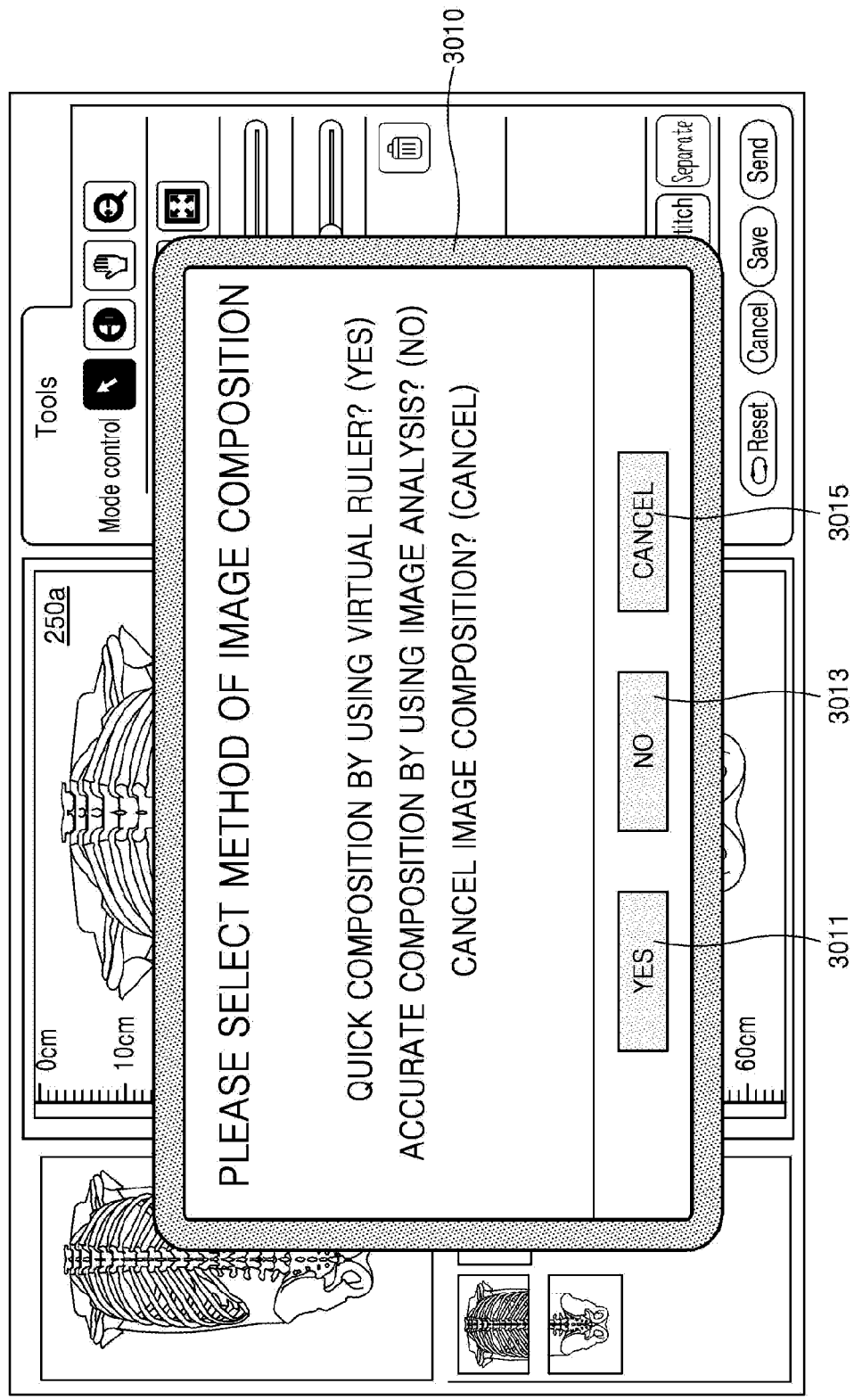

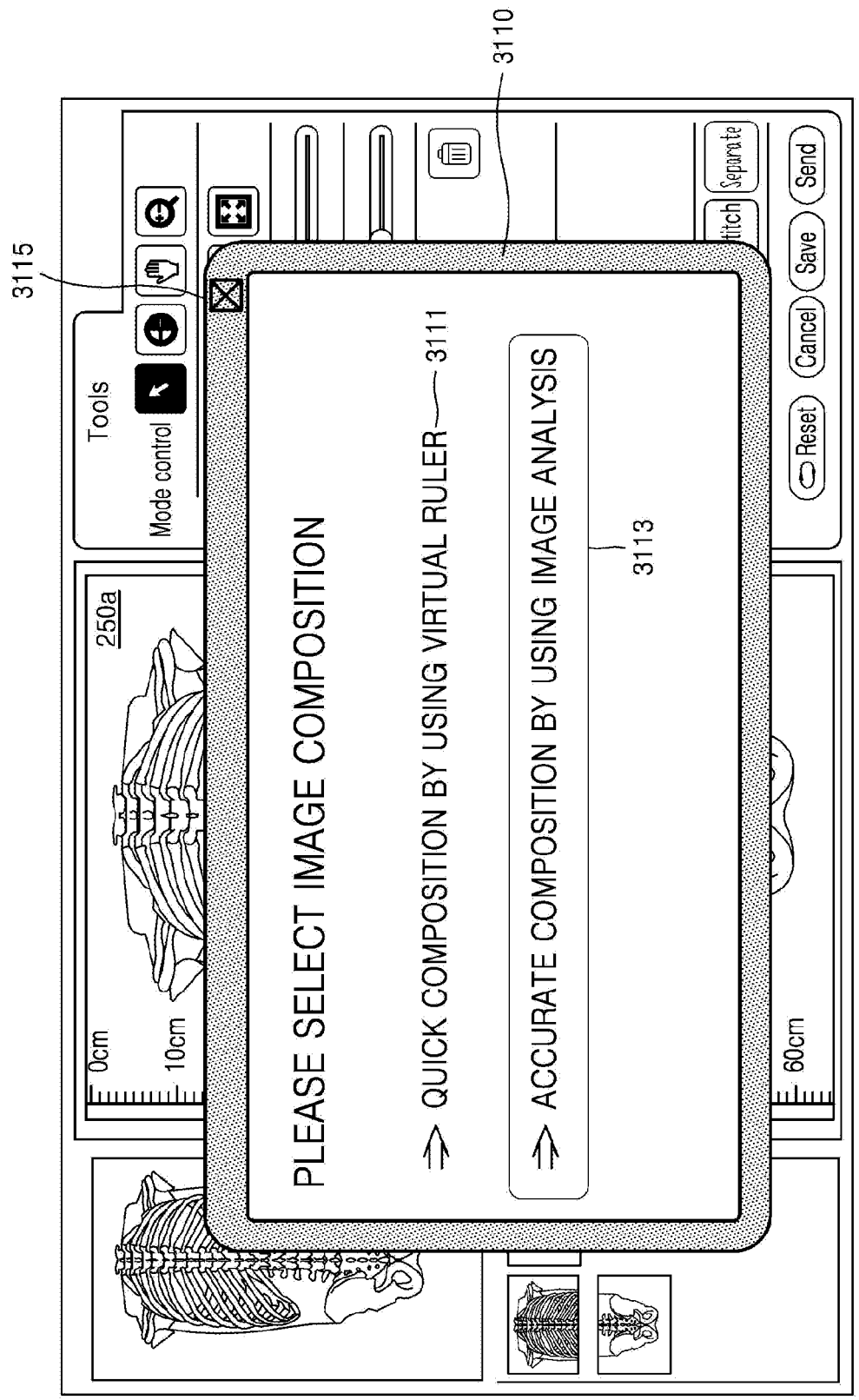

METHOD OF DISPLAYING VIRTUAL RULER ON SEPARATE IMAGE OR MEDICAL IMAGE OF OBJECT, MEDICAL IMAGE OBTAINING APPARATUS, AND METHOD AND APPARATUS FOR DISPLAYING SEPARATE IMAGE OR MEDICAL IMAGE WITH VIRTUAL RULER

CROSS-REFERENCE TO RELATED PATENT APPLICATIONS

This application is a continuation-in-part application of U.S. application Ser. No. 14/611,744, filed Feb. 2, 2015, which is a continuation application of U.S. application Ser. No. 13/949,763 filed Jul. 24, 2013, which claims priority from Korean Patent Application No. 10-2012-0099547, filed Sep. 7, 2012, and Korean Patent Application No. 10-2013-0026812, filed Mar. 13, 2013, in the Korean Intellectual Property Office, the disclosures of which are incorporated herein in their entireties by reference.

BACKGROUND

1. Field

Apparatuses and methods consistent with exemplary embodiments relate to displaying a virtual ruler on a separate image or medical image of an object.

2. Description of the Related Art

A magnetic resonance imaging (MRI) apparatus, a computed tomography (CT) apparatus, and an X-ray apparatus are used to obtain medical images of a body of a patient. Due to the resolution of images or the sizes of the above-mentioned apparatuses, an image of the entire body of the patient cannot be imaged at once and may be obtained as a composite image by imaging each of portions of the body and then composing captured images.

The medical image obtaining apparatus may provide a function of automatically composing separate images of a body, but the composition of the separate images may be performed inaccurately. For better accuracy, a method of indicating a ruler in each of separate images has been proposed in order to allow a user to manually combine separate images. However, there is a need for a method of efficiently, accurately, and conveniently indicating a ruler in each of separate images to allow a user to more accurately and accurately combine the separate images into a single image.

SUMMARY

Exemplary embodiments address at least the above problems and/or disadvantages and other advantages not described above. Also, an exemplary embodiment is not required to overcome the disadvantages described above, and an exemplary embodiment may not overcome any of the problems described above.

One or more exemplary embodiments provide a method of displaying a virtual ruler on a separate image or medical image of an object, by displaying the virtual ruler on each of the plurality of separate images without imaging the object together with a lead ruler when capturing the plurality of separate images of the object to generate a composite image of the object.

According to an aspect of an exemplary embodiment, there is provided a method of displaying a virtual ruler on each of a plurality of separate images of an object to generate a composite image, the method including: dividing the object into a plurality of imaging areas in a predetermined direction and obtaining a plurality of separate images corresponding to the plurality of imaging areas; obtaining a first distance of a separate image, which is a distance from a predetermined reference point to a first side of each of the plurality of separate images, and a second distance of the separate image, which is a distance from the predetermined reference point to a second side of each of the plurality of separate images; and displaying a virtual ruler, which indicates distance values between the obtained first distance of the separate image and the obtained second distance of the separate image, on each of the plurality of separate images.

The method of displaying a virtual ruler on each of a plurality of separate images of an object may be performed by an X-ray apparatus.

The obtaining of the plurality of separate images of the object may include obtaining the plurality of separate images at locations corresponding to the plurality of imaging areas by using an image obtainer that obtains X-ray images by using X-rays penetrating the object.

The obtaining of the first distance of the separate image and the second distance of the separate image may include obtaining, at locations corresponding to the plurality of imaging areas, a distance from the predetermined reference point to a first side of the image obtainer as the first distance of the separate image and a distance from the predetermined reference point to a second side of the image obtainer as the second distance of the separate image.

The displaying of the virtual ruler on each of the plurality of separate images may include: obtaining an actual distance of each pixel of the separate image by using a difference value between the first distance of the separate image and the second distance of the separate image and the number of pixels in a predetermined direction of the separate image; and displaying the virtual ruler on each of the plurality of separate images by using the first distance and the actual distance of each pixel, or the second distance and the actual distance of each pixel.

The displaying of the virtual ruler on each of the plurality of separate images may include: dividing the separate image into a plurality of areas in the predetermined direction; and displaying the virtual ruler on each of the plurality of separate images by using the first distance and a value, which is obtained by dividing a difference value between the first distance of the separate image and the second distance of the separate image by the number of the plurality of areas, or the second distance and the value, which is obtained by dividing a difference value between the first distance of the separate image and the second distance of the separate image by the number of the plurality of areas.

The predetermined direction may include a vertical direction of the object, the first side of each of the obtained plurality of separate images may include an upper side of each of the obtained plurality of separate images, and the second side of each of the obtained plurality of separate images may include a lower side of each of the obtained plurality of separate images.

The method of displaying a virtual ruler on each of a plurality of separate images of an object may further include displaying the plurality of separate images on each of which the virtual ruler is displayed; and when at least one separate image of the displayed plurality of separate images is moved horizontally, not moving at least one virtual ruler displayed on the at least one separate image or simultaneously moving a plurality of virtual rulers displayed on the plurality of separate images horizontally according to the horizontal movement.

The method of displaying a virtual ruler on each of a plurality of separate images of an object may further include displaying the plurality of separate images on each of which the virtual ruler is displayed; and when at least one separate image of the displayed plurality of separate images is moved vertically, moving only at least one virtual ruler displayed on the at least one separate image vertically according to the vertical movement.

According to another aspect of an exemplary embodiment, there is provided a medical image obtaining apparatus for displaying a virtual ruler on each of a plurality of separate images of an object to generate a composite image, the apparatus including: an image obtainer for dividing the object into a plurality of imaging areas in a predetermined direction and obtaining a plurality of separate images corresponding to the plurality of imaging areas; a location obtainer for obtaining a first distance of a separate image, which is a distance from a predetermined reference point to a first side of each of the plurality of separate images, and a second distance of the separate image, which is a distance from the predetermined reference point to a second side of each of the plurality of separate images; and a controller for displaying a virtual ruler, which indicates distance values between the obtained first distance of the separate image and the obtained second distance of the separate image, on each of the plurality of separate images.

The image obtainer may obtain the plurality of separate images at locations corresponding to the plurality of imaging areas by using X-rays penetrating the object.

The location obtainer may obtain, at locations corresponding to the plurality of imaging areas, a distance from the predetermined reference point to a first side of the image obtainer as the first distance of the separate image and a distance from the predetermined reference point to a second side of the image obtainer as the second distance of the separate image.

The controller may obtain an actual distance of each pixel of the separate image by using a difference value between the first distance of the separate image and the second distance of the separate image and the number of pixels in a predetermined direction of the separate image; and may display the virtual ruler on each of the plurality of separate images by using the first distance and the actual distance of each pixel, or the second distance and the actual distance of each pixel.

The controller may divide the separate image into a plurality of areas in the predetermined direction; and may display the virtual ruler on each of the plurality of separate images by using the first distance and a value, which is obtained by dividing a difference value between the first distance of the separate image and the second distance of the separate image by the number of the plurality of areas, or the second distance and the value, which is obtained by dividing a difference value between the first distance of the separate image and the second distance of the separate image by the number of the plurality of areas.

The predetermined direction may include a vertical direction of the object, the first side of each of the obtained plurality of separate images may include an upper side of each of the obtained plurality of separate images, and the second side of each of the obtained plurality of separate images may include a lower side of each of the obtained plurality of separate images.

The medical image obtaining apparatus may further include a display for displaying the plurality of separate images on each of which the virtual ruler is displayed, wherein when at least one separate image of the displayed plurality of separate images is moved horizontally, the display may not move at least one virtual ruler displayed on the at least one separate image or may simultaneously move a plurality of virtual rulers displayed on the plurality of separate images horizontally according to the horizontal movement.

The medical image obtaining apparatus may further include a display for displaying the plurality of separate images on each of which the virtual ruler is displayed, wherein when at least one separate image of the displayed plurality of separate images is moved vertically, the display may move only at least one virtual ruler displayed on the at least one separate image vertically according to the vertical movement.

According to another aspect of an exemplary embodiment, there is provided a method of displaying a virtual ruler on each of a plurality of separate images of an object by using a medical image obtaining apparatus to generate a composite image of the object, the method including: dividing the object into a plurality of imaging areas in a predetermined direction by using an image obtainer of the medical image obtaining apparatus and obtaining a plurality of separate images corresponding to the plurality of imaging areas; and displaying a virtual ruler on each of the plurality of separate images based on information about a location of the image obtainer.

The obtaining of the plurality of separate images of the object may include obtaining the plurality of separate images corresponding to the plurality of imaging areas at locations corresponding to the plurality of imaging areas by using the image obtainer.

The displaying of the virtual ruler on each of the plurality of separate images may include: obtaining a first distance of the image obtainer, which is a distance from a predetermined reference point to a first side of the image obtainer, and a second distance of the image obtainer, which is a distance from the predetermined reference point to a second side of the image obtainer; and displaying a virtual ruler, which indicates distance values between the obtained first distance of the image obtainer and the obtained second distance of the image obtainer, on each of the plurality of separate images.

The displaying of the virtual ruler on each of the plurality of separate images may include: obtaining a first distance of a separate image, which is a distance from a predetermined reference point to a first side of each of the plurality of separate images, and a second distance of the separate image, which is a distance from the predetermined reference point to a second side of each of the plurality of separate images, by using information about a location of an X-ray emitter for emitting X-rays to the object, information about a location of the image obtainer, and a distance between the object and the image obtainer; and displaying a virtual ruler, which indicates distance values between the obtained first distance of the separate image and the obtained second distance of the separate image, on each of the plurality of separate images.

The obtaining of the first distance of the separate image and the second distance of the separate image may include obtaining the first distance of the separate image and the second distance of the separate image by using a distance $x1$ between the X-ray emitter and the image obtainer, a distance $x2$ between the object and the image obtainer, the first distance $y1$ of the image obtainer, the second distance $y1'$ of the image obtainer, and a distance $y2$ from the predetermined reference point to the X-ray emitter.

The first distance of the separate image may be obtained by using an Equation $y2-\{(y2-y1)\times(x1-x2)/x1\}$, and the second distance of the separate image may be obtained by using an Equation $y2+\{(y1'-y2)\times(x1-x2)/x1\}$.

The displaying of the virtual ruler on each of the plurality of separate images may include automatically composing the plurality of separate images based on distance values of the virtual ruler displayed on each of the plurality of separate images.

The automatic composing of the plurality of separate images may include overlapping a first separate image of the plurality of separate images with a second separate image of the plurality of the separate images at points with the same distance value from among points corresponding to distance values of a first virtual ruler displayed on the first separate image and points corresponding to distance values of a second virtual ruler displayed on the second separate image.

The displaying the virtual ruler on each of the plurality of separate images may further include displaying the plurality of separate images, on each of which the virtual ruler is displayed, on a predetermined area of a display of the medical image obtaining apparatus.

The displaying of the plurality of separate images may include displaying only the plurality of separate images without the virtual ruler displayed on each of the plurality of separate images on the predetermined area, based on an off input of a user.

The displaying of the plurality of separate images may include magnifying the plurality of separate images and the virtual ruler displayed on each of the plurality of separate images, based on a zoom-in input of a user.

The magnifying of the plurality of separate images and the virtual ruler may include moving a position of a first virtual ruler displayed on a first separate image of the plurality of separate images so that the first virtual ruler is not outside the predetermined area when the first separate image and the first virtual ruler displayed on the first separate image are magnified.

The displaying of the plurality of separate images may include de-magnifying the plurality of separate images and the virtual ruler displayed on each of the plurality of separate images, based on a zoom-out input of a user.

The displaying of the plurality of separate images may include: when at least one separate image of the displayed plurality of separate images is moved horizontally by a user's input, not moving at least one virtual ruler displayed on the at least one separate image or simultaneously moving a plurality of virtual rulers displayed on the plurality of separate images horizontally according to the horizontal movement.

The displaying of the plurality of separate images may include: when at least one separate image of the displayed plurality of separate images is moved vertically by a user's input, moving only at least one virtual ruler displayed on the at least one separate image vertically according to the vertical movement.

According to another aspect of an exemplary embodiment, there is provided a method of displaying a virtual ruler on a medical image of an object by using a medical image obtaining apparatus, the method including: obtaining a medical image corresponding to an imaging area of the object by using an image obtainer of the medical image obtaining apparatus; and displaying a virtual ruler on the medical image based on information about a location of the image obtainer.

The obtaining of the medical image may include obtaining the medical image corresponding to the imaging area at a location corresponding to the imaging area of the object by using the image obtainer.

The displaying of the virtual ruler on the medical image may include: obtaining a first distance of the image obtainer, which is a distance from a predetermined reference point to a first side of the image obtainer, and a second distance of the image obtainer, which is a distance from the predetermined reference point to a second side of the image obtainer; and displaying a virtual ruler, which indicates distance values between the obtained first distance of the image obtainer and the obtained second distance of the image obtainer, on the medical image.

The displaying of the virtual ruler on the medical image may include: obtaining a first distance of a separate image, which is a distance from a predetermined reference point to a first side of the medical image, and a second distance of the separate image, which is a distance from the predetermined reference point to a second side of the medical image, by using information about a location of an X-ray emitter for emitting X-rays to the object, information about a location of the image obtainer, and a distance between the object and the image obtainer; and displaying a virtual ruler, which indicates distance values between the obtained first distance of the separate image and the obtained second distance of the separate image, on the medical image.

According to another aspect of an exemplary embodiment, there is provided a method of displaying a plurality of separate images of an object, the method including: displaying a plurality of separate images, on each of which a virtual ruler is displayed, on a predetermined area of a display; and displaying only the plurality of separate images without the virtual ruler displayed on each of the plurality of separate images on the predetermined area, based on an off input of a user.

The method of displaying a plurality of separate images of an object may further include magnifying the plurality of separate images and the virtual ruler displayed on each of the plurality of separate images, based on a zoom-in input of a user.

The magnifying of the plurality of separate images and the virtual ruler may include moving a position of a first virtual ruler displayed on a first separate image of the plurality of separate images so that the first virtual ruler is not outside the predetermined area when the first separate image and the first virtual ruler displayed on the first separate image are magnified.

The method of displaying a plurality of separate images of an object may further include de-magnifying the plurality of separate images and the virtual ruler displayed on each of the plurality of separate images, based on a zoom-out input of a user.

The method of displaying a plurality of separate images of an object may further include: when at least one separate image of the displayed plurality of separate images is moved horizontally by a user's input, not moving at least one virtual ruler displayed on the at least one separate image or simultaneously moving a plurality of virtual rulers displayed on the plurality of separate images horizontally according to the horizontal movement.

The method of displaying a plurality of separate images of an object may further include: when at least one separate image of the displayed plurality of separate images is moved vertically by a user's input, moving only at least one virtual ruler displayed on the at least one separate image vertically according to the vertical movement.

According to another aspect of an exemplary embodiment, there is provided a computer-readable recording medium having recorded thereon a program for executing the method of displaying a virtual ruler on each of a plurality of separate images of an object or the method of displaying a virtual ruler on a medical image of an object.

According to another aspect of an exemplary embodiment, there is provided a computer-readable recording medium having recorded thereon a program for executing the method of displaying a plurality of separate images of an object.

According to another aspect of an exemplary embodiment, there is provided a medical image obtaining apparatus for displaying a virtual ruler on each of a plurality of separate images of an object to generate a composite image, the apparatus including: an image obtainer for dividing the object into a plurality of imaging areas in a predetermined direction and obtaining a plurality of separate images for the object; a location obtainer for obtaining information about a location of the image obtainer; and a controller for displaying a virtual ruler on each of the plurality of separate images based on the information about the location of the image obtainer.

According to another aspect of an exemplary embodiment, there is provided a medical image obtaining apparatus including: an image obtainer for obtaining a medical image corresponding to an imaging area of an object; a location obtainer for obtaining information about a location of the image obtainer; and a controller for displaying a virtual ruler on the medical image based on the information about the location of the image obtainer.

According to another aspect of an exemplary embodiment, there is provided a display device including: a display for displaying a plurality of separate images, on each of which a virtual ruler is displayed, on a predetermined area; and a user input unit for receiving a predetermined input from a user, wherein the display displays only the plurality of separate images without the virtual ruler displayed on each of the plurality of separate images on the predetermined area, based on an off input of a user, which is received through the user input unit.

According to another aspect of an exemplary embodiment, there is provided a medical image obtaining apparatus including: an image obtainer which includes an X-ray emitter configured to emit X-rays toward an object and an X-ray detector configured to detect X-rays that penetrated the object, wherein the image obtainer is configured to obtain an image of a portion of the object based on the detected X-rays; a controller configured to generate a virtual ruler which indicates information about a location of the image based on a rotation angle of the X-ray emitter; and a display configured to display the virtual ruler on the image.

The image obtainer is further configured to rotate the X-ray emitter so that a direction of the X-rays emitted toward the object is changed in order to obtain the image of the portion of the object. The image obtainer is further configured to move the X-ray detector in a predetermined direction according to the rotation of the X-ray emitter.

The X-rays emitted by the X-ray emitter may pass through a collimator to reach the object. The controller is further configured to generate the virtual ruler based on an opening size of the collimator, a distance from an X-ray tube of the X-ray emitter to the collimator, and a distance from the X-ray emitter to the X-ray detector.

The controller is further configured to generate the virtual ruler based on a size of the X-ray detector and a distance from the X-ray emitter to the X-ray detector.

The virtual ruler may indicate information about a distance from a reference point to a first side of the image and a distance from the reference point to a second side of the image.

The reference point may correspond to a first side of the X-ray detector when the X-ray detector is located at a reference position.

The virtual ruler may include gradations which indicate values between the distance from the reference point to the first side of the image and the distance from the reference point to the second side of the image as predetermined gaps.

The image obtainer is further configured to rotate the X-ray emitter so that a direction of the X-rays emitted toward the object is changed and to move the X-ray detector in a predetermined direction according to the rotation of the X-ray emitter, in order to divide the object into a plurality of portions in a predetermined direction and obtain a plurality of images corresponding to the plurality of portions. The controller is further configured to generate a plurality of virtual rulers, which indicate information about a location of each of the plurality of images, based on the rotation angle at which the X-ray emitter is rotated to obtain each of the plurality of images.

Each of the plurality of virtual rulers may indicate information about a distance from a reference point to a first side of the image and a distance from the reference point to a second side of the image. The controller may determine a first side of an image firstly obtained from among the plurality of images as the reference point.

The medical image obtaining apparatus may further include a user input unit configured to receive a user's input for changing a reference point. The controller is further configured to generate the virtual ruler which indicates information about a distance from the reference point that is changed, based on the user's input to the image.

The controller is further configured to generate the virtual ruler based on a distance from the object to the X-ray detector.

The medical image obtaining apparatus may further include a user input unit configured to receive a user's input. The controller is further configured to control the display based on the user's input such that only the image without the virtual ruler is displayed, a location of the virtual ruler on the image is changed, or gaps of gradations included in the virtual ruler are changed.

According to another aspect of an exemplary embodiment, there is provided a method of displaying a medical image, the method including: obtaining an image of a portion of an object based on detected X-rays by irradiating X-rays towards the object by using an X-ray emitter and detecting the X-rays that penetrate the object by using an X-ray detector; generating a virtual ruler which indicates information about a location of the image based on a rotation angle of the X-ray emitter; and displaying the virtual ruler on the image.

According to another aspect of an exemplary embodiment, there is provided a medical image obtaining apparatus including: an image obtainer that includes an X-ray emitter configured to emit X-rays towards an object and an X-ray detector configured to detect X-rays that penetrate the object and to obtain an image of a portion of the object based on the detected X-rays; a controller configured to generate a virtual ruler which indicates information about a location of the image, based on a moved distance of the X-ray emitter; and a display configured to display the virtual ruler on the image.

According to another aspect of an exemplary embodiment, there is provided a medical image obtaining apparatus including: an image obtainer that includes an X-ray emitter configured to emit X-rays towards an object and an X-ray detector configured to detect X-rays that penetrate the object and to obtain a first image of a first portion of the object, based on the X-rays detected when the X-ray detector is located at a first position and obtains a second image of a second portion of the object, based on the X-rays detected when the X-ray detector is moved in a predetermined direction from the first position to a second position; a controller configured to generate a first virtual ruler indicating information about a location of the first image and a second virtual ruler indicating information about a location of the second image, based on a size of the X-ray detector; and a display configured to display the first virtual ruler on the first image and the second virtual ruler on the second image.

The controller is further configured to generate the second virtual ruler based on at least one of a distance by which the X-ray detector is moved from the first position to be located at the second position and a length of a section in which the X-ray detector located at the first position overlaps the X-ray detector located at the second position.

The first virtual ruler may indicate information about a distance from a reference point to a first side of the first image and a distance from the reference point to a second side of the first image, and the second virtual ruler may indicate information about a distance from the reference point to a first side of the second image and a distance from the reference point to the second side of the second image.

The reference point may correspond to a first side of the X-ray detector, when the X-ray detector is located at a reference position.

The first virtual ruler may include gradations which indicate values between the distance from the reference point to the first side of the first image and the distance from the reference point to the second side of the first image as predetermined gaps.

The controller may determine the first side of the first image obtained when the X-ray detector is located at the first position as the reference point.

The medical image obtaining apparatus may further include a user input unit configured to receive a user's input for changing a reference point. The controller is further configured to generate the first virtual ruler indicating information about a distance from the reference point changed based on the user's input to the first image and the second virtual ruler indicating information about a distance from the changed reference point to the second image.

The controller is further configured to generate the first virtual ruler and the second virtual ruler based on a distance from the object to the X-ray detector.

The medical image obtaining apparatus may further include a user input unit configured to receive a user's input. The controller is further configured to control the display based on the use's input such that only the first image without the first virtual ruler is displayed, a location of the first virtual ruler on the first image is changed, or gaps of gradations included in the first virtual ruler are changed.

According to another aspect of an exemplary embodiment, there is provided a method of displaying a medical image, the method including: obtaining a first image of a first portion of an object based on detected X-rays by irradiating X-rays towards the object by using an X-ray emitter and detecting the X-rays that penetrate the object by using an X-ray detector located at a first position; obtaining a second image of a second portion of the object based on detected X-rays, by irradiating X-rays toward the object by using the X-ray emitter and detecting the X-rays that penetrate the object by using the X-ray detector which is moved in a predetermined direction from the first position to a second position; generating a first virtual ruler indicating information about a location of the first image and a second virtual ruler indicating information about a location of the second image based on a size of the X-ray detector; and displaying the first virtual ruler on the first image and the second virtual ruler on the second image.

According to another aspect of an exemplary embodiment, there is provided a medical image obtaining apparatus including: an image obtainer that includes an X-ray configured to emit X-rays towards an object and an X-ray detector configured to detect X-rays that penetrate the object and to obtain a first image of a first portion of the object based on the X-rays detected when the X-ray detector is located at a first position and a second image of a second portion of the object based on the X-rays detected when the X-ray detector is moved in a predetermined direction from the first position to a second position; a user input unit for receiving a user's input; a controller configured to generate a first virtual ruler indicating information about a distance from a reference point to a first side of the first image and a distance from the reference point to a second side of the first image and a second virtual ruler indicating information about a distance from the reference point to a first side of the second image and a distance from the reference point to a second side of the second image, and further configured to generate a composite image by combining the first image and the second image by using a method determined based on the user's input; and a display configured to display the composite image.

The user's input is for selecting one of a first method and a second method, wherein the first method is a method for generating the composite image by combining the first image and the second image based on the first virtual ruler and the second virtual ruler, and the second method is a method for generating the composite image by combining the first image and the second image based on a result of analyzing a portion of the first image that overlaps the second image and a portion of the second image that overlaps the first image.

When the user's input selects the first method, the controller is further configured to compose the first image and the second image by overlapping points having the same value on the first virtual ruler and the second virtual ruler.

According to another aspect of an exemplary embodiment, there is provided a method of displaying a medical image, the method including: obtaining a first image of a first portion of an object based on detected X-rays by irradiating X-rays towards the object by using an X-ray emitter and detecting the X-rays that penetrate the object by using an X-ray detector located at a first position; obtaining a second image of a second portion of the object based on detected X-rays by irradiating X-rays toward the object by using the X-ray emitter and detecting the X-rays that penetrate the object by using the X-ray detector that is moved in a predetermined direction from the first position to a second position; generating a first virtual ruler indicating information about a distance from a reference point to a first side of the first image and a distance from the reference point to a second side of the first image and a second virtual ruler indicating information about a distance from the reference point to a first side of the second image and a distance from the reference point to a second side of the second image; receiving a user's input; generating a composite image by combining the first image and the second image by using a method determined based on the user's input; and displaying the composite image.

BRIEF DESCRIPTION OF THE DRAWINGS

The above and/or other aspects will become more apparent by describing certain exemplary embodiments, with reference to the accompanying drawings, in which:

FIGS. 29, 30, and 31 are diagrams of an example of a screen displayed for generating a composite image, according to an exemplary embodiment.

DETAILED DESCRIPTION

Figure 1:
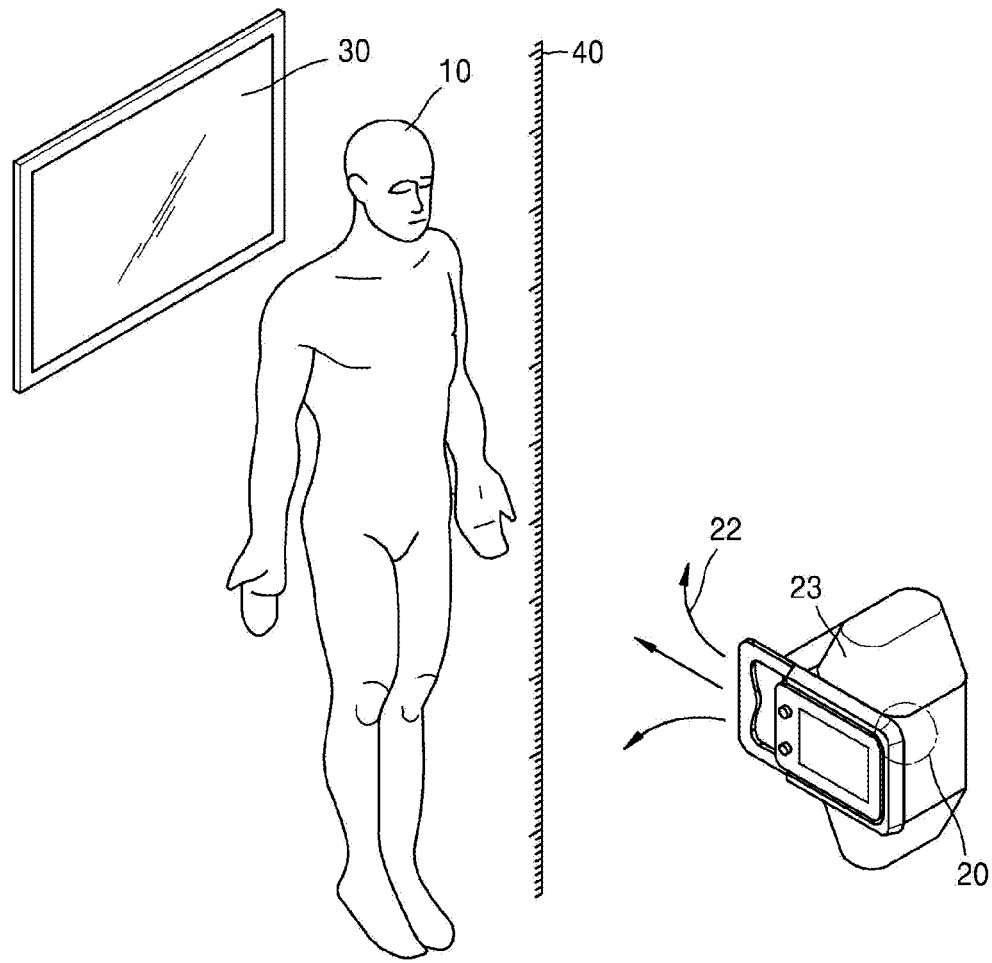
FIG. 1 is a diagram for explaining a method of capturing separate images of an object to generate a composite image of the object.

Certain exemplary embodiments are described below with reference to the accompanying drawings.

In the following description, same drawing reference numerals are used for the same elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

The term unit in exemplary embodiments means a software component or hardware components such as a field-programmable gate array (FPGA) or an application-specific integrated circuit (ASIC), and performs a specific function. However, the unit is not limited to software or hardware. The unit may be an addressable storage medium, or may be formed to operate one or more processors. Thus, for example, the unit may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and units may be associated with the smaller number of components and units, or may be divided into additional components and units.

In exemplary embodiments, an object denotes a target object or a part of the target object for medical image capture, and may include a human, an animal, or a portion of a human or animal.

In exemplary embodiments, the expression "a value A corresponds to a value B" may denote that the value A is the same as, substantially the same as, or proportional to the value B. For example, when the value A is proportional to the value B, the value B may be obtained by multiplying the value A by a predetermined coefficient. When the value A is substantially the same as the value B, a difference between the value A and the value B is within a predetermined range.

FIG. 1 is a diagram for explaining a method of capturing separate images of an object to generate a composite image of the object. FIG. 1 illustrates a method of generating a composite image by using an X-ray apparatus.

When an X-ray tube 20 of an X-ray emitter 23 emits X-rays 22 toward an object 10, an image obtainer 30 obtains an image of the object 10 by sensing X-rays penetrating the object 10. The image obtainer 30 may include an X-ray detector of the X-ray apparatus.

In order to generate a composite image of the object 10, images of portions of the object 10 are obtained while rotating or moving the X-ray tube 20 and moving the image obtainer 30, for example, upward and downward since the size of the image obtainer 30 is generally smaller than that of the object 10. Then, a composite image of the object 10 is obtained by composing the images of the portions.

When capturing separate images of the object 10 according to a related art composite image generating method, a lead ruler 40 is placed beside the object 10 to indicate the location of each of separate images on each of the separate images, and the object 10 and the lead ruler 40 are imaged together. However, the placement of the lead ruler 40 beside the object results in wasteful expense and inconvenience in terms of utilization of an X-ray imaging space.

An apparatus and method of displaying a virtual ruler on each of a plurality of separate images of an object, according to exemplary embodiments, may accurately display information about the location of each of a plurality of separate images on each of the plurality of separate images without having to place the lead ruler 40 beside the object during imaging.

Figure 2:
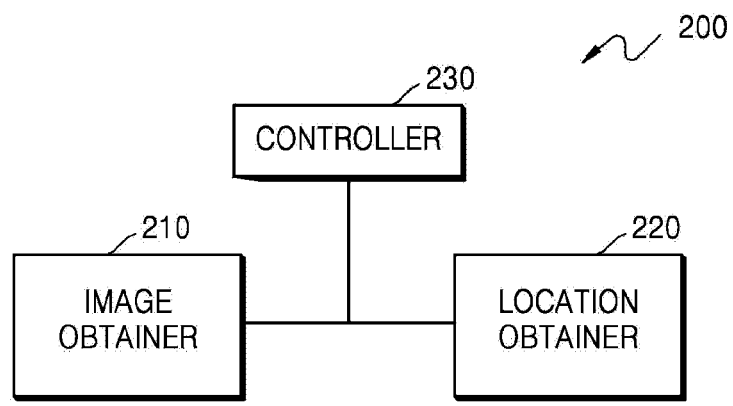
FIG. 2 is a block diagram of a medical image obtaining apparatus according to an exemplary embodiment.

FIG. 2 is a block diagram of a medical image obtaining apparatus 200 according to an exemplary embodiment.

Referring to FIG. 2, the medical image obtaining apparatus 200 may include an image obtainer 210, a location obtainer 220, and a controller 230.

The medical image obtaining apparatus 200 may be included in an X-ray apparatus, and the location obtainer 220 or the controller 230 may be configured by using a microprocessor.

The image obtainer 210 divides the object into a plurality of imaging areas in a predetermined direction, and obtains a plurality of separate images of the object corresponding to the respective imaging areas. The image obtainer 210 may include an X-ray detector of an X-ray apparatus.

Figure 3:
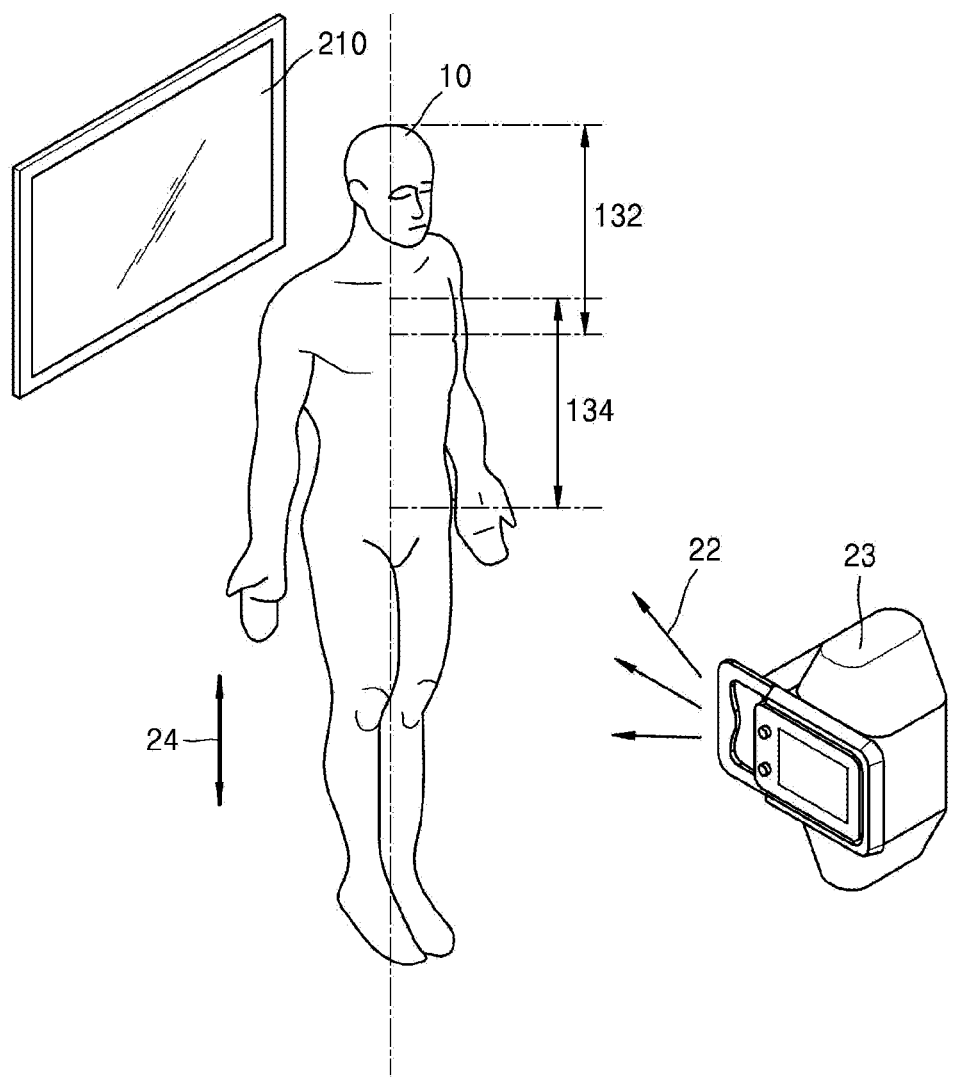
FIG. 3 is a diagram illustrating a plurality of imaging areas of an object.

FIG. 3 is a diagram illustrating a plurality of imaging areas 132 and 134 of an object. The image obtainer 210 may move in the vertical direction 24 and may divide the object 10 into a plurality of imaging areas in the vertical direction 24. In detail, the image obtainer 210 may divide the object 10 into a plurality of imaging areas 132 and 134 in the vertical direction 24, may move to the plurality of imaging areas 132 and 134, and may obtain separate images corresponding to the plurality of imaging areas of the object 10 by sensing X-rays 22 penetrating the object 10. The separate images may partially overlap each other. Although FIG. 3 illustrates only two imaging areas 132 and 134, the object 10 may be divided into three or more imaging areas.

The location obtainer 220 may obtain a first distance from a predetermined reference point to a first side of each of the separate images and a second distance from the predetermined reference point to a second side of each of the separate images. The predetermined reference point may be located in an upper side of the image obtainer 210 when the image obtainer 210 is located at the greatest point with respect to a freedom of movement in the vertical direction 24. The first side may include a side surface or a side edge of a separate image, and the second side may include the other side surface or the other side edge of the same separate image. The first side and the second side may be disposed opposite to each other with respect to the separate image.

The controller 230 may display a virtual ruler, which indicates distance values between the first distance and the second distance, on each of the plurality of separate images.

For example, when a first distance of a first separate image of the plurality of separate images is measured to be 10 cm and a second distance of the first separate image is measured to be 30 cm, a virtual ruler from 10 cm to 30 cm is displayed on the first separate image. A user may accurately compose the plurality of separate images by using virtual rulers displayed on the plurality of separate images.

As an example the controller 230 may obtain an actual distance of each pixel of a separate image by using a difference value between first distance and the second distance and the number of pixels in a predetermined direction of the separate image. For example, when the first distance of the first separate image is 10 cm, the second distance is 30 cm, and the total number of pixels in a predetermined direction is 100, an actual distance of each pixel is 2 mm ((300 mm−100 mm)/100).

The controller 230 may determine a virtual ruler corresponding to distance values between the first distance and the second distance on each of the plurality of separate images by using the first distance and the actual distance of each pixel, or the second distance and the actual distance of each pixel. For example, when the first distance of the first separate image is 10 cm, the second distance is 30 cm, and the number of pixels in a predetermined direction is 100, a distance to a pixel which is located after a tenth pixel from the first side is 120 mm (100 mm+10×2 mm) with respect to the predetermined reference point R. The controller 230 may determine a distance value of each pixel of a separate image, and/or a distance value corresponding to a predetermined number of pixels of the separate image. Based on the above-described example, a length of ten pixels is 20 mm.

As another example, the controller 230 may divide each separate image into a plurality of areas in a predetermined direction, and may determine distance values corresponding to distances between dividing points, at which the plurality of areas are divided, by using the first distance and a value which is obtained by dividing a difference value between the first distance and the second distance by the number of the plurality of areas, or the second distance and a value which is obtained by dividing a difference value between the first distance and the second distance by the number of the plurality of areas.

For example, if a separate image is divided into ten areas, and a difference value between first distance and the second distance is 20 cm, an actual distance of each area is 2 cm (20 cm/10). Accordingly, a distance to a dividing point at which a fifth area located at a fifth position from the first side and an sixth area located at a sixth position from the first side are divided, is 20 cm (10 cm+5×2 cm), with respect to the predetermined reference point.

Figure 4:
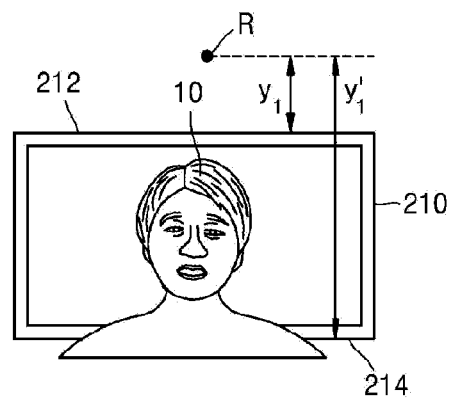
FIG. 4 is a diagram illustrating a first distance and second distance of the image obtainer, in the medical image obtaining apparatus according to an exemplary embodiment.

FIG. 4 is a diagram illustrating first distance y1 of the image obtainer 210 and second distance y1' of the image obtainer 210, in the medical image obtaining apparatus 200 illustrated in FIG. 2.

The location obtainer 220 may obtain information about the location of the image obtainer 210, and the controller 230 may display a virtual ruler on each of a plurality of separate images based on the information about the location of the image obtainer 210. In detail, the location obtainer 220 may obtain the first distance y1 of the image obtainer 210 and the second distance y1' of the image obtainer 210, and may set the first distance y1 of the image obtainer 210 and the second distance y1' of the image obtainer 210 as first distance of a separate image and the second distance of the separate image, respectively.

Referring to FIG. 4, the first distance y1 is a distance from a predetermined reference point R to an upper side 212 of the image obtainer 210, and the second distance y1' is a distance from the predetermined reference point R to a lower side 214 of the image obtainer 210. For example, the upper side includes an upper side edge or an upper side surface, and the lower side includes a lower side edge or a lower side surface. The X-ray apparatus may measure the first distance and the second distance of the image obtainer 210 to accurately determine which portion of the object is being imaged. When the image obtainer 210 is located at the greatest height, and the predetermined reference point R is set to be located in the upper side of the image obtainer 210, a distance from the predetermined reference point R to the upper side of the image obtainer 210 is zero.

Figure 5:
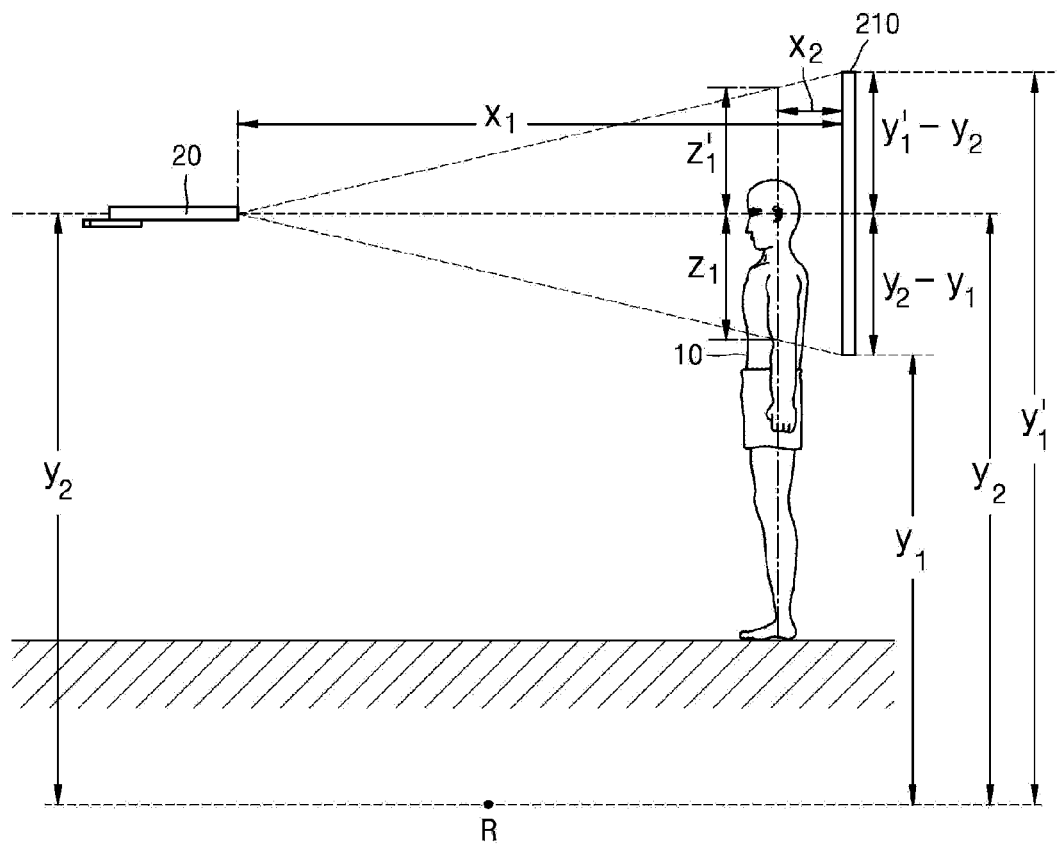
FIG. 5 is a diagram for explaining another method of measuring a first distance and a second distance of the separate image.

FIG. 5 is a diagram for explaining another method of measuring first distance of a separate image and second distance of the separate image.

In order to take an X-ray of an object 10, the object 10 is spaced apart from the image obtainer 210 by a predetermined distance. Accordingly, as described above, if the location obtainer 220 sets first distance of the image obtainer 210 and the second distance of the image obtainer 210 as first distance of a separate image and the second distance of the separate image, respectively, an actual length of the object 10 or an actual length of an organ included in the object 10 may be measured with insufficient accuracy.

To improve the accuracy, the location obtainer 220 may obtain the first distance of a separate image and the second distance of the separate image by using information about the location of the X-ray emitter 23 for emitting X-rays to the object 10, information about the location of the image obtainer 210, and a distance between the object 10 and the image obtainer 210.

In detail, when a distance between the X-ray emitter 20 and the image obtainer 210 is x1, the distance between the object 10 and the image obtainer 210 is x2, first distance of the image obtainer 210 is y1, second distance of the image obtainer 210 is y1', and a distance from a predetermined reference point to the X-ray emitter 20 is y2, z1 illustrated in FIG. 5 may be calculated by using Equation 1 and z1' illustrated in FIG. 5 may be calculated by using Equation 2.

$$z1 = (y2 - y1) \times (x1 - x2)/x1 \quad (1)$$

$$z1' = (y1' - y2) \times (x1 - x2)/x1 \quad (2)$$

A distance from z1 to first side of a separate image, that is, first distance of the separate image may be calculated by using Equation 3, and a distance from z1' to second side of a separate image, that is, second distance of the separate image may be calculated by using Equation 4.

$$\text{First distance of separate image} = y2 - \{(y2-y1) \times (x1-x2)/x1\} \quad (3)$$

$$\text{Second distance of separate image} = y2 + \{(y1'-y2) \times (x1-x2)/x1\} \quad (4)$$

The controller 230 may display a virtual ruler indicating distance values between first distance of a separate image and second distance of the separate image, which are calculated by using Equation 3 and Equation 4, on each of a plurality of separate images. Since the virtual ruler obtained by using Equation 3 and Equation 4 indicates an actual distance with respect to a predetermined reference point, a user may easily measure an actual length of an object of each separate image or an actual length of an organ included in the object.

Although a case where a virtual ruler is displayed on a plurality of separate images of an object is described above, a virtual ruler may be displayed on a single medical image of an object. That is, a virtual ruler may be displayed on a medical image, such as an image of a lung or an image of a breast, rather than on separate images for generating a composite image of an object.

In detail, the image obtainer 210 obtains a medical image corresponding to an imaging area of an object. The imaging area of an object may be set by a user, and may include a head area, a breast area, or an abdomen area.

The location obtainer 220 obtains information about the location of the image obtainer 210. The location obtainer 220 may obtain first distance of the image obtainer 210 and second distance of the image obtainer 210.

The controller 230 displays a virtual ruler on a medical image based on the information about the location of the image obtainer 210. In detail, the controller 230 may display a virtual ruler, which indicates distance values between the first distance of the image obtainer 210 and the second distance of the image obtainer 210, on a medical image. In addition, the controller 230 may also display a virtual ruler indicating distance values between first distance of a medical image and second distance of the medical image, which are obtained by using Equation 3 and Equation 4, on the medical image.

Figure 6:
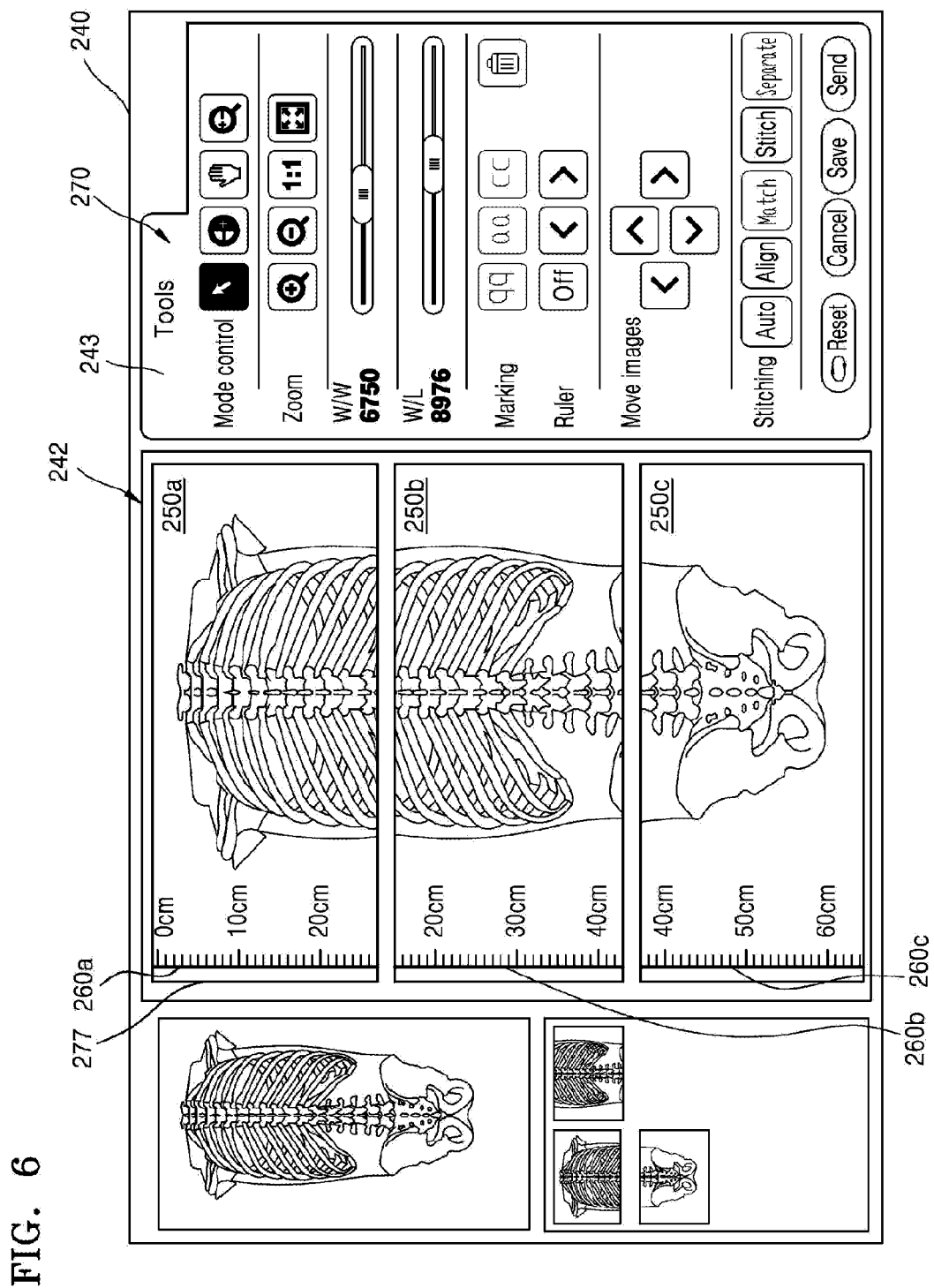
FIG. 6 is a diagram illustrating a display of the medical image obtaining apparatus, according to an exemplary embodiment.

FIG. 6 is a diagram illustrating a display 240 of the medical image obtaining apparatus 200, according to an exemplary embodiment. The display 240 may be a component included in the apparatus 200 illustrated in FIG. 2.

The display 240 of the medical image obtaining apparatus 200 may display a plurality of separate images 250a, 250b, and 250c, on which virtual rulers 260a, 260b, and 260c respectively are shown, on a predetermined area 242 of the display 240.

The display 240 illustrated in FIG. 6 displays a first separate image 250a together with a first virtual ruler 260a, a second separate image 250b together with a second virtual ruler 260b, and a third separate image 250c together with a third virtual ruler 260c on the predetermined area 242. In addition, the display 240 displays a toolbar 270 for controlling the first separate image 250a, the second separate image 250b, and the third separate image 250c on an area 243 that is different from the predetermined area 242. The toolbar 270 is an interface provided for users, and a user may input a predetermined input to the toolbar 270 by using a user input unit.

The user input unit may include a mouse, a keyboard, a trackball, etc., but is not limited thereto. If the display 240 is a touch screen, the display 240 may be used as the user input unit.

Figure 7:
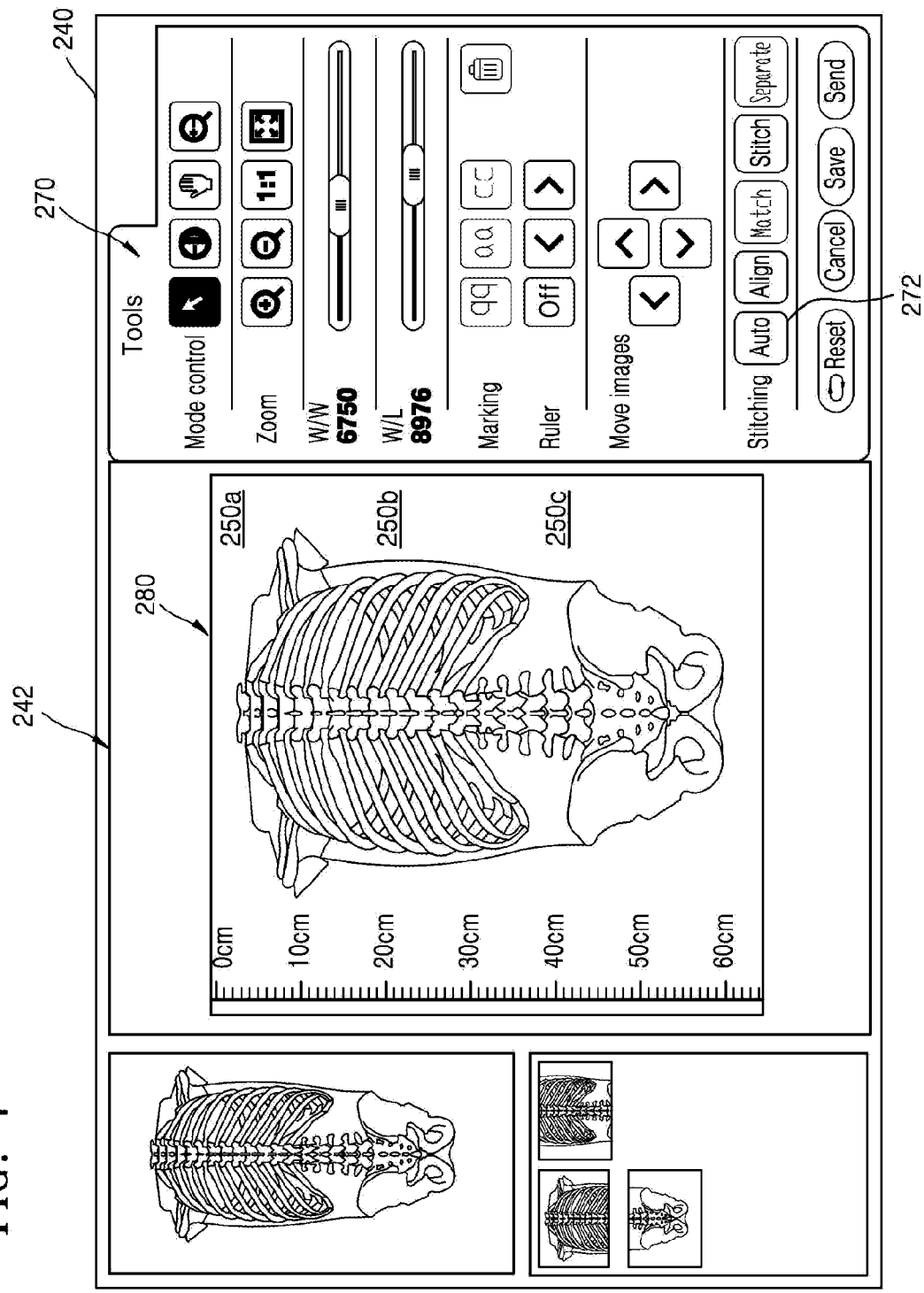
FIG. 7 is a diagram illustrating a display that displays a composite image obtained by composing the separate images.

FIG. 7 is a diagram illustrating the display 240 that displays a composite image obtained by composing or composing the first separate image 250a, the second separate image 250b, and the third separate image 250c.

A user may manually compose the first separate image 250a, the second separate image 250b, and the third separate image 250c with reference to distance values shown on the scales of the first through third virtual rulers 260a, 260b, and 260c that are displayed on the first through third separate images 250a, 250b, and 250c, respectively.

In addition, the medical image obtaining apparatus 200 according to the current exemplary embodiment may provide an automatic composition function to a user. The controller 230 may automatically compose the first separate image 250a, the second separate image 250b, and the third separate image 250c based on distance values of the first through third virtual rulers 260a, 260b, and 260c displayed on the first through third separate images 250a, 250b, and 250c, respectively, when an automatic composition input 272 is received from a user.

The controller may compose the first separate image 250a and the second separate image 250b by overlapping the first separate image 250a and the second separate image 250b at two points with the same distance value from among points corresponding to distance values of the first virtual ruler 260a displayed on the first separate image 250a and points corresponding to distance values of the second virtual ruler 260b displayed on the second separate image 250b. For example, when each of scales of the first and second virtual rulers 260a and 260b displayed on the first and second separate images 250a and 250b, respectively, includes a point corresponding to a distance value of 20 cm, the controller 230 may overlap the first separate image 250a and the second separate image 250b at two points corresponding to the distance value of 20 cm on the first and second virtual rulers 260a and 260b.

Figure 8:
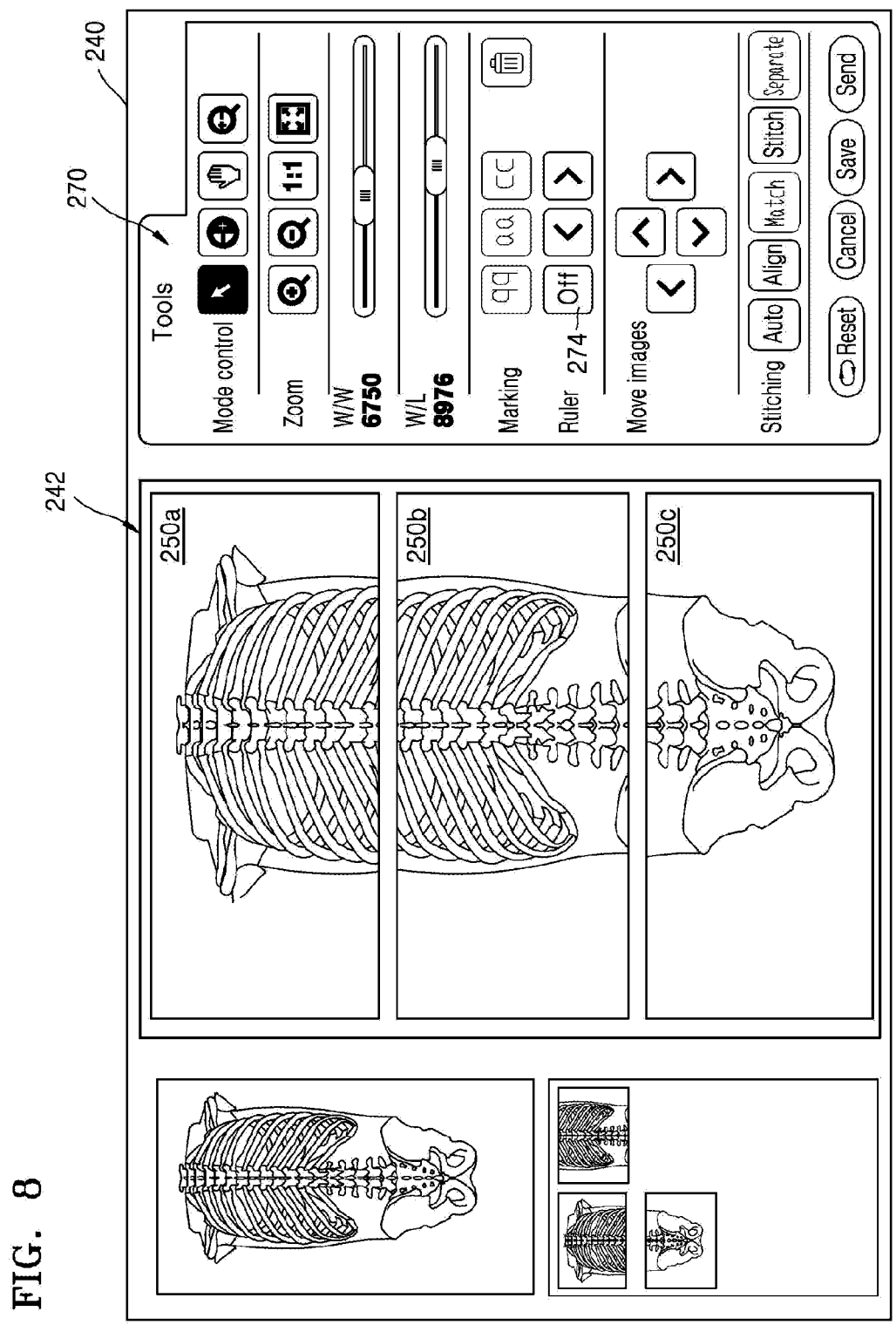
FIG. 8 is a diagram illustrating a display that displays only separate images without displaying virtual rulers.

FIG. 8 is a diagram illustrating the display 240 that displays only the first separate image 250a, the second separate image 250b, and the third separate image 250c without displaying the first through third virtual rulers 260a, 260b, and 260c.

In the related art, if a lead ruler and an object are imaged together to display an image of the lead ruler and the object, it is very difficult to delete the lead ruler from separate images. Thus, it may be difficult for a user to accurately identify the object when the lead ruler hides the object.

Since the virtual rulers 260a, 260b, and 260c according to an exemplary embodiment are not imaged together with an object, the virtual rulers 260a, 260b, and 260c may be easily eliminated from separate images. That is, when an off input 274 is received from a user, the controller 230 may delete the first through third virtual rulers 260a, 260b, and 260c displayed on the first through third separate images 250a, 250b, and 250c, respectively, and may display only the first through third separate images 250a, 250b, and 250c on the display 240. When an input which deactivates the off input or an on input is received from a user, the controller 230 may display the first through third virtual rulers 260a, 260b, and 260c again on the first through third separate images 250a, 250b, and 250c, respectively.

Figure 9:
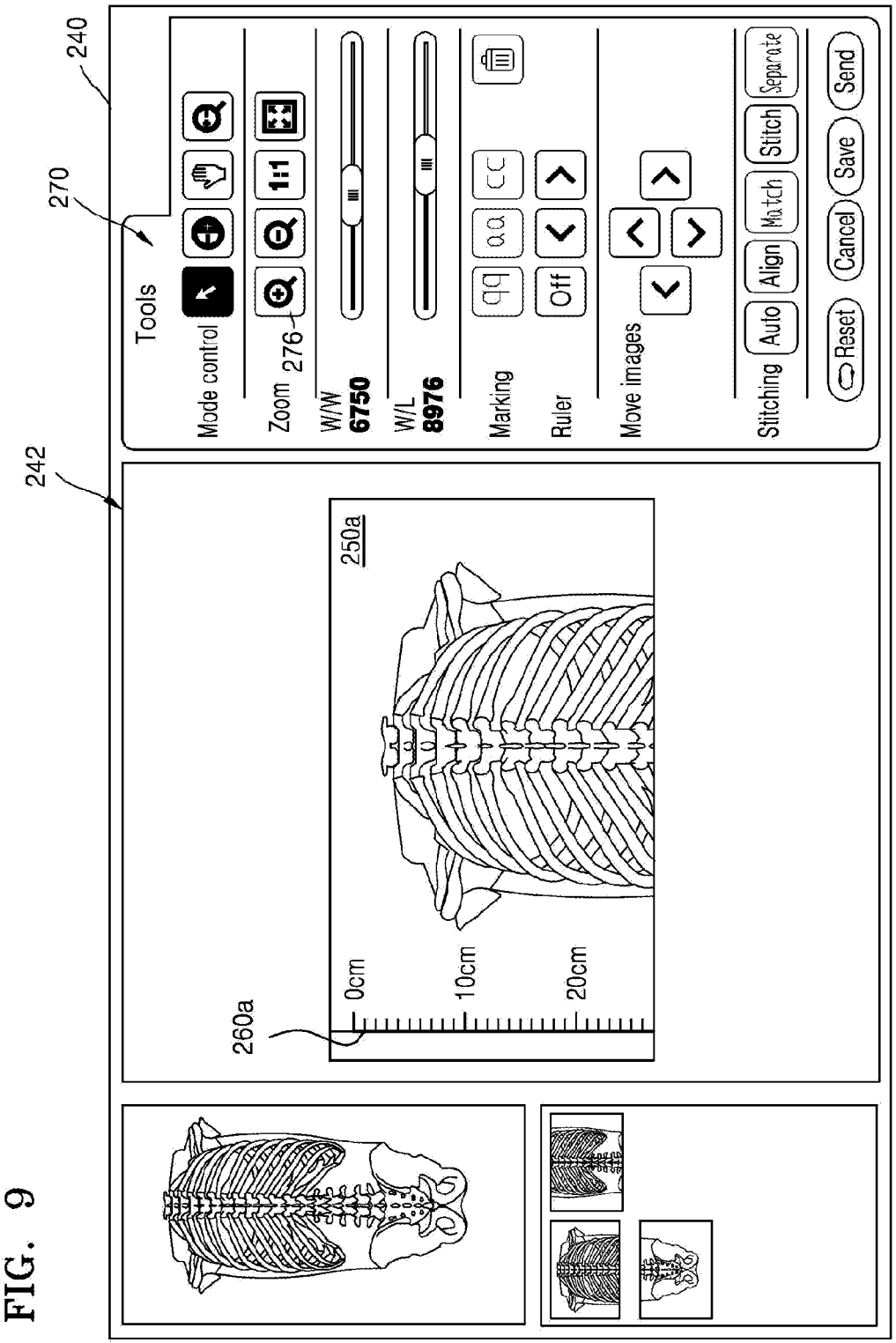
FIG. 9 is a diagram illustrating a display that displays a separate image and a virtual ruler, which are magnified.
Figure 10:
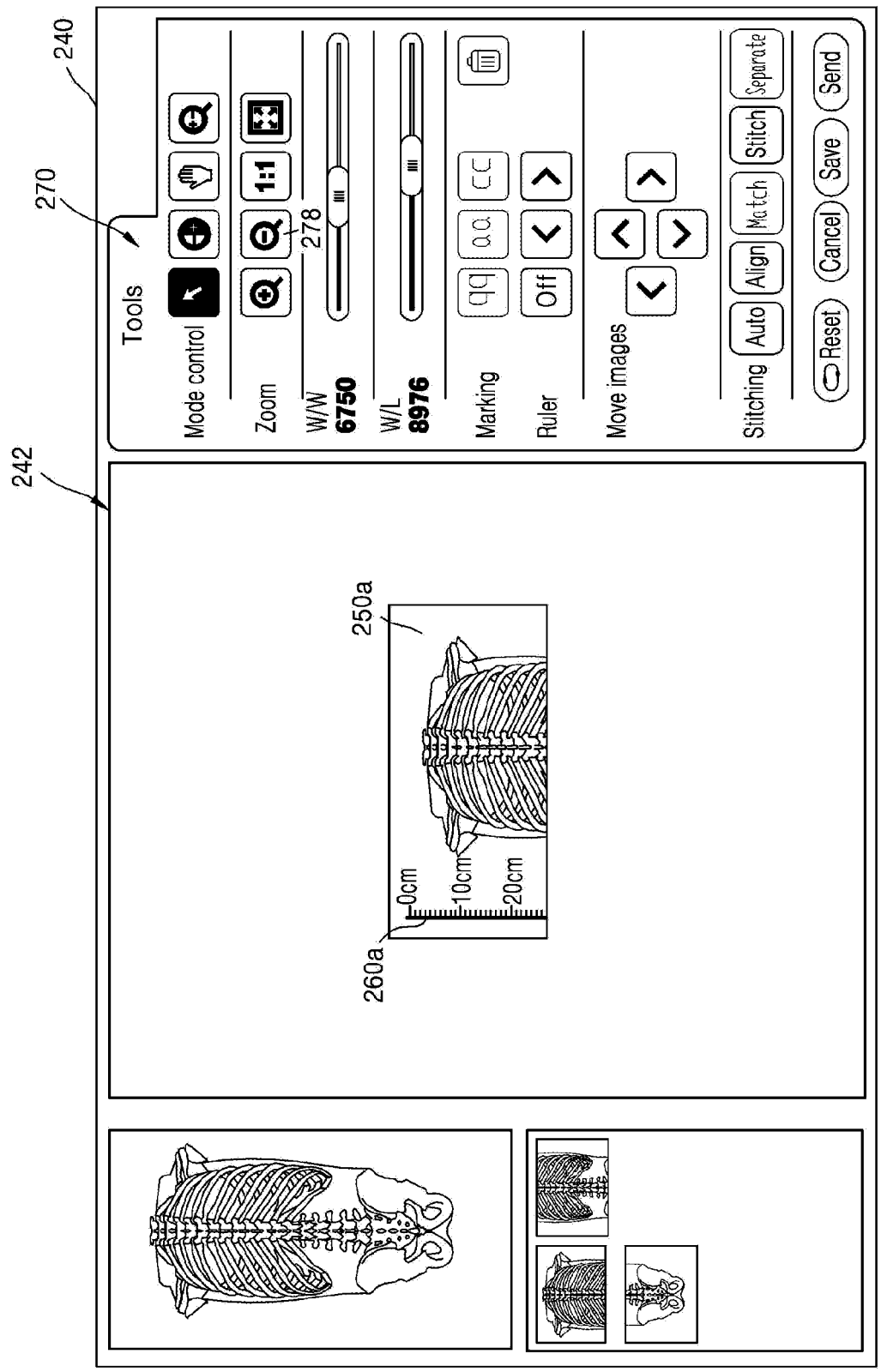
FIG. 10 is a diagram illustrating a display that displays a separate image and a virtual ruler, which are de-magnified.

FIG. 9 is a diagram illustrating the display 240 that displays the first separate image 250a and the first virtual ruler 260a, which are magnified by the controller 230, and FIG. 10 is a diagram illustrating the display 240 that displays the first separate image 250a and the first virtual ruler 260a, which are de-magnified by the controller 230.

As illustrated in FIG. 9, the controller 230 may magnify the first separate image 250a and the first virtual ruler 260a displayed on the first separate image 250a by a predetermined magnifying power when a zoom-in input 276 for the first separate image 250a is received from a user.

As illustrated in FIG. 10, the controller 230 may de-magnify the first separate image 250a and the first virtual ruler 260a displayed on the first separate image 250a by a predetermined magnifying power when a zoom-out input 278 for the first separate image 250a is received from a user.

Figure 11:
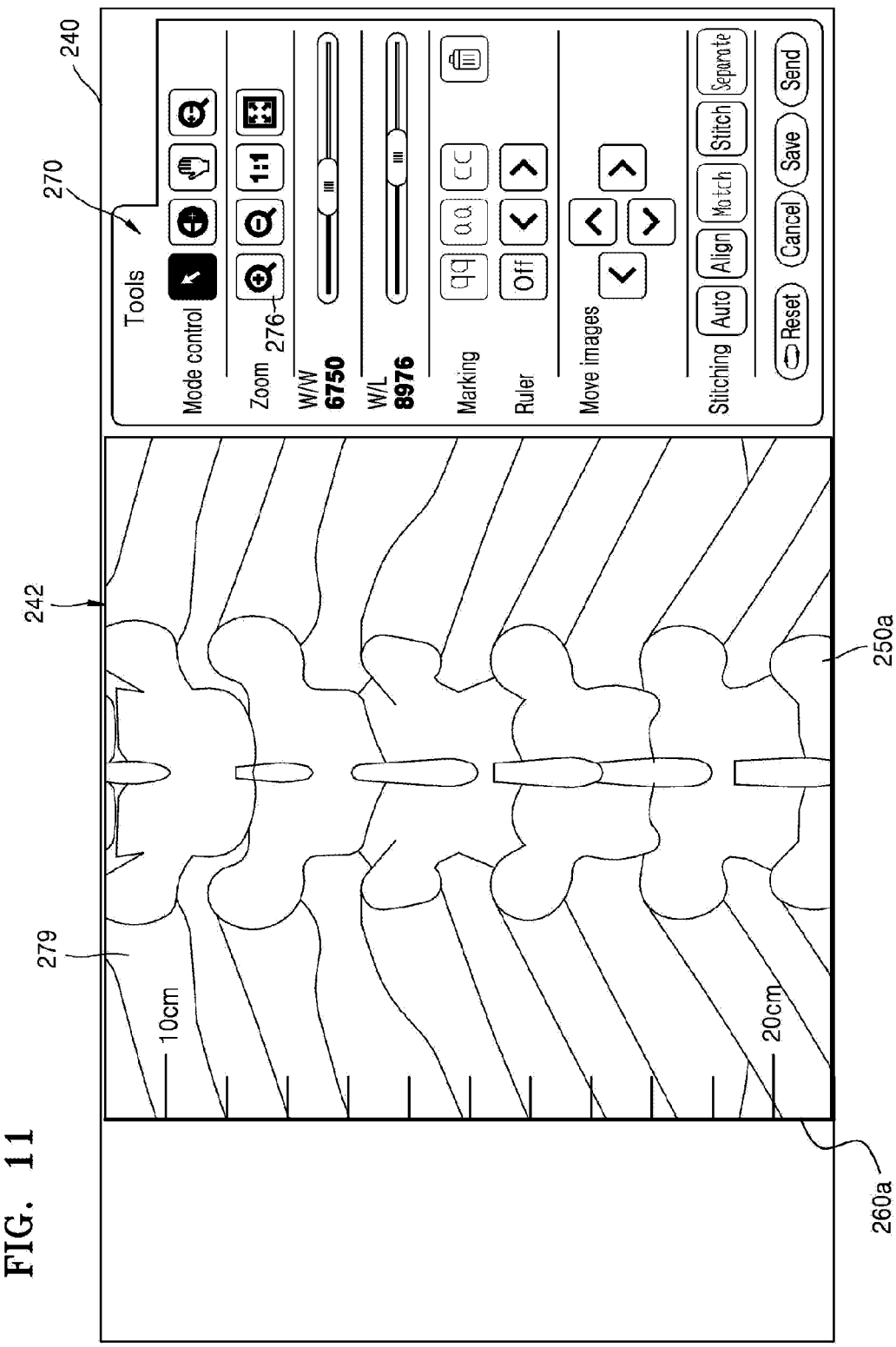
FIG. 11 is a diagram illustrating a display that displays a separate image and a virtual ruler, which are greatly magnified compared to a predetermined area.

FIG. 11 is a diagram illustrating the display 240 that displays the first separate image 250a and the first virtual ruler 260a, which are greatly magnified compared to a predetermined area.

In the related art in which a lead ruler and an object are imaged together, when a user greatly magnifies a separate image compared to a predetermined area of the display 240, a lead ruler displayed on the separate image may be out of the predetermined area of the display 240 and thus the user cannot check the lead ruler.

Accordingly, when the first separate image 250a and the first virtual ruler 260a are magnified according to the zoom-in input 276 of a user, the controller 230 may move a position of the first virtual ruler 260a so that the first virtual ruler 260a is not out of the predetermined area of the display 240.

In FIG. 11, the first virtual ruler 260a displayed on an outside area 277 of the first separate image 250a illustrated in FIG. 6 moves to an inside area 279 of the first separate image 250a with the magnification of the first virtual ruler 260a, and thus is displayed in a predetermined area 242 of the display 240.

Figure 12A:
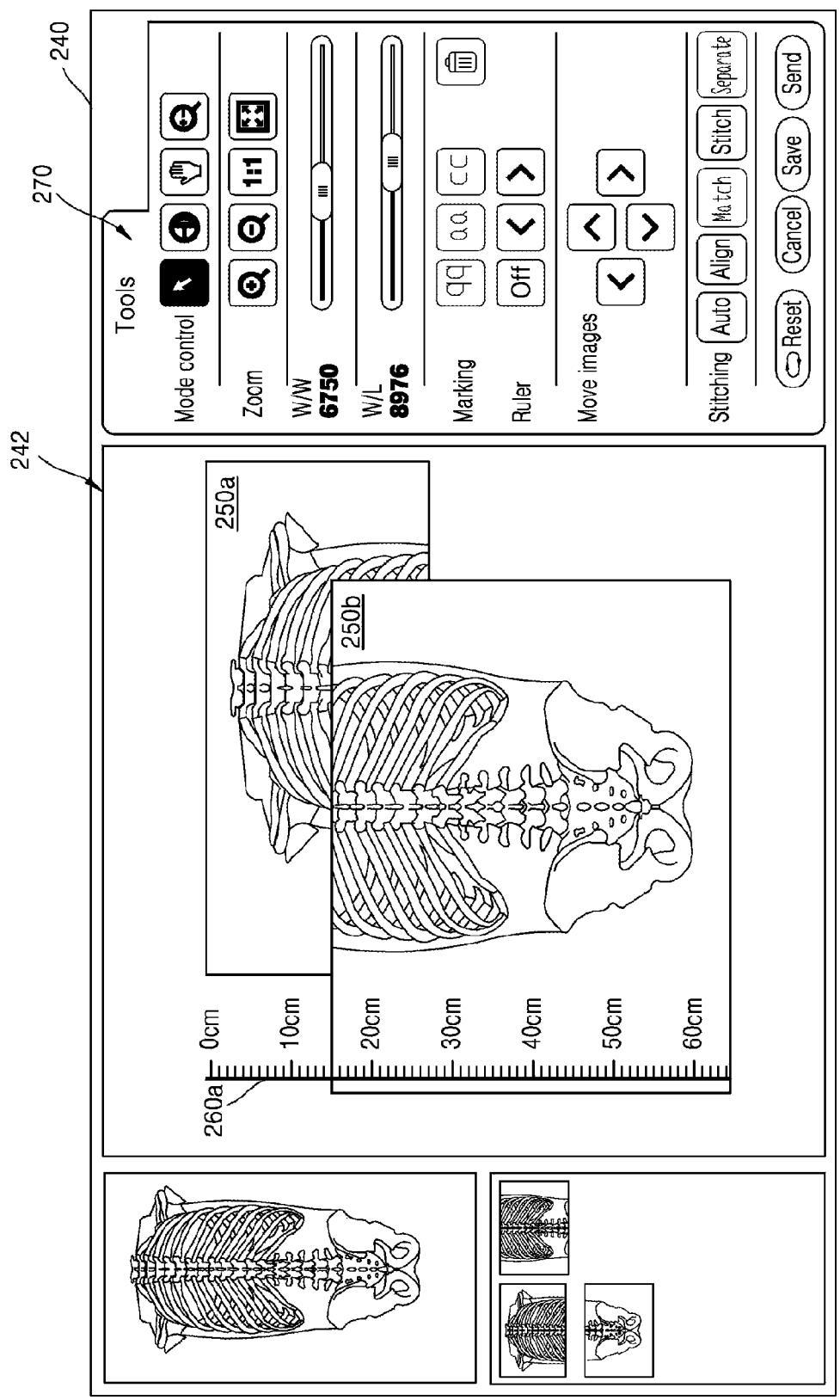
FIG. 12A is a diagram illustrating a display that displays a separate image which is moved horizontally.
Figure 12B:
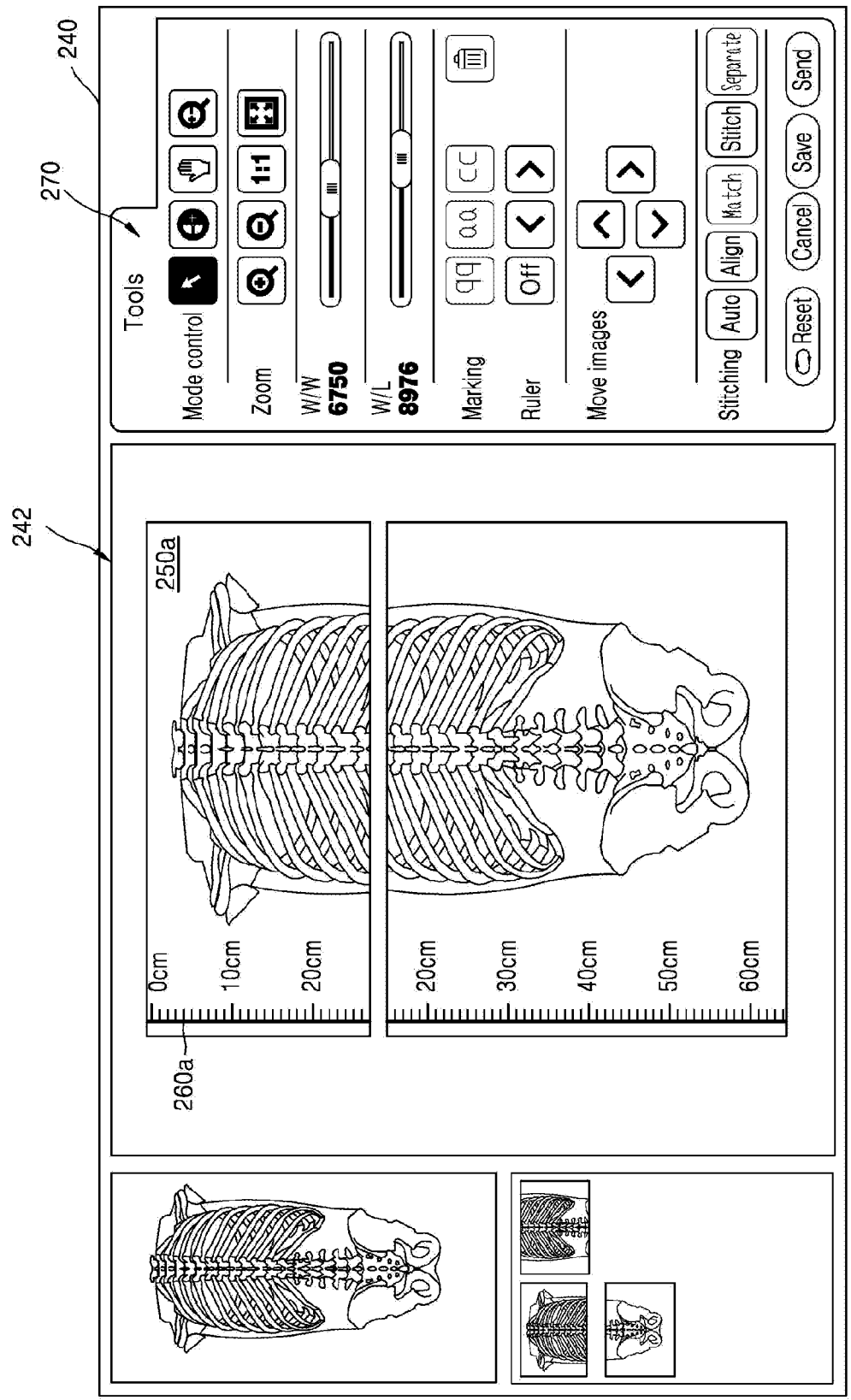
FIG. 12B is a diagram illustrating a display that displays a separate image which is moved vertically.

FIG. 12A is a diagram illustrating the display 240 that displays the first separate image 250a which is moved horizontally, and FIG. 12B is a diagram illustrating the display 240 that displays the first separate image 250a which is moved vertically.

In order to allow a user to easily compose the first through third separate images 250a, 250b, and 250c, when the user moves the first through third separate images 250a, 250b, and 250c horizontally or vertically, the medical image obtaining apparatus 200 according to an exemplary embodiment may adjust the first through third virtual rulers 260a, 260b, 260c displayed on the first through third separate images 250a, 250b, and 250c, respectively, according to the horizontal movement or the vertical movement of the first through third separate images 250a, 250b, and 250c.

Referring to FIG. 12A, when the controller 230 moves the first separate image 250a horizontally, the controller 230 may make the first virtual ruler 260a maintain the same axis as the other virtual rulers, i.e., the second and third virtual rulers 260b and 260c, without moving the first virtual ruler 260a displayed on the first separate image 250a. If the first virtual ruler 260a moves horizontally according to the horizontal movement of the first separate image 250a, the first virtual ruler 260a is not located on the same axis as the other virtual ruler, i.e., the second and third virtual rulers 260b and 260c, thereby causing inconvenience to a user when the user reads the scale of the first ruler 260a. Alternatively, the controller 230 may simultaneously move all the virtual rulers 260a, 260b, and 260c displayed on all of the separate images 250a, 250b, and 250c horizontally according to the horizontal movement of the first separate image 250a so that the virtual rulers 142a, 142b, and 142c may maintain the same axis.

Referring to FIG. 12B, when the controller 230 moves the first separate image 250a vertically, the controller 230 may move the first virtual ruler 260a displayed on the first separate image 250a vertically according to the vertical movement of the first separate image 250a because the scale of the first virtual ruler 260a displayed on the first separate image 250a varies if the first virtual ruler 260a does not move vertically according to the vertical movement of the first separate image 250a.

Figure 13:
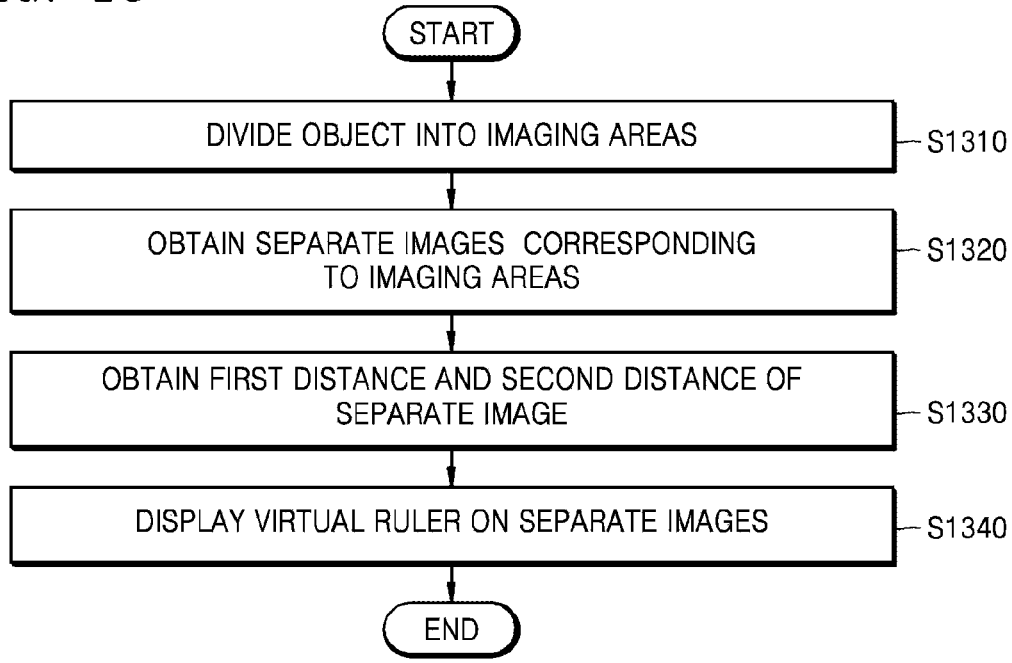
FIG. 13 is a flowchart illustrating a method of displaying a virtual ruler on the separate images of an object, according to an exemplary embodiment.

FIG. 13 is a flowchart illustrating a method of displaying a virtual ruler on each of a plurality of separate images of an object, according to an exemplary embodiment.

Referring to FIG. 13, the method of displaying a virtual ruler on each of a plurality of separate images of an object includes operations that are sequentially processed in the medical image obtaining apparatus 200 illustrated in FIG. 2. Accordingly, although not repeated below, the above description of the medical image obtaining apparatus 200 may apply to the method of FIG. 13.

In operation S1310, the medical image obtaining apparatus 200 divides an object into a plurality of imaging areas in a predetermined direction. The medical image obtaining apparatus 200 may include an X-ray image obtaining apparatus. The predetermined direction may include a vertical direction of the object.

In operation S1320, the medical image obtaining apparatus 200 obtains a plurality of separate images corresponding to the plurality of imaging areas. In detail, the image obtainer 210 of the medical image obtaining apparatus 200 may obtain a plurality of separate images corresponding to the plurality of imaging areas at locations corresponding to the plurality of imaging areas.

In operation S1330, the medical image obtaining apparatus 200 obtains a first distance from a predetermined reference point to a first side of each of the plurality of separate images and a second distance from the predetermined reference point to a second side of each of the plurality of separate images.

In operation S1340, the medical image obtaining apparatus 200 displays a virtual ruler, which indicates distance values between the obtained first distance of the separate image and the obtained second distance of the separate image, on each of the plurality of separate images.

Figure 14:
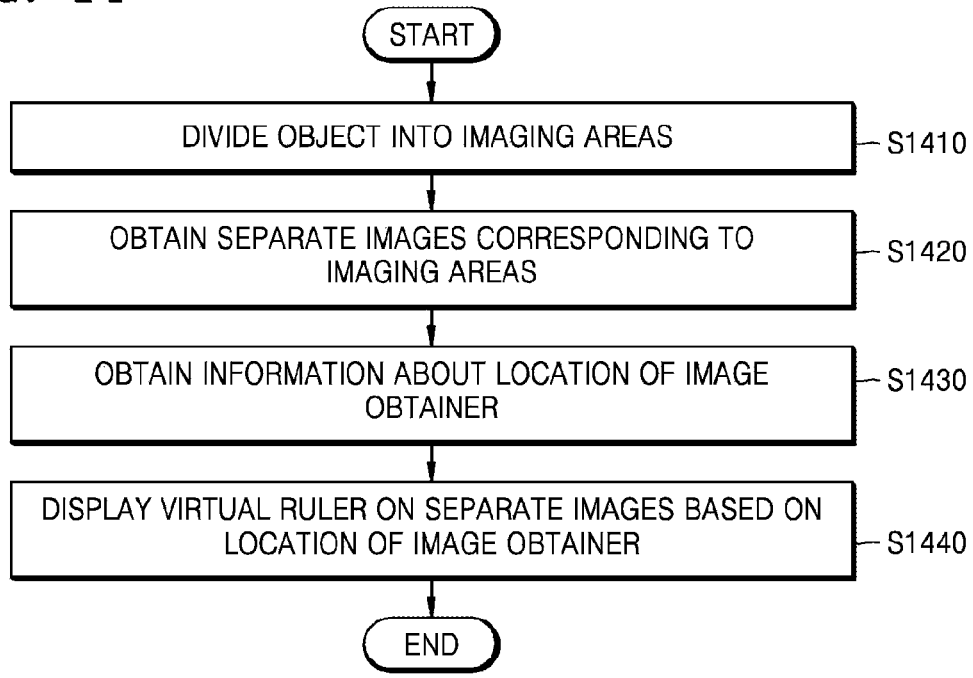
FIG. 14 is a flowchart illustrating a method of displaying a virtual ruler on the separate images of an object, according to an exemplary embodiment.

FIG. 14 is a flowchart illustrating a method of displaying a virtual ruler on each of a plurality of separate images of an object, according to an exemplary embodiment.

In operation S1410, the image obtainer 210 of the medical image obtaining apparatus 200 divides an object into a plurality of imaging areas in a predetermined direction.

In operation S1420, the image obtainer 210 obtains a plurality of separate images corresponding to the plurality of imaging areas.

In operation S1430, the medical image obtaining apparatus 200 obtains information about the location of the image obtainer 210.

In operation S1440, the medical image obtaining apparatus 200 displays a virtual ruler on each of the plurality of separate images based on the information about the location of the image obtainer 210. In detail, the medical image obtaining apparatus 200 may obtain first distance of the image obtainer 210 and second distance of the image obtainer 210, and may also display a virtual ruler, which indicates distance values between the first distance of the image obtainer 210 and the second distance of the image obtainer 210, on each of the plurality of separate images.

Alternatively, the medical image obtaining apparatus 200 may obtain first distance of each of the plurality of separate images and second distance of each of the plurality of separate images based on the information about the location of the image obtainer 210, and may display a virtual ruler, which indicates distance values between the first distance of each of the plurality of separate images and the second distance of each of the plurality of separate images, on each of the plurality of separate images.

Figure 15:
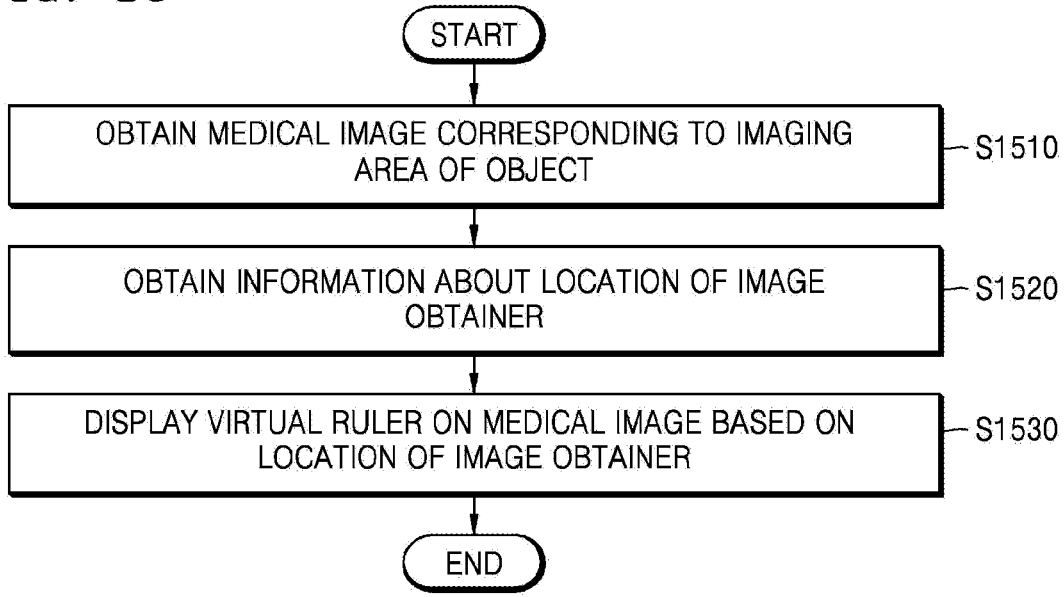
FIG. 15 is a flowchart illustrating a method of displaying a virtual ruler on the separate images of an object, according to an exemplary embodiment.

FIG. 15 is a flowchart illustrating a method of displaying a virtual ruler on each of a plurality of separate images of an object, according to an exemplary embodiment.

In operation S1510, the image obtainer 210 of the medical image obtaining apparatus 200 obtains a medical image corresponding to an imaging area of an object. The imaging area of the object may be set by a user.

In operation S1520, the medical image obtaining apparatus 200 obtains information about the location of the image obtainer 210.

In operation S1530, the medical image obtaining apparatus 200 displays a virtual ruler on the medical image based on the information about the location of the image obtainer 210. In detail, the medical image obtaining apparatus 200 may obtain first distance of the image obtainer 210 and second distance of the image obtainer 210, and may display a virtual ruler, which indicates distance values between the first distance of the image obtainer 210 and the second distance of the image obtainer 210, on the medical image.

Alternatively, the medical image obtaining apparatus 200 may obtain first distance of the medical image and second distance of the medical image based on the information about the location of the image obtainer 210, and may display a virtual ruler, which indicates distance values between the first distance of the medical image and the second distance of the medical image, on the medical image.

Figure 16:
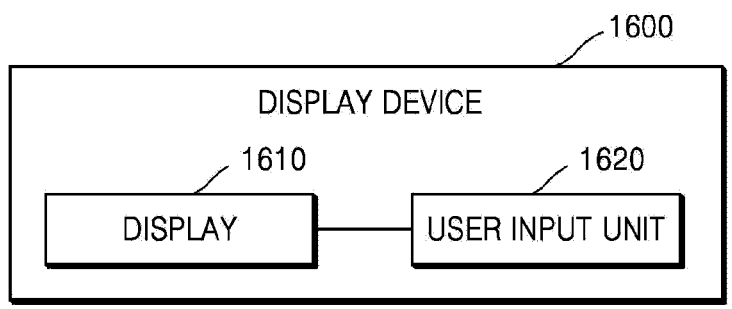
FIG. 16 is a block diagram of a display device according to an exemplary embodiment.

FIG. 16 is a block diagram of a display device 1600 according to an exemplary embodiment.

Referring to FIG. 16, the display device 1600 may include a display 1610 and a user input unit 1620.

The display 1610 may show predetermined information to a user. The display 1610 may include a monitor.

The user input unit 1620 may receive a user's input, and may include a mouse, a keyboard, or a trackball. If the display 1610 is a touch screen, the display 1610 may be used as the user input unit 1620.

The user input unit 1620 may receive a predetermined input from a user.

The display 1610 may display a plurality of separate images, on each of which a virtual ruler is shown, on a predetermined area of the display 1610. In addition, the display 1610 may display only the plurality of separate images without virtual rulers shown on the plurality of separate images on the predetermined area, based on an off input of a user, which is received through the user input unit 1620.

If an input which deactivates the off input or an on input is received from a user, the display 1610 may display virtual rulers deleted from the plurality of separate images again.

In addition, if an automatic composition input, a magnification input, a de-magnification input, a horizontal movement input, or a vertical movement input is received from a user, the display 1610 may control a plurality of separate images, which are being displayed, to correspond to a corresponding input. Since a corresponding description is provided above with reference to FIGS. 6 through 12, a detailed description is not repeated.

Although a case in which the display device 1600 of FIG. 16 displays a plurality of separate images of an object is described above, the above description of FIGS. 6 and 8 through 11 may apply to a single medical image on which a virtual ruler is displayed. That is, a medical image, such as an image of a lung or an image of a breast, rather than separate images for generating a composite image of an object, may also be displayed by the display device 1600 of FIG. 16.

Figure 17:
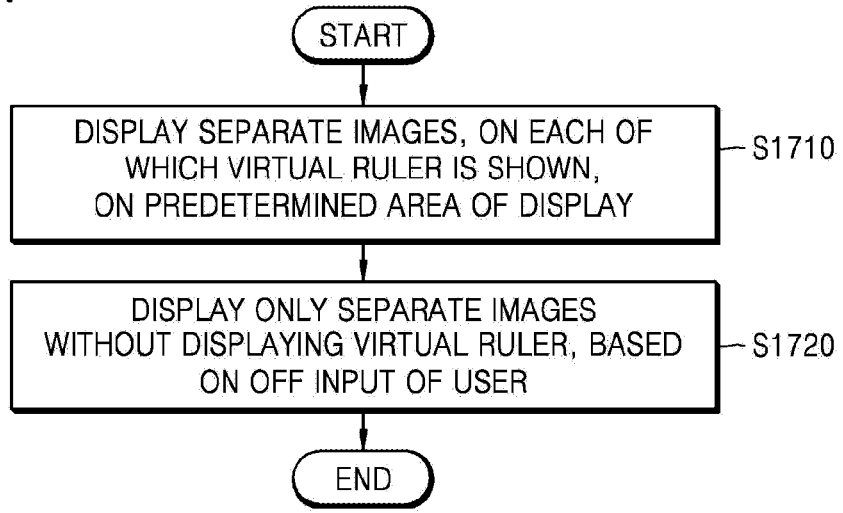
FIG. 17 is a flowchart illustrating a method of displaying a virtual ruler on the separate images of an object, according to an exemplary embodiment.

FIG. 17 is a flowchart illustrating a method of displaying a virtual ruler on each of a plurality of separate images of an object, according to an exemplary embodiment.

In operation S1710, the display device 1600 displays a plurality of separate images, on each of which a virtual ruler is shown, on a predetermined area of the display 1610.

In operation S1720, the display 1610 displays only the plurality of separate images without the virtual ruler shown on each of the plurality of separate images on the predetermined area, based on an off input of a user. The display 1610 may display the virtual ruler deleted from each of the plurality of separate images again according to an on input or an input which deactivates the off input that is received from a user.

The medical image obtaining apparatus 200 may include an X-ray imaging apparatus. The X-ray imaging apparatus may include an apparatus for generating X-rays and an apparatus for detecting X-rays and converting the X-rays into an image. For example, the X-ray imaging apparatus may be of a ceiling type, a U-arm type, or a C-arm type.

If the X-ray imaging apparatus is a ceiling type, the apparatus for generating X-rays is fixed in the ceiling.

If the X-ray imaging apparatus is a U-arm type, the apparatus for generating X-rays and the apparatus for detecting X-rays are fixed to an arm connected to an arm stand fixed to the ground.

The medical image obtaining apparatus 200 may include various types of X-ray imaging apparatuses.

Figure 18:
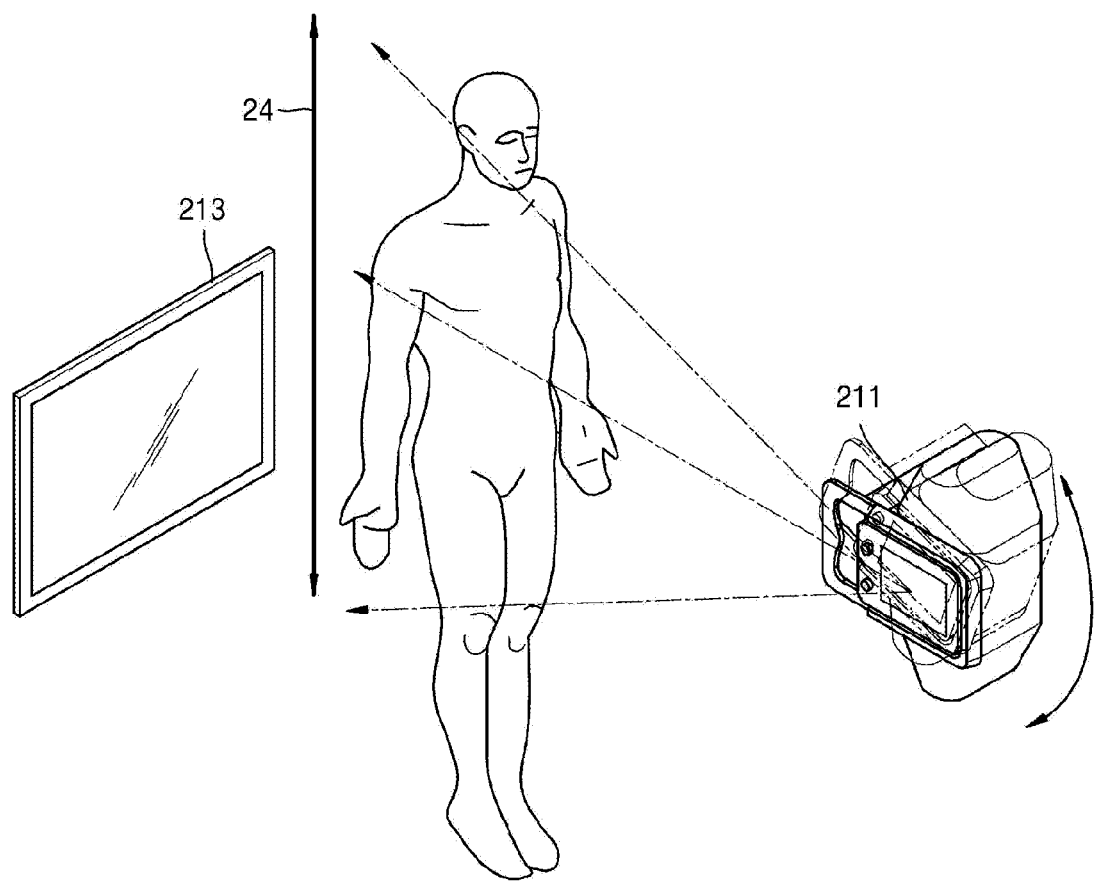
FIG. 18 is a diagram for describing an operation of a medical image obtaining apparatus to obtain an image of a portion of an object when an X-ray emitter is rotated, according to an exemplary embodiment.

FIG. 18 is a diagram for describing an operation of the medical image obtaining apparatus 200 to obtain an image of a portion of an object when an X-ray emitter 211 is rotated, according to an exemplary embodiment.

As illustrated in FIG. 18, an imaging area of an object to be imaged once by the medical image obtaining apparatus 200 may be limited to a portion of the object according to the image precision or target resolution of the medical image obtaining apparatus 200.

A direction of X-rays emitted towards the object may change as the X-ray emitter 211 is rotated to obtain the image of a portion of the object. An X-ray detector 213 may detect the X-rays that penetrate the portion of the object by moving in a predetermined direction when the X-ray emitter 211 is rotated.

The medical image obtaining apparatus 200 may obtain images of a plurality of portions of the object. The medical image obtaining apparatus 200 may divide the object into a plurality of portions in a predetermined direction, may rotate the X-ray emitter 211 by a rotation angle corresponding to each of the plurality of portions, and may move the X-ray detector 213 to a location corresponding to each of the plurality of portions to obtain the image of each of the plurality of portions. The images of the plurality of portions of the object that may be obtained may partially overlap one another.

As illustrated in FIG. 18, after obtaining a first image of a first portion of the object, the medical image obtaining apparatus 200 may rotate the X-ray emitter 211 and move the X-ray detector 213 in a predetermined direction 24. Then, the medical image obtaining apparatus 200 may obtain a second image of a second portion of the object. FIG. 18 illustrates an example in which images of two portions of the object are obtained. However, the number of images which may be obtained by the medical image obtaining apparatus 200 is not limited thereto.

For example, the medical image obtaining apparatus 200 may fix a location of the X-ray emitter 211 and change only a location of the X-ray detector 213, while obtaining the images of the plurality of portions of the object. The medical image obtaining apparatus 200 may image a large area of the object by performing an imaging process a plurality of times.

Figure 19:
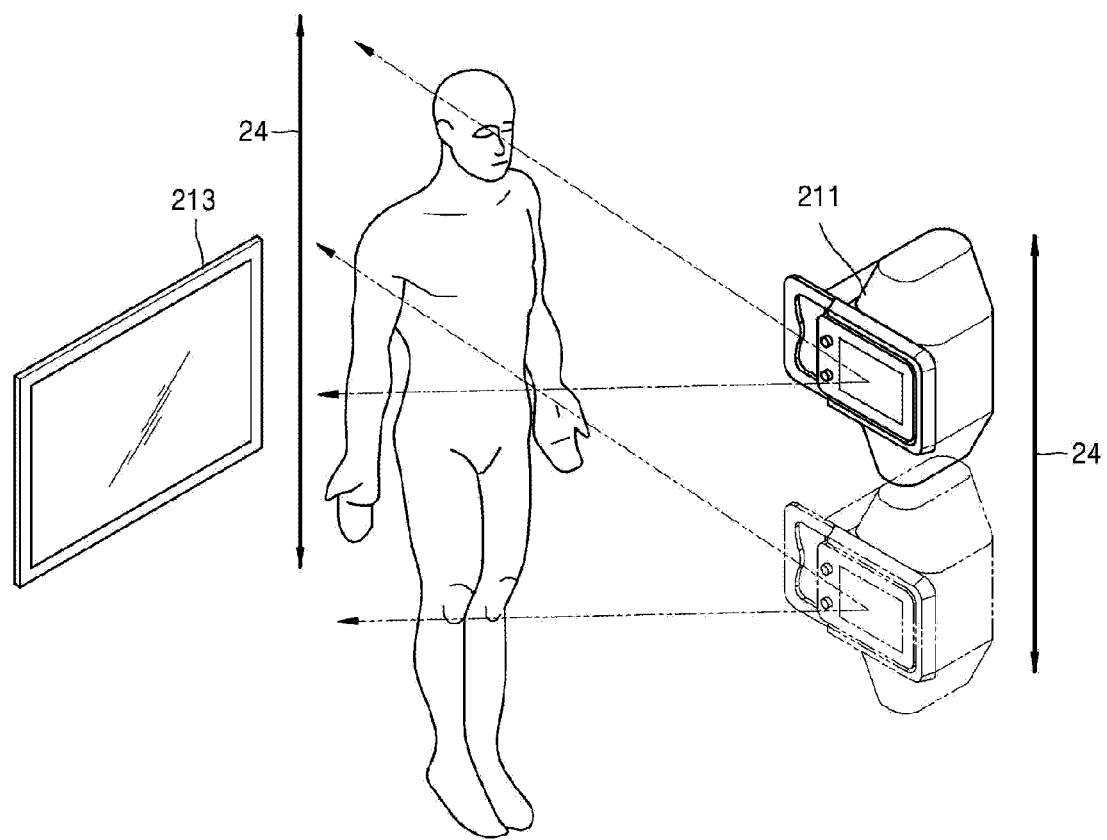
FIG. 19 is a diagram for describing an operation of a medical image obtaining apparatus to obtain an image of a portion of an object when an X-ray emitter is moved, according to an exemplary embodiment.

FIG. 19 is a diagram for describing an operation of the medical image obtaining apparatus 200 to obtain an image of a portion of an object when the X-ray emitter 211 is moved, according to an exemplary embodiment.

The medical image obtaining apparatus 200 may obtain an image of at least a portion of the object by a stepping method, as illustrated in FIG. 19. In the stepping method, an image is imaged by moving the X-ray emitter 211 together with the X-ray detector 213.

The X-ray emitter 211 may emit X-rays toward a portion of the object while moving to a location corresponding to the portion of the object in a predetermined direction, to obtain the image of the portion of the object. The X-ray detector 213 may detect the X-rays that penetrate the portion of the object by moving in a predetermined direction when the X-ray emitter 211 is moved.

The medical image obtaining apparatus 200 may obtain images of a plurality of portions of the object. The medical image obtaining apparatus 200 may divide the object into the plurality of portions in a predetermined direction and may move the X-ray emitter 211 and the X-ray detector 213 to a location corresponding to each of the plurality of portions to obtain the image of each of the plurality of portions. The images of the plurality of portions of the object that may be obtained may partially overlap one another.

The medical image obtaining apparatus 200 may obtain a first image of a first portion of the object and then may move the X-ray emitter 211 and the X-ray detector 213 in a predetermined direction 24, as illustrated in FIG. 19. Then, the medical image obtaining apparatus 200 may obtain a second image of a second portion of the object. Although FIG. 19 illustrates an example in which image of two portions of the object are obtained, the number of images which may be obtained by the medical image obtaining apparatus 200 is not limited thereto.

For example, as illustrated in FIG. 19, when the medical image obtaining apparatus 200 obtains the images of the plurality of portions of the object, the medical image obtaining apparatus 200 may maintain constant a distance from the X-ray emitter 211 to the X-ray detector 213 and an emission angle at which the X-rays are emitted to the object by the X-ray emitter 211, while changing only locations of the X-ray emitter 211 and the X-ray detector 213. The medical image obtaining apparatus 200 may image a large area of the object during an imaging process performed a plurality of times.

As illustrated in FIG. 1, when imaging images of a plurality of portions of an object according to a related art, a lead ruler 40 is placed beside the object 10 to indicate the location of each of images on each of the images, and the object 10 and the lead ruler 40 are imaged together. However, the placement of the lead ruler 40 beside the object results in waste of expenses and inconvenience in terms of utilization of an X-ray imaging space.

According to exemplary embodiments, there is provided a method of displaying a medical image whereby information of a location of each image may be accurately indicated in the image, without having to place the lead ruler 40 beside the object 10.

Figure 20A:
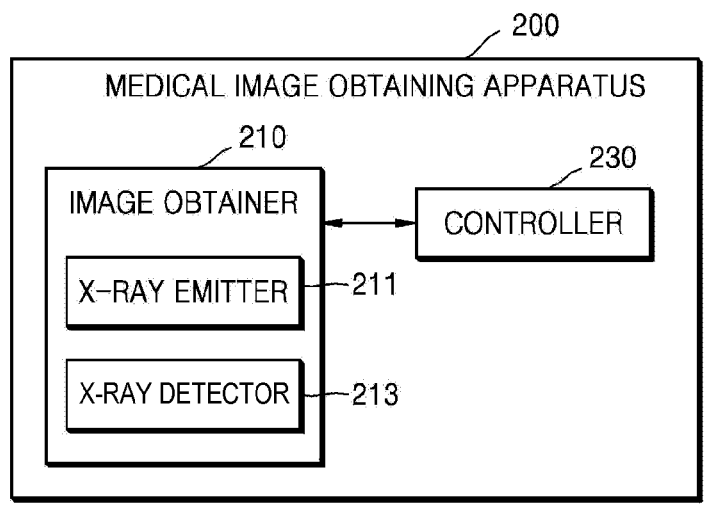
FIGS. 20A and 20B are block diagrams of a medical image obtaining apparatus according to exemplary embodiments.
Figure 20B:
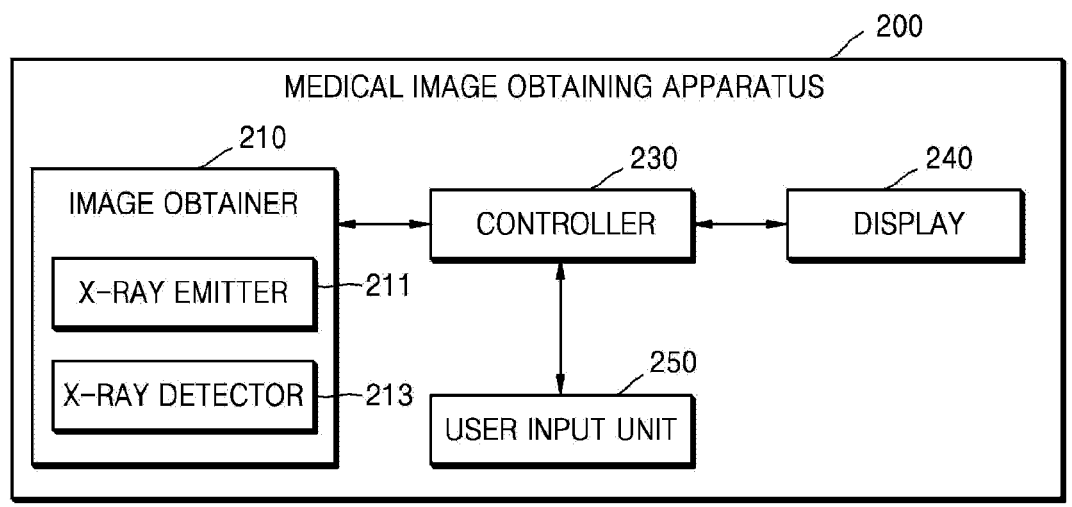

FIGS. 20A and 20B are block diagrams of a medical image obtaining apparatus 200, according to an exemplary embodiment.

Referring to FIG. 20A, the medical image obtaining apparatus 200 may include an image obtainer 210 and a controller 230.

The image obtainer 210 of FIG. 20A may correspond to the image obtainer 210 of FIG. 2. When one component corresponds to at least one other component, the component may perform a part or all functions of the corresponding component. The controller 230 of FIG. 20A may correspond to the controller 230 and the location obtainer 220 of FIG. 2.

The image obtainer 210 may include an X-ray emitter 211 for emitting X-rays to an object and an X-ray detector 213 for detecting X-rays penetrating the object. The image obtainer 210 may obtain an image of at least a portion of the object, based on the X-rays detected by the X-ray detector 213.

The X-ray emitter 211 may include a collimator which orients the X-rays emitted by the X-ray emitter 211. The X-rays generated by an X-ray tube pass through the collimator and become aligned in a specific direction or a spatial cross section of the X-rays becomes smaller. An opening area of the collimator may be adjusted according to a user's setting or a purpose of obtaining an image. The X-ray emitter 211 may adjust an opening size of the collimator by adjusting a blade of the collimator. For example, the opening area of the collimator may be adjusted according to the imaged parts of a body, or according to intensity or purpose of emitting the X-rays.

The image obtainer 210 may rotate the X-ray emitter 211 so that a direction of the X-rays emitted to the object is changed or may move the X-ray emitter 211 so that a position of the X-rays emitted to the object is changed, to obtain an image of a portion of an object.

For example, the image obtainer 210 may rotate the X-ray emitter 211 by a rotation angle corresponding to a portion of an object, so that the X-rays are emitted to the portion of the object. Alternatively, the image obtainer 210 may move the X-ray emitter 211 by a distance corresponding to a portion of an object, so that the X-rays are emitted to the portion of the object.

The image obtainer 210 may move the X-ray detector 213 in a predetermined direction to obtain an image of a portion of an object. The image obtainer 210 may move the X-ray detector 213 to a location corresponding to the portion of the object, to detect the X-rays that penetrate the portion of the object.

The image obtainer 210 may divide the object into a plurality of portions in a predetermined direction and obtain a plurality of images corresponding to the plurality of portions. The medical image obtaining apparatus 200 may rotate or move the X-ray emitter 211 and move the X-ray detector 213 in a predetermined direction to obtain the plurality of images.

The controller 230 may control an operation of the medical image obtaining apparatus 200. The controller 230 may control the image obtainer 210 to obtain an image of at least a portion of an object and may also control the X-ray emitter 211 and the X-ray detector 213. The controller 230 may be a microprocessor and may be realized as hardware, software, or a combination of hardware and software.

The controller 230 may generate a virtual ruler indicating information about a location of an image. The information about a location of an image may include information indicating which portion of the object the image belongs to, information about a distance from a reference point to a portion of the object displayed on the image, and/or information about a distance from a reference point to a first side of the image and information about a distance from the reference point to a second side of the image.

The controller 230 may obtain the information about a location of an image. The controller 230 may obtain the information about the distance from the reference point to the first side of the image and the distance from the reference point to the second side of the image. For example, the controller 230 may obtain a distance from the reference point to a first side of the X-ray detector 213 located at a position to obtain the image, as the distance from the reference point to the first side of the image. The controller 230 may obtain a distance from the reference point to a second side of the X-ray detector 213 located at the position to obtain the image as the distance from the reference point to the second side of the image.

The controller 230 may generate a virtual ruler based on at least one of a rotation angle of the X-ray emitter 211, a moved distance of the X-ray emitter 211, and a size of the X-ray detector 213.

The controller 230 may obtain information about at least one of a rotation angle of the X-ray emitter 211, a moved distance of the X-ray emitter 211, and a moved distance of the X-ray detector 213. Based on the obtained information, the controller 230 may obtain information about a distance from a reference point to a first side of an image and a distance from the reference point to a second side of an image. The controller 230 of the medical image obtaining apparatus 200 illustrated in FIG. 20A may perform a part or all of the functions performed by the location obtainer 220 of FIG. 3.

The controller 230 may generate a composite image by combining a plurality of images of a plurality of portions of an object.

As illustrated in FIG. 20B, the medical image obtaining apparatus 200 may further include one or more displays 240 and/or one or more user input units 250.

The display 240 of FIG. 20B may correspond to the display 1610 of FIG. 16 and the user input unit 250 of FIG. 20B may correspond to the user input unit 1620 of FIG. 16.

The display 240 may display the image generated by the medical image obtaining apparatus 200 and/or various information processed by the medical image obtaining apparatus 200 via a graphic user interface (GUI). The display 240 may provide a UI, for example, to allow the user to input data for controlling the medical image obtaining apparatus 200.

The display 240 may include at least one of a liquid crystal display, a thin film transistor-liquid crystal display, an organic light-emitting diode, a flexible display, a 3D display, and an electrophoretic display.

The display 240 may display a virtual ruler generated by the controller 230 on the image of the object. The display 240 may display a plurality of virtual rulers corresponding to a plurality of images on the plurality of images of the plurality of portions of the object. The display 240 may display a composite image generated by combining the plurality of images of the plurality of portions of the object.

The controller 230 may control the display 240 such that the virtual ruler is displayed on the image of the object. Based on a user's input received by the user input unit 250, the controller 230 may display only the image without the virtual ruler, change a location of the virtual ruler on the image, or change gaps of gradations included in the virtual ruler. The controller 230 may adjust a transparency of the virtual ruler based on a user's input.

The user input unit 250 is a device for receiving from a user data for controlling the medical image obtaining apparatus 200. For example, the user input unit 250 may include hardware components, such as a keypad, a touch panel, a touch screen, a track ball, and a jog switch. However, the exemplary embodiments are not limited thereto, and the user input unit 250 may further include any of various other input units including a voice recognition sensor, a gesture recognition sensor, a fingerprint recognition sensor, an iris recognition sensor, a depth sensor, a distance sensor, etc. When the display 240 is a touch screen including a touch pad having a layered structure, the display 240 may be used as the user input unit 250.

The user input unit 250 may receive a user's input for changing a reference point, which is a reference for the controller 230 to generate the virtual ruler. The controller 230 may generate the virtual ruler which indicates information about a distance from the reference point changed based on the user's input received from the user input unit 250 to the image.

The user input unit 250 may receive a user's input for changing a configuration with respect to the virtual ruler. For example, the controller 230 may control the display 240 based on the user's input such that only the image is displayed by deleting the virtual ruler on the image on which the virtual ruler is displayed, a location of the virtual ruler is changed on the image, or gaps of gradations included in the virtual ruler are changed The user input unit 250 may receive a user's input for selecting a method of combining the plurality of images of the plurality of portions of the object. For example, the user's input received by the user input unit 250 may include an input selecting one of a first method and a second method, wherein the first method is a method of combining the plurality of images based on virtual rulers corresponding to the plurality of images and a second method is a method of combining the plurality of images based on a result of analyzing overlapped areas of the plurality of images.

Figure 21:
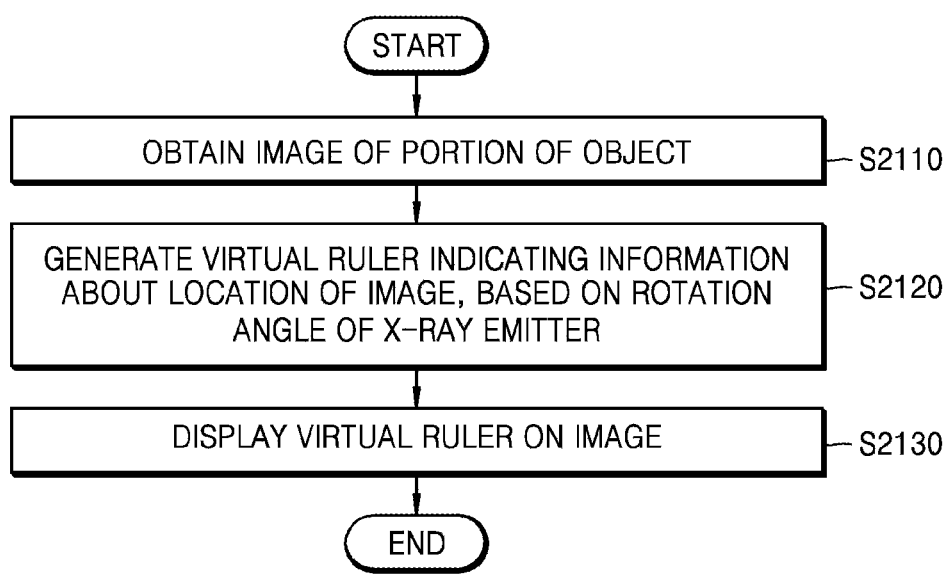
FIG. 21 is a flowchart of a method of generating a virtual ruler based on a rotation angle of an X-ray emitter and displaying the virtual ruler with an image, according to an exemplary embodiment.

FIG. 21 is a flowchart of a method of generating a virtual ruler based on a rotation angle of the X-ray emitter 211 and displaying the virtual ruler together with the image, according to exemplary embodiments.

Referring to FIG. 21, a method of displaying a medical image may include steps processed by the above-described medical image obtaining apparatus 200. Thus, the aspects described above with respect to the medical image obtaining apparatus 200 also apply to the method of displaying the medical image of FIG. 21.

In operation S2110, the medical image obtaining apparatus 200 may obtain an image of a portion of an object. The medical image obtaining apparatus 200 may obtain the image of the portion of the object based on detected X-rays by irradiating X-rays towards the object by using the X-ray emitter 211 and detecting the X-rays penetrating the object by using the X-ray detector 213. The X-ray emitter 211 may include a collimator and the irradiated X-rays may pass through the collimator.

The medical image obtaining apparatus 200 may rotate the X-ray emitter 211 to change a direction of the X-rays emitted to the object, to obtain the image of the portion of the object. The medical image obtaining apparatus 200 may rotate the X-ray emitter 211 by a rotation angle corresponding to the portion of the object, to irradiate the portion of the object with the X-rays.

The medical image obtaining apparatus 200 may move the X-ray detector 213 in a predetermined direction when the X-ray emitter 211 is rotated. The medical image obtaining apparatus 200 may move the X-ray detector 213 to a location corresponding to the portion of the object, to detect the X-rays that penetrate the portion of the object.

The medical image obtaining apparatus 200 may divide the object into a plurality of portions in a predetermined direction and obtain a plurality of images corresponding to the plurality of portions. The medical image obtaining apparatus 200 may rotate the X-ray emitter 211 such that a direction of the X-rays emitted to the object is changed and may move the X-ray detector 213 in a predetermined direction when the X-ray emitter 211 is rotated, to obtain the plurality of images.

For example, after obtaining a first image corresponding to a first portion of the object, the medical image obtaining apparatus 200 may rotate the X-ray emitter 211 by a predetermined angle and move the X-ray detector 213 in a predetermined direction in a predetermined distance. Then, the medical image obtaining apparatus 200 may obtain a second image of a second portion of the object.

The angle by which the X-ray emitter 211 is rotated and the distance by which the X-ray detector 213 is moved for next imaging operational segment may be predetermined as default values or may be configured by a user.

Alternatively, the medical image obtaining apparatus 200 may determine an imaging section based on a user's input for designating an imaging start area of the object and an imaging end area of the object. For example, when it is desired to obtain a plurality of images of areas between a first point and a second point of the object, the medical image obtaining apparatus 200 may receive a user's input for designating an imaging area including the first point as the imaging start area and designating an imaging area including the second point as the imaging end area. The medical image obtaining apparatus 200 may determine the areas between the imaging start area and the imaging end area as the imaging section. The medical image obtaining apparatus 200 may determine an angle by which the X-ray emitter 211 is rotated and a distance by which the X-ray detector 213 is moved for next imaging, based on the predetermined number of times of performing an imaging process with respect to the number of images in the imaging section.

In operation S2120, the medical image obtaining apparatus 200 may generate a virtual ruler indicating information about a location of the image obtained in operation S2110, based on the rotation angle of the X-ray emitter 211. The information about the location of the image may include information about a distance from a reference point to a portion of an object displayed on the image. In detail, the information about the location of the image may include information about a distance from the reference point to a first side of the image and a distance from the reference point to a second side of the image.

The distance from the reference point to the first side of the image and the distance from the reference point to the second side of the image may respectively correspond to a distance from the reference point to a first side of the X-ray detector 213 located at a position for obtaining the image and a distance from the reference point to a second side of the X-ray detector 213 located at a position for obtaining the image.

The reference point may correspond to the first side of the X-ray detector 213, when the X-ray detector 213 is located at a reference position. The reference position may be predetermined as a default value or may be determined by a user's input.

For example, when a plurality of images corresponding to a plurality of portions of an object are obtained by moving the X-ray detector 213 in a predetermined direction by a predetermined distance, the location of the X-ray detector 213 for obtaining a first image may be determined as the reference position of the X-ray detector 213.

Alternatively, the position of the X-ray detector 213 when the X-ray detector 213 is located at a highest position may be determined as the reference position of the X-ray detector 213. Alternatively, when the medical image obtaining apparatus 200 receives a user's input for designating an imaging start area and an imaging end area of the object, a position of the X-ray detector 213 for obtaining an image of the imaging start area of the object may be determined as the reference position of the X-ray detector 213.

The controller 230 of the medical image obtaining apparatus 200 may obtain a rotation angle of the X-ray emitter 211. The controller 230 may obtain an angle formed by a reference direction and a direction in which X-rays are emitted by the X-ray emitter 211 as the rotation angle of the X-ray emitter 211. The reference direction may be predetermined as a default value or may be determined by a user's input.

For example, when the X-rays emitted by the X-ray emitter 211 are vertically incident on the X-ray detector 213, the medical image obtaining apparatus 200 may configure the direction in which the X-rays are emitted as the reference direction. Alternatively, the medical image obtaining apparatus 200 may configure a direction perpendicular to a plane detecting the X-rays by the X-ray detector 213 as the reference direction.

The medical image obtaining apparatus 200 may generate the virtual ruler by further considering other information together with the rotation angle of the X-ray emitter 211.

For example, the medical image obtaining apparatus 200 may generate the virtual ruler by further considering an opening size of the collimator, a distance from an X-ray tube of the X-ray emitter 211 to the collimator, and a distance from the X-ray emitter 211 to the X-ray detector 213. The distance from the X-ray emitter 211 to the X-ray detector 213 may correspond to a distance from the X-ray tube of the X-ray emitter 211 to the X-ray detector 213.

For example, when an opening of the collimator that transmits the X-rays has a polygonal shape, the opening size of the collimator may denote a length of a predetermined side of a polygon. However, the exemplary embodiments are not limited thereto. When the opening of the collimator has a circular shape, the opening size of the collimator may denote a diameter or a radius of the opening of the collimator.

Figure 22:
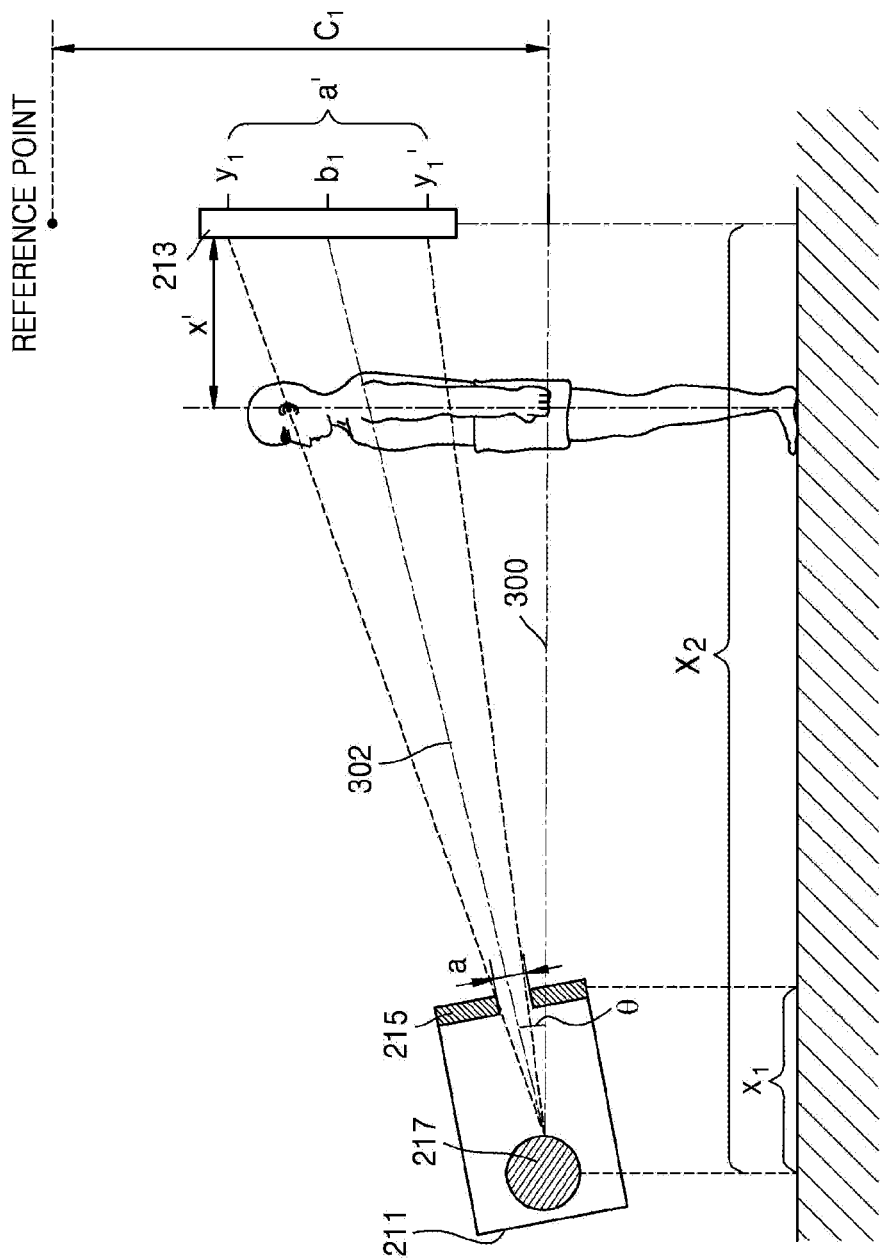
FIG. 22 is a diagram for describing a method of generating a virtual ruler based on a rotation angle of an X-ray emitter and an opening size of a collimator, according to an exemplary embodiment.

FIG. 22 is a diagram for describing a method of generating a virtual ruler based on a rotation angle of the X-ray emitter 211 and an opening size of the collimator, according to an exemplary embodiment.

As illustrated in FIG. 22, when a distance from a reference point to the X-rays emitted by the X-ray emitter 211 whose rotation angle is zero is c1, an angle by which the X-ray emitter 211 is rotated is Θ, a vertical distance of an opening of the collimator 215, i.e., a collimator opening size, is a, a distance from the X-ray tube 217 of the X-ray emitter 211 to the collimator 215 is x1, and a distance from the X-ray tube 217 of X-ray emitter 211 to the X-ray detector 213 is x2, a distance value a' from a first side of an image to a second side of the image may be obtained by using Equation 5, and a distance value b1 from the reference point to the center of the first and second sides of the image may be obtained by using Equation 6.

$$a'=a(x2/x1) \quad (5)$$

$$b1=c1-x2 \times \tan \Theta \quad (6)$$

The distance c1 from the reference point to the X-rays emitted by the X-ray emitter 211 whose rotation angle is zero may correspond to a distance from the reference point to a point corresponding to the height of the X-ray emitter 211, for example, a distance from the floor or ground level to approximately a central point of the X-ray tube 217 or a central point of the collimator opening. Alternatively, the distance c1 from the reference point to the X-rays emitted by the X-ray emitter 211 whose rotation angle is zero may correspond to a distance from the reference point to a central point of the X-ray detector 213 located at a position corresponding to the rotation angle of the X-ray emitter 211 when the rotation angle of the X-ray emitter 211 is zero.

The rotation angle Θ by which the X-ray emitter 211 is rotated may correspond to an angle formed by the reference axis 300 and the direction in which the X-rays are emitted from the X-ray emitter 211, for example, an axis extending through the central point of the collimator opening the X-ray emitter 211 is rotated. The angle Θ by which the X-ray emitter 211 is rotated may correspond to an angle formed by the X-rays emitted by the X-ray emitter 211 and a ground or a floor level. Alternatively, the angle Θ by which the X-ray emitter 211 is rotated may correspond to an angle formed by a straight line perpendicular to a plane in which the X-ray detector detects the X-rays and a segment connecting a central point of the X-ray emitter 211 and the X-ray detector 213.

A distance y1 from the reference point to the first side of the image may be obtained by using Equation 7 and a distance y1' from the reference point to the second side of the image may be obtained by using Equation 8.

$$y1=b1-(A'/2)=c1-x2 \times \tan \Theta -(a \times x2)/(2 \times x1) \quad (7)$$

$$y1'=b1+(a'/2)=c1-x2 \times \tan \Theta +(a \times x2)/(2 \times x1) \quad (8)$$

As illustrated in FIG. 22, when imaging the object, the object may be located apart from the X-ray detector 213 by a predetermined distance. Thus, when the distance from the reference point to the first side of the X-ray detector 213 and the distance from the reference point to the second side of the X-ray detector 213 are obtained as the information about the location of the image, a user may not entirely inaccurately measure an actual length of an object or an organ, etc., included in the object.

In this case, the medical image obtaining apparatus 200 may generate a virtual ruler indicating information about the location of the image by further using the distance x' that is from the object to the X-ray detector 213. To generate the virtual ruler by further considering the distance from the object to the X-ray detector 213, the method described above by referring to FIG. 5 may be used. Repeated descriptions will be omitted.

According to another example, the medical image obtaining apparatus 200 may generate the virtual ruler by further considering a size of the X-ray detector 213 and the distance from the X-ray emitter 211 to the X-ray detector 213.

Figure 23:
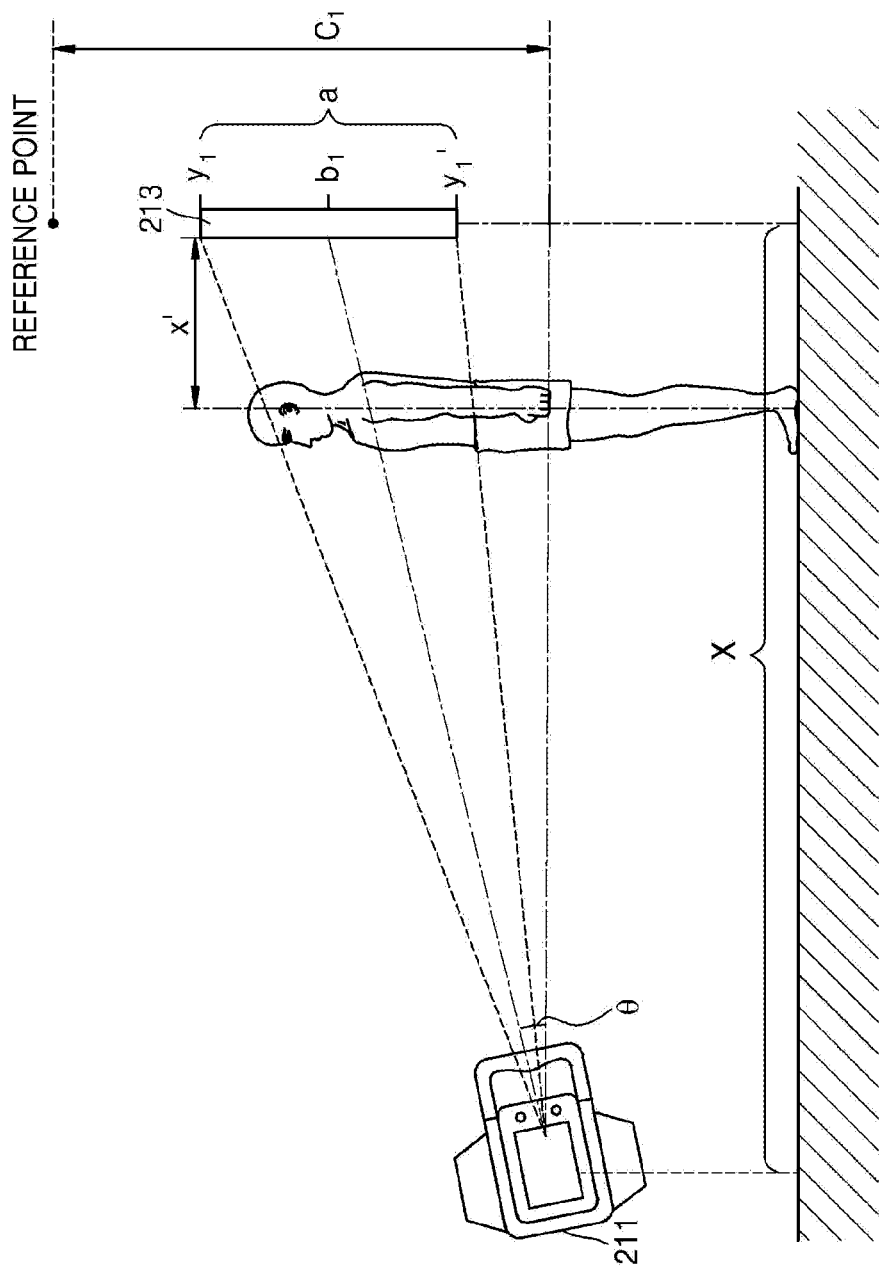
FIG. 23 is a diagram for describing a method of generating a virtual ruler based on a rotation angle of an X-ray emitter and a size of an X-ray detector, according to an exemplary embodiment.

FIG. 23 is a diagram for describing a method of generating a virtual ruler based on a rotation angle of the X-ray emitter 211 and a size of the X-ray detector 213.

As illustrated in FIG. 23, when a distance from the reference point to the X-rays emitted when the X-ray emitter 211 is not rotated is c1, an angle by which the X-ray emitter 211 is rotated is Θ, a distance from the X-ray emitter 211 to the X-ray detector 213 is x, and a vertical distance, i.e., length dimension, of the X-ray detector 213 is a, a distance b1 from the reference point to a center of the first and second sides of the image may be obtained by using Equation 9.

$$b1 = c1 - x \times \tan \Theta \qquad (9)$$

The distance y1 from the reference point to the first side of the image may be obtained by using Equation 10 and the distance y1' from the reference point to the second side of the image may be obtained by using Equation 11.

$$y1 = b1 - (a/2) = c1 - x \times \tan \Theta - (a/2) \qquad (10)$$

$$y1' = b1 + (a/2) = c1 - x \times \tan \Theta + (a/2) \qquad (11)$$

As illustrated in FIG. 23, when the object is imaged, the object may be located apart from the X-ray detector 213 by a predetermined distance. Thus, when the distance from the reference point to the first side of the X-ray detector 213 and the distance from the reference point to the second side of the X-ray detector 213 are obtained as the information about the location of the image, a user may not entirely inaccurately measure an actual length of an object or an organ, etc., included in the object.

In this case, the medical image obtaining apparatus 200 may generate a virtual ruler indicating information about a location of the image by further using the distance x' that is from the object to the X-ray detector 213. To generate the virtual ruler by further considering the distance from the object to the X-ray detector 213, the method described above by referring to FIG. 5 may be used. Repeated descriptions will be omitted.

The medical image obtaining apparatus 200 may obtain the information about the distance from the reference point to the first side of the image and the distance from the reference point to the second side of the image, according to the described method. The medical image obtaining apparatus 200 may generate the virtual ruler indicating the distance from the reference point to the first side of the image and the distance from the reference point to the second side of the image.

The medical image obtaining apparatus 200 may generate the virtual ruler indicating values between the distance from the reference point to the first side of the image and the distance from the reference point to the second side of the image. The medical image obtaining apparatus 200 may generate the virtual ruler including gradations which indicate the values between the distance from the reference point to the first side of the image and the distance from the reference point to the second side of the image as predetermined gaps, e.g., intervals or measurement points.

For example, the medical image obtaining apparatus 200 may obtain an actual length of each pixel in an image by using the number of pixels in a predetermined direction of the image. The medical image obtaining apparatus 200 may obtain the actual length of each pixel by dividing the distance values between the distance from the reference point to the first side of the image and the distance from the reference point to the second side of the image, by the number of pixels.

The medical image obtaining apparatus 200 may generate the virtual ruler indicating values between the distance from the reference point to the first side of the image and the distance from the reference point to the second side of the image by using the distance from the reference point to the first side of the image and the actual distance of each pixel.

According to another example, the medical image obtaining apparatus 200 may divide the image into a plurality of portions in a predetermined direction and obtain actual distances of the portions on the image by using the number of the plurality of portions. The medical image obtaining apparatus 200 may obtain the actual distances of the portions on the image by dividing the distance values between the distance from the reference point to the first side of the image and the distance from the reference point to the second side of the image, by the number of the plurality of portions.

The medical image obtaining apparatus 200 may generate the virtual ruler on which a distance value corresponding to a point at which the plurality of portions are divided is displayed at the point where the plurality of portions are divided, by using the distance from the reference point to the first side of the image and the actual distances of the portions.

FIGS. 22 and 23 illustrate an example in which the medical image obtaining apparatus 200 obtains information about the distance from the reference point to the first side of a single image and the distance from the reference point to the second side of the single image. However, exemplary embodiments are not limited to the example illustrated in FIGS. 22 and 23.

The medical image obtaining apparatus 200 may obtain information about a location of each of a plurality of images, based on a rotation angle by which the X-ray emitter 211 is rotated to obtain each of the plurality of images corresponding to a plurality of portions of an object. The medical image obtaining apparatus 200 may generate a plurality of virtual rulers based on information about a location of each of the plurality of images. Each of the plurality of virtual rulers may indicate information about a distance from a reference point to a first side of a corresponding image and a distance from the reference point to a second side of the corresponding image.

The medical image obtaining apparatus 200 may change a reference point, which is a reference for generating the virtual ruler, based on a user's input. The medical image obtaining apparatus 20 may receive the user's input for changing the reference point. The medical image obtaining apparatus 200 may generate the virtual ruler indicating information about a distance from the reference point changed based on the user's input to the image.

In operation S2130, the medical image obtaining apparatus 200 may display the virtual ruler on the image obtained in operation S2110.

Detailed exemplary embodiments with respect to the display of the virtual ruler on the image may correspond to the exemplary embodiments described by referring to FIGS. 9 through 12B. Repeated descriptions will be omitted.

According to a method of a related art of imaging and displaying a lead ruler together with an object, it is almost impossible to delete the lead ruler on the image and display only the image about the object, without corrupting the useful image data of the object. For example, complex and computation-intense algorithms are needed to completely remove the image data of the ruler, which has been imaged with the object, from the useful object image data, and this processing is often unavailable in clinical imaging. Thus, when the lead ruler covers the object, a user may have difficulties in accurately identifying the object. Also, according to the method of the related art, when a user enlarges an image, the lead ruler displayed on the image goes outside a display portion, and thus, the user may have difficulties in identifying the image about the lead ruler.

However, according to exemplary embodiments, the virtual ruler is not imaged together with the object, and thus, the virtual ruler may be easily deleted from the image and easily edited separately from the image.

For example, based on a user's input, the medical image obtaining apparatus 200 may display only the image without the virtual ruler, change a location of the virtual ruler on the image, or display the image by changing gaps of gradations included in the virtual ruler. Alternatively, the medical image obtaining apparatus 200 may adjust a transparency of the virtual ruler based on a user's input.

The medical image obtaining apparatus 200 may change a reference point, which is a reference for generating the virtual ruler, based on a user's input. The medical image obtaining apparatus 200 may receive the user's input for changing the reference point. The medical image obtaining apparatus 200 may renew and display the virtual ruler such that the virtual ruler indicates information about a distance from the reference point changed based on the user's input to the image.

As illustrated in FIG. 19, the medical image obtaining apparatus 200 may irradiate a portion of an object with X-rays and detect the X-rays that penetrate the portion of the object by moving the X-ray emitter 211 and the X-ray detector 213 in a predetermined direction to a location corresponding to the portion of the object, to obtain an image of the portion of the object.

Figure 24:
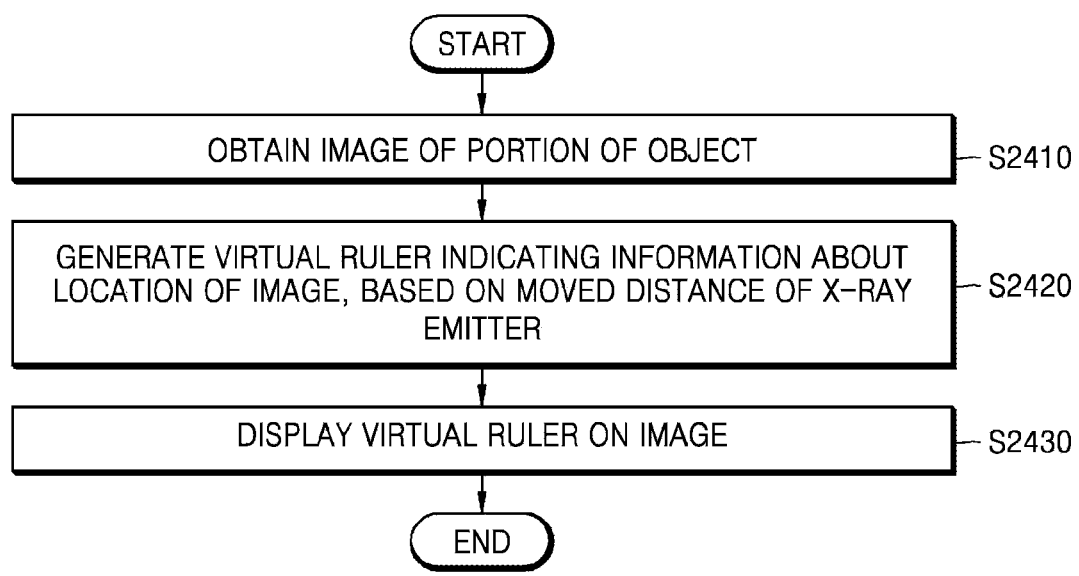
FIG. 24 is a flowchart of a method of generating a virtual ruler based on a moved distance of an X-ray emitter and displaying the virtual ruler with an image, according to an exemplary embodiment.

FIG. 24 is a flowchart of a method of generating a virtual ruler based on a moved distance of the X-ray emitter 211 and displaying the virtual ruler with an image, according to an exemplary embodiment.

Referring to FIG. 24, the method of displaying the medical image may include steps processed by the medical image obtaining apparatus 200. Thus, the descriptions with respect to the medical image obtaining apparatus 200 apply to the method of displaying the medical image of FIG. 24.

The medical image obtaining apparatus 200 may obtain an image of a portion of an object in operation S2410. The medical image obtaining apparatus 200 may obtain the image of the portion of the object based on detected X-rays by irradiating X-rays towards the object by using the X-ray emitter 211 and detecting the X-rays that penetrate the object by using the X-ray detector 213.

The medical image obtaining apparatus 200 may move the X-ray emitter 211 in a predetermined direction so that a location at which the X-ray emitter 211 emits the X-rays to the object is changed, to obtain the image of the portion of the object. The medical image obtaining apparatus 200 may move the X-ray emitter 211 by a predetermined distance corresponding to the portion of the object so that the X-rays are emitted toward the portion of the object.

The medical image obtaining apparatus 200 may move the X-ray detector 213 in a predetermined direction as the X-ray emitter 211 is moved. The medical image obtaining apparatus 200 may move the X-ray detector 213 to a location corresponding to the portion of the object so that the X-rays that penetrate the portion of the object are detected.

The medical image obtaining apparatus 200 may divide the object into a plurality of portions in a predetermined direction and obtain a plurality of images corresponding to the plurality of portions. The medical image obtaining apparatus 200 may move the X-ray emitter 211 in a predetermined direction so that a location of the object to which the X-rays are emitted is changed and move the X-ray detector 213 in a predetermined direction when the X-ray emitter 211 is moved, to obtain the plurality of images.

For example, the medical image obtaining apparatus 200 may obtain a first image corresponding to a first portion of the object and then may move the X-ray emitter 211 in a predetermined direction by a predetermined distance and move the X-ray detector 213 in a predetermined direction by a predetermined distance. Then, the medical image obtaining apparatus 200 may obtain a second image of a second portion of the object.

The distance moved by the X-ray emitter 211 and the X-ray detector 213 for next imaging may be predetermined as default values or configured by a user.

Alternatively, the medical image obtaining apparatus 200 may determine an imaging section based on a user's input for designating an imaging start area of an object and an imaging end area of the object. For example, when it is desired to obtain a plurality of images of areas between a first point to a second point of the object, the medical image obtaining apparatus 200 may receive the user's input for designating an imaging area including the first point as the imaging start area and an imaging area including the second point as the imaging end area. The medical image obtaining apparatus 200 may determine the areas between the imaging start area and the imaging end area as the imaging section. The medical image obtaining apparatus 200 may determine the distance moved by the X-ray emitter 211 and the X-ray detector 213 for next imaging, based on the predetermined number of times of performing an imaging process with respect to the number of images in the imaging section.

In operation S2420, the medical image obtaining apparatus 200 may generate a virtual ruler indicating information about a location of the image obtained in operation S2410, based on the moved distance of the X-ray emitter 211. The moved distance of the X-ray emitter 211 may denote a distance by which the X-ray emitter 211 is moved for next imaging when the medical image obtaining apparatus 200 performs the imaging process a plurality of times.

The information about a location of an image may include information about a distance from a reference point to a portion of the object displayed on the image. In detail, the information about a location of an image may include information about a distance from the reference point to a first side of the image and a distance from the reference point to a second side of the image.

The distance from the reference point to the first side of the image and the distance from the reference point to the second side of the image may respectively correspond to a distance from the reference point to a first side of the X-ray detector 213 at a location for obtaining the image and a distance from the reference point to a second side of the X-ray detector 213 at the location for obtaining the image.

The reference point may correspond to the first side of the X-ray detector 213 when the X-ray detector 213 is located at a reference position. The reference position may be predetermined as a default value or configured by a user's input.

For example, when the plurality of images corresponding to the plurality of portions of the object are obtained by moving the X-ray detector 213 in a predetermined direction by a predetermined distance, the location of the X-ray detector 213 for obtaining a first image may be determined as the reference position of the X-ray detector 213.

Alternatively, when the X-ray detector 213 is located at a highest position, the highest position may be determined as the reference position of the X-ray detector 213. Alternatively, when the medical image obtaining apparatus 200 receives the user's input for designating the imaging start area and the imaging end area of the object, the location of the X-ray detector 213 for obtaining an image of the imaging start area may be determined as the reference position thereof.

The medical image obtaining apparatus 200 may generate the virtual ruler by further considering other information together with the moved distance of the X-ray emitter 211.

For example, the medical image obtaining apparatus 200 may generate the virtual ruler by further considering a size of the X-ray detector 213. The size of the X-ray detector 213 may denote a length of a predetermined side of a polygon when the X-ray detector 213 has a polygonal shape.

Figure 25:
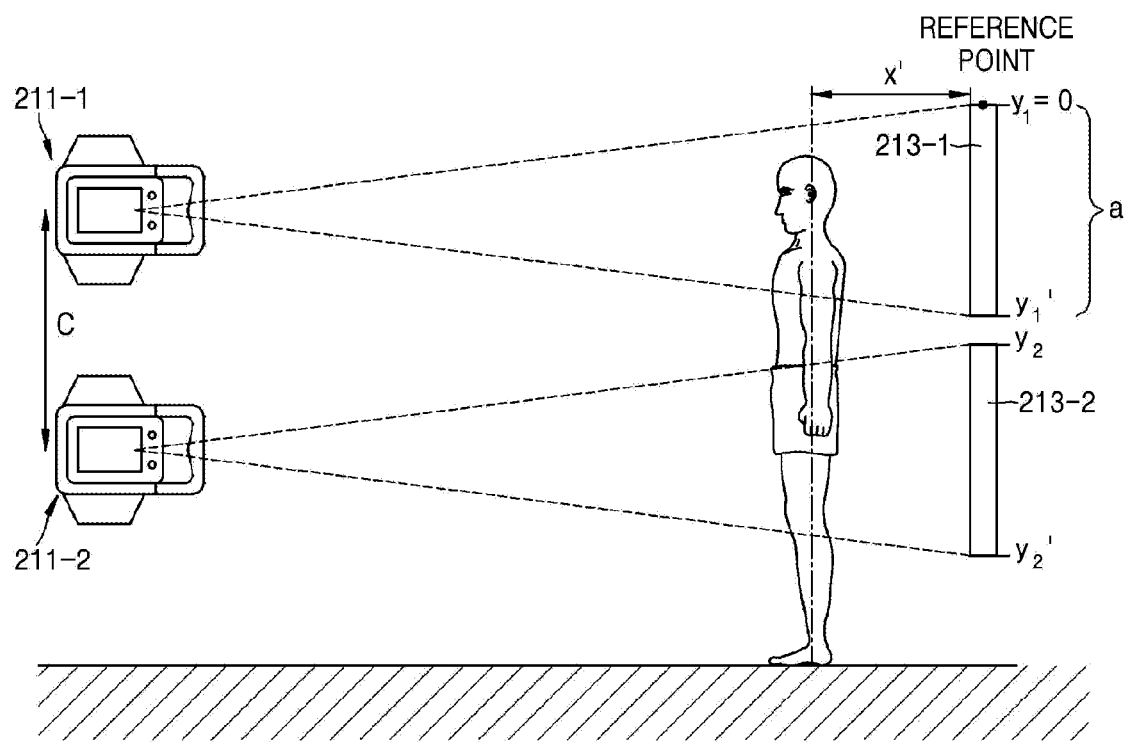
FIG. 25 is a diagram for describing a method of generating a virtual ruler based on a moved distance of an X-ray emitter, according to an exemplary embodiment.

FIG. 25 is a diagram for describing a method of generating a virtual ruler based on a moved distance of an X-ray emitter 211-1 and a size of an X-ray detector 213-1, according to an exemplary embodiment. FIG. 25 illustrates an example in which the medical image obtaining apparatus 200 obtains a first image of a first portion of an object and a second image of a second portion of the object.

As illustrated in FIG. 25, the medical image obtaining apparatus 200 may obtain the first image of the first portion of the object by using the X-ray emitter at a location 211-1, i.e., a first emitter location, and the X-ray detector at a location 213-1, i.e., a first detector location, and then move the X-ray emitter 211 and the X-ray detector 213 in a predetermined direction by a predetermined distance. Then, the medical image obtaining apparatus 200 may obtain the second image of the second portion of the object by using the X-ray emitter at a location 211-2, i.e., a second emitter location, and the X-ray detector at a location 213-2, i.e., a second detector location.

When a first side of the X-ray detector 213 for obtaining the first image is determined as the reference point, the moved distance of the X-ray emitter 211 for obtaining the second image after obtaining the first image is c and a vertical distance of the X-ray detector 213 is a, a distance y1 from the reference point to a first side of the first image may be zero and a distance y1' from the reference point to a second side of the first image may be a.

A distance y2 from the reference point to a first side of the second image may be obtained by using Equation 12 and a distance y2' from the reference point to a second side of the second image may be obtained by using Equation 13.

$$y2 = y1 + c = c \quad (12)$$

$$y2' = y1' + c = a + c \quad (13)$$

FIG. 25 illustrates an example in which the first side of the X-ray detector at a location 213-1 for obtaining the first image is determined as the reference point. However, exemplary embodiments are not limited to the example of FIG. 25. For example, when a plurality of images of a plurality of portions of the object are obtained, the medical image obtaining apparatus 200 may determine the first side of the X-ray detector 213 at the location for obtaining the first image as the reference point. The reference point may be predetermined as a default value or may be configured by a user. The medical image obtaining apparatus 200 may obtain the reference point by measuring a distance from the reference point to a first side of the first image or obtain the reference point based on a user's input.

As illustrated in FIG. 25, when the object is imaged, the object may be located apart from the X-ray detector 213 by a predetermined distance. Thus, when the distance from the reference point to the first side of the X-ray detector 213 and the distance from the reference point to the second side of the X-ray detector 213 are obtained as information about a location of the image, the user may not entirely inaccurately measure an actual length of an object or an organ, etc. in the object.

In this case, the medical image obtaining apparatus 200 may generate a virtual ruler indicating information about a location of the object by further using a distance x' from the object to the X-ray detector 213. To generate the virtual ruler by further considering the distance from the object to the X-ray detector 213, the method described by referring to FIG. 5 may be used. Repeated descriptions will be omitted.

The medical image obtaining apparatus 200 may obtain the information about the distance from the reference point to the first side of the image and the distance from the reference point to the second side of the image according to the described method. The medical image obtaining apparatus 200 may generate the virtual ruler indicating the distance from the reference point to the first side of the image and the distance from the reference point to the second side of the image.

The medical image obtaining apparatus 200 may generate the virtual ruler indicating values between the distance from the reference point to the first side of the image and the distance from the reference point to the second side of the image. The medical image obtaining apparatus 200 may generate the virtual ruler including gradations which indicate the values between the distance from the reference point to the first side of the image and the distance from the reference point to the second side of the image as predetermined gaps.

For example, the medical image obtaining apparatus 200 may obtain an actual distance of each pixel on the image by using the number of pixels in a predetermined direction of the image. The medical image obtaining apparatus 200 may obtain the actual distance of each pixel by dividing the distance values between the distance from the reference point to the first side of the image and the distance from the reference point to the second side of the image by the number of pixels.

The medical image obtaining apparatus 200 may generate the virtual ruler which indicates the distance values between the distance from the reference point to the first side of the image and the distance from the reference point to the second side of the image by using the distance from the reference point to the first side of the image and the actual distance of each pixel.

According to another example, the medical image obtaining apparatus 200 may divide the image into a plurality of portions in a predetermined direction and obtain actual distances of the portions of the image by using the number of the plurality of portions. The medical image obtaining apparatus 200 may obtain the actual distances of the portions of the image by dividing the distance values between the distance from the reference point to the first side of the image and the distance from the reference point to the second side of the image by the number of the plurality of portions.

The medical image obtaining apparatus 200 may generate the virtual ruler on which a distance value corresponding to a point where the plurality of portions are divided is displayed on the point where the plurality of portions are divided by using the distance from the reference point to the first side of the image and the actual distances of the portions.

The medical image obtaining apparatus 200 may change the reference point, which is a reference for generating the virtual ruler, based on a user's input. The medical image obtaining apparatus 200 may receive the user's input for changing the reference point. The medical image obtaining apparatus 200 may generate the virtual ruler indicating information about a distance from the reference point changed based on the user's input to the image.

In operation S2430, the medical image obtaining apparatus 200 may display the virtual ruler on the image obtained in operation S2110.

Detailed exemplary embodiments with respect to the display of the virtual ruler on the image may correspond to the exemplary embodiments described with reference to FIGS. 9 through 12B. Repeated descriptions will be omitted.

Figure 26:
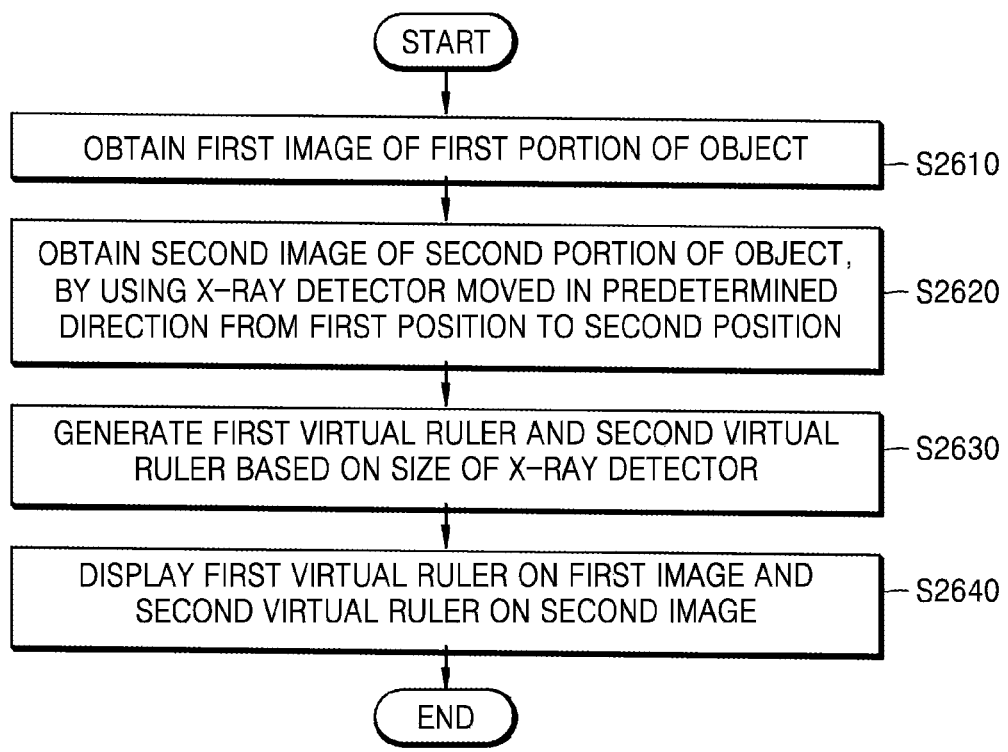
FIG. 26 is a flowchart of a method of generating a virtual ruler based on a size of an X-ray detector and displaying the virtual ruler with an image, according to an exemplary embodiment.

FIG. 26 is a flowchart of a method of generating a virtual ruler based on a size of the X-ray detector 213 and displaying the virtual ruler with an image, according to an exemplary embodiment.

Referring to FIG. 26, the method of displaying the medical image may include steps performed by the medical image obtaining apparatus 200. Thus, the descriptions with respect to the medical image obtaining apparatus 200 apply to the method of displaying the medical image of FIG. 26.

In operation S2610, the medical image obtaining apparatus 200 may obtain a first image of a first portion of the object based on detected X-rays by irradiating X-rays towards the object by using the X-ray emitter 211 and detecting the X-rays that penetrate the object by using the X-ray detector 213 located at a first position.

In operation S2620, the medical image obtaining apparatus 200 may obtain a second image of a second portion of the object.

The medical image obtaining apparatus 200 may change a direction of X-rays so that the X-rays are emitted to a second portion of the object by rotating the X-ray emitter 211 by a predetermined angle, or may change a location of the X-rays so that the X-rays are emitted to the second portion of the object by moving the X-ray emitter 211 in a predetermined direction by a predetermined distance. The angle by which the X-ray emitter 211 is rotated or the distance by which the X-ray emitter 211 is moved for next imaging may be predetermined as default values or configured by a user's input.

The medical image obtaining apparatus 200 may move the X-ray detector 213 from the first position to a second position in a predetermined direction so that the X-rays that penetrate the second portion of the object are detected. Then, the medical image obtaining apparatus 200 may obtain the second image of the second portion of the object based on detected X-rays by irradiating the X-rays toward the object by using the X-ray emitter 211 and detecting the X-rays that penetrate the object by using the X-ray detector 213 located at the second position. The distance moved by the X-ray detector 213 for next imaging may be predetermined as a default value or configured by a user.

The medical image obtaining apparatus 200 may determine an imaging section based on a user's input for designating an imaging start area of the object and an imaging end area of the object. For example, when it is intended to obtain a plurality of images of areas between a first point and a second point of the object, the medical image obtaining apparatus 200 may receive a user's input for designating an imaging area including the first point as the imaging start area and designating an imaging area including the second point as the imaging end area. The medical image obtaining apparatus 200 may determine the areas between the imaging start area and the imaging end area as the imaging section. The medical image obtaining apparatus 200 may determine a distance by which the X-ray detector 213 is moved for next imaging based on the predetermined number of times of imaging with respect to the number of images in the imaging section.

In operation S2630, the medical image obtaining apparatus 200 may generate a first virtual ruler indicating information about a location of the first image and a second virtual ruler indicating information about a location of the second image based on a size of the X-ray detector 213.

When the X-ray detector 213 has a polygonal shape, the size of the X-ray detector 213 may denote a length of a predetermined side of a polygon.

The information about a location of an image may include information about a distance from a reference point to a portion of the object displayed on the image. In detail, the information about a location of an image may include information about a distance from the reference point to a first side of the image and a distance from the reference point to a second side of the image. For example, the first virtual ruler may indicate information about a distance from the reference point to a first side of the first image and a distance from the reference point to a second side of the first image, and the second virtual ruler may indicate information about a distance from the reference point to a first side of the second image and a distance from the reference point to a second side of the second image.

The distance from the reference point to the first side of the image and the distance from the reference point to the second side of the image may respectively correspond to a distance from the reference point to a first side of the X-ray detector 213 at a location for obtaining the image and a distance from the reference point to a second side of the X-ray detector 213 at the location for obtaining the image.

The reference point may correspond to the first side of the X-ray detector 213, when the X-ray detector 213 is located at a reference position. The reference position may be predetermined as a default value or configured by a user's input.

For example, when a plurality of images corresponding to a plurality of portions of the object are obtained by moving the X-ray detector 213 in a predetermined direction by a predetermined distance, the location of the X-ray detector 213 for obtaining a first image may be determined as the reference position of the X-ray detector 213.

Alternatively, when the X-ray detector 213 is at a highest position, the highest position may be determined as the reference position of the X-ray detector 213. Alternatively, when the medical image obtaining apparatus 200 receives the user's input for designating the imaging start area and the imaging end area of the object, the location of the X-ray detector 213 for obtaining an image of the imaging start area may be determined as the reference position of the X-ray detector 213.

The medical image obtaining apparatus 200 may generate the virtual ruler by further considering other information together with the size of the X-ray detector 213.

For example, the medical image obtaining apparatus 200 may generate the virtual ruler by further considering at least one of a distance moved by the X-ray detector 213 from the first position to the second position, and a length of a section overlapped between the X-ray detector 213 located at the first position and the X-ray detector 213 located at the second position.

When the medical image obtaining apparatus 200 obtains the plurality of images of the plurality of portions of the object, the plurality of images may partially overlap one another. Accordingly, an overlapping section exists between the X-ray detector 213 at a location for first imaging and the X-ray detector 213 at a location for second imaging that is next after the first imaging. A length of the overlapping section between the X-ray detector 213 at the first location and the X-ray detector 213 at the second location may be predetermined as a default value or configured by a user's input.

Figure 27:
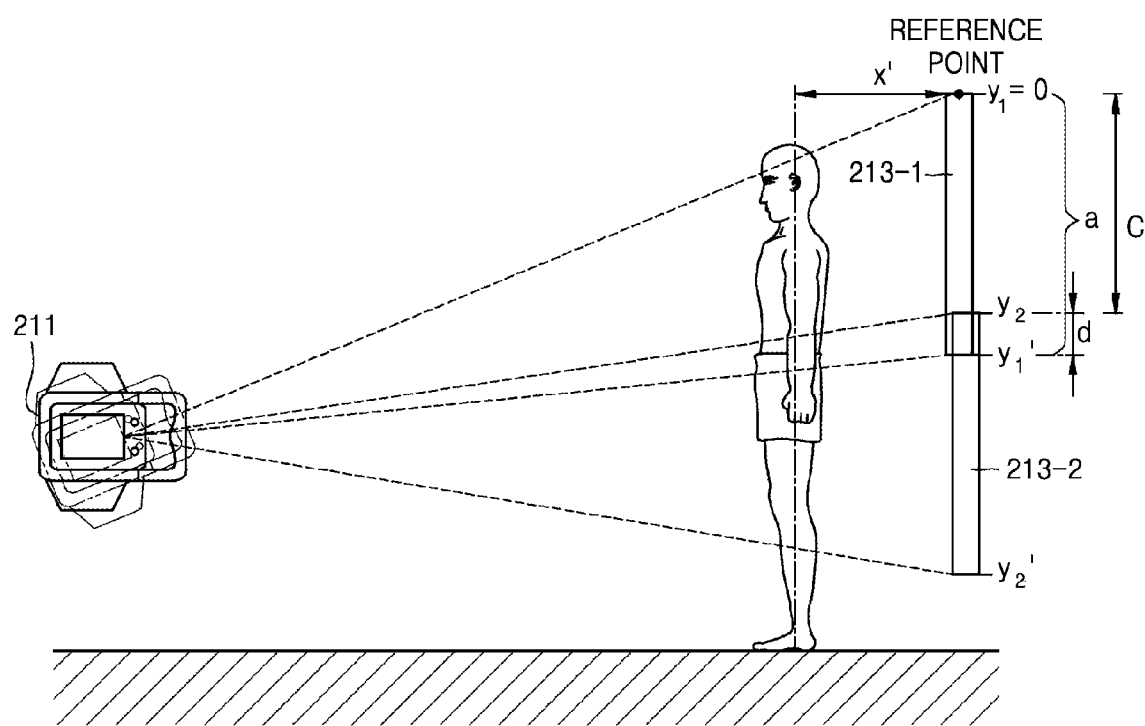
FIG. 27 is a diagram for describing a method of generating a virtual ruler based on a size of an X-ray detector, according to an exemplary embodiment.

FIG. 27 is a diagram for describing a method of generating a virtual ruler based on a size of the X-ray detector 213, according to an exemplary embodiment. FIG. 27 illustrates an example in which the medical image obtaining apparatus 200 obtains a first image of a first portion of an object and a second image of a second portion of the object.

As illustrated in FIG. 27, the medical image obtaining apparatus 200 may obtain the first image of the first portion of the object by using the X-ray emitter 211 and the X-ray detector 213, and then rotate the X-ray emitter 211 by a predetermined angle and move the X-ray detector at a first detector location 213-1 in a predetermined direction by a predetermined distance. Then, the medical image obtaining apparatus 200 may obtain the second image of the second portion of the object by using the X-ray emitter 211 and the X-ray detector at a second detector location 213-2.

FIG. 27 illustrates an example in which a first side of the X-ray detector 213 for obtaining the first image is determined as the reference point and a vertical distance of the X-ray detector 213 is a.

For example, when the distance moved by the X-ray detector 213 for obtaining the second image after obtaining the first image is c, a distance y1 from the reference point to a first side of the first image may be zero, and a distance y1' from the reference point to a second side of the first image may be a.

A distance y2 from the reference point to a first side of the second image may be obtained by using Equation 14 and a distance y2' from the reference point to a second side of the second image may be obtained by using Equation 15.

$$y2 = y1 + c = c \quad (14)$$

$$y2' = y1' + c = a + c \quad (15)$$

According to another example, when a length of the overlapping section between the X-ray detector 213-1 located at the first location and the X-ray detector 213-1 located at the second location is d, the distance y1 from the reference point to the first side of the first image may be zero, and the distance y1' from the reference point to the second side of the first image may be a.

A distance y2 from the reference point to a first side of the second image may be obtained by using Equation 16 and a distance y2' from the reference point to a second side of the second image may be obtained by using Equation 17.

$$y2 = a - d \quad (16)$$

$$y2' = y2 + a = (a-d) + a = 2 \times a - d \quad (17)$$

FIG. 27 illustrates an example in which the first side of the X-ray detector at a location 213-1 for obtaining the first image is determined as the reference point. However, exemplary embodiments are not limited to the example of FIG. 27. For example, when a plurality of images of a plurality of portions of the object are obtained, the medical image obtaining apparatus 200 may determine the first side of the X-ray detector 213 at the location for obtaining the first image as the reference point. The reference point may be predetermined as a default value or set by a user. The medical image obtaining apparatus 200 may obtain the reference point by measuring a distance from the reference point to the first side of the first image or obtain the reference point based on a user's input.

As illustrated in FIG. 27, when the object is imaged, the object may be located apart from the X-ray detector 213 by a predetermined distance. Thus, when a distance from the reference point to the first side of the X-ray detector 213 and a distance from the reference point to a second side of the X-ray detector 213 are obtained as information about a location of the image, the user may inaccurately measure an actual length of an object or an organ, etc., included in the object.

In this case, the medical image obtaining apparatus 200 may generate a first virtual ruler and a second virtual ruler indicating the information about a location of an object by further using a distance x' from the object to the X-ray detector 213. To generate the virtual ruler by further considering the distance from the object to the X-ray detector 213, the method described by referring to FIG. 5 may be used. Repeated descriptions will be omitted.

The medical image obtaining apparatus 200 may obtain the information about the distance from the reference point to the first side of the image and the distance from the reference point to the second side of the image, according to the described method. The medical image obtaining apparatus 200 may generate the virtual ruler indicating the distance from the reference point to the first side of the image and the distance from the reference point to the second side of the image.

The medical image obtaining apparatus 200 may generate the virtual ruler indicating values between the distance from the reference point to the first side of the image and the distance from the reference point to the second side of the image. The medical image obtaining apparatus 200 may generate the virtual ruler including gradations which indicate the values between the distance from the reference point to the first side of the image and the distance from the reference point to the second side of the image as predetermined gaps. For example, the first virtual ruler may include gradations indicating the values between the distance from the reference point to the first side of the first image and the distance from the reference point to the second side of the image as predetermined gaps.

For example, the medical image obtaining apparatus 200 may obtain an actual distance of each pixel on the image by using the number of pixels in a predetermined direction of the image. The medical image obtaining apparatus 200 may obtain the actual distance of each pixel by dividing the distance values between the distance from the reference point to the first side of the image and the distance from the reference point to the second side of the image, by the number of pixels.

The medical image obtaining apparatus 200 may generate the virtual ruler which indicates the distance values between the distance from the reference point to the first side of the image and the distance from the reference point to the second side of the image by using the distance from the reference point to the first side of the image and the actual distance of each pixel.

According to another example, the medical image obtaining apparatus 200 may divide the image into a plurality of portions in a predetermined direction and obtain actual distances of the portions of the image by using the number of the plurality of portions. The medical image obtaining apparatus 200 may obtain the actual distances of the portions of the image by dividing the distance values between the distance from the reference point to the first side of the image and the distance from the reference point to the second side of the image by the number of the plurality of portions.

The medical image obtaining apparatus 200 may generate the virtual ruler on which a distance value corresponding to a point at which the plurality of portions are divided is displayed on the point at which the plurality of portions are divided by using the distance from the reference point to the first side of the image and the actual distances of the portions.

The medical image obtaining apparatus 200 may change the reference point which is a reference for generating the virtual ruler, based on a user's input. The medical image obtaining apparatus 200 may receive the user's input for changing the reference point. The medical image obtaining apparatus 200 may generate the virtual ruler indicating information about a distance from the reference point changed based on the user's input to the image.

For example, the medical image obtaining apparatus 200 may generate a first virtual ruler indicating information about a distance from the reference point changed based on the user's input to the first image and a second virtual ruler indicating information about a distance from the changed reference point to the second image.

The medical image obtaining apparatus 200 may display the first virtual ruler on the first image and the second virtual ruler on the second image, in operation S2640.

Detailed exemplary embodiments with respect to the display of the virtual ruler on the image may correspond to the exemplary embodiments described by referring to FIGS. 9 through 12B. Repeated descriptions will be omitted.

According to exemplary embodiments, the virtual ruler is not imaged together with the object, and thus, the virtual ruler may be easily deleted from the image and easily edited separately from the image.

The medical image obtaining apparatus 200 may display the image without at least one virtual ruler, change a location of the virtual ruler of at least one image, or change gaps of gradations included in at least one virtual ruler based on the user's input. For example, the medical image obtaining apparatus 200 may display only the first image without the first virtual ruler, change a location of the first virtual ruler on the first image, or display the image by changing gaps of gradations included in the first virtual ruler based on a user's input. Alternatively, the medical image obtaining apparatus 200 may adjust a transparency of the virtual ruler based on a user's input.

Also, the medical image obtaining apparatus 200 may change a reference point, which is a reference for generating the virtual ruler, based on a user's input. The medical image obtaining apparatus 200 may receive the user's input for changing the reference point. The medical image obtaining apparatus 200 may renew and display the virtual ruler such that the virtual ruler indicates information about a distance from the reference point changed based on the user's input to the image.

The medical image obtaining apparatus 200 may generate a composite image by combining the obtained plurality of images.

Figure 28:
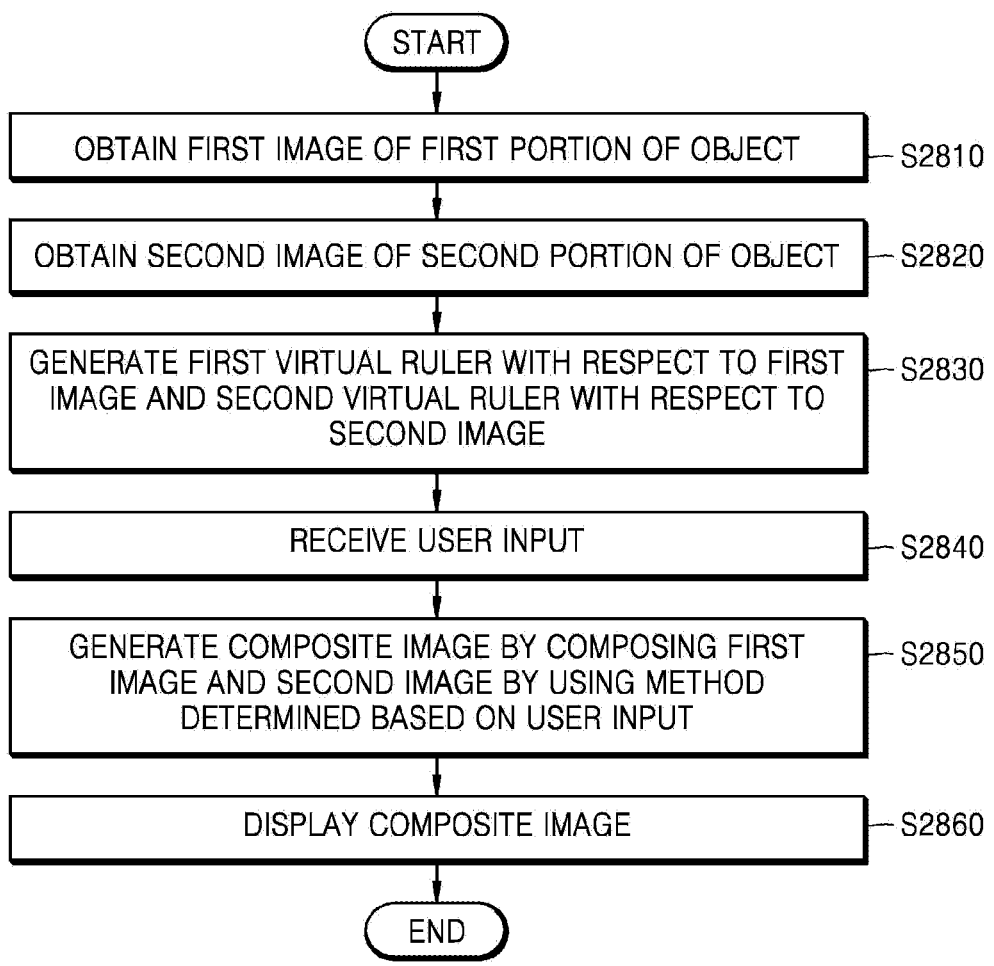
FIG. 28 is a flowchart of a method of generating a composite image by combining images by using a method determined based on a user's input and displaying the composite image, according to an exemplary embodiment.

FIG. 28 is a flowchart of a method of generating and displaying the composite image by combining images by using a method determined based on a user's input, according to an exemplary embodiment.

In operation S2810, the medical image obtaining apparatus 200 may irradiate X-rays towards an object by using the X-ray emitter 211 and detect the X-rays that penetrate the object by using the X-ray detector 213 located at a first location, to obtain a first image of a first portion of the object based on the detected X-rays.

In operation S2820, the medical image obtaining apparatus 200 may obtain a second image of a second portion of the object.

The medical image obtaining apparatus 200 may rotate the X-ray emitter 211 by a predetermined angle to change a direction of the X-rays such that the X-rays are emitted to the second portion of the object, or may move the X-ray emitter 211 in a predetermined direction by a predetermined distance to change a location of the X-rays such that the X-rays are emitted to the second portion of the object. The angle by which the X-ray emitter 211 is rotated or the distance by which the X-ray emitter 211 is moved for next imaging may be predetermined as default values or configured by a user.

The medical image obtaining apparatus 200 may move the X-ray detector 213 from the first location to a second location in a predetermined direction so that the X-rays penetrating the second portion of the object are detected. Then, the medical image obtaining apparatus 200 may irradiate the X-rays toward the object by using the X-ray emitter 211 and detect the X-rays that penetrate the object by using the X-ray detector 213 located at the second location, to obtain the second image of the second portion of the object based on detected X-rays. The distance by which the X-ray detector 213 is moved for next imaging may be predetermined as a default value or configured by a user.

The medical image obtaining apparatus 200 may generate a first virtual ruler and a second virtual ruler in operation S2830. The first virtual ruler may indicate information about a distance from a reference point to a first side of the first image and a distance from the reference point to a second side of the first image, and the second virtual ruler may indicate information about a distance from the reference point to a first side of the second image and a distance from the reference point to a second side of the second image.

The medical image obtaining apparatus 200 may generate the virtual ruler based on at least one of the rotation angle of the X-ray emitter 211, the moved distance of the X-ray emitter 211, the location information of the X-ray detector 213, the moved distance of the X-ray detector 213, and a size of the X-ray detector 213. Detailed exemplary embodiments with respect to the method of generating the virtual ruler may correspond to the descriptions with respect to FIGS. 13 thorough 15, FIG. 21, FIG. 24, and FIG. 26. Repeated descriptions will be omitted.

The medical image obtaining apparatus 200 may receive a user's input in operation S2840.

The user's input may include an input for the medical image obtaining apparatus 200 to perform an auto stitching function to automatically combine a plurality of images.

The user's input may include an input for selecting a method of generating a composite image by combining a first image and a second image.

For example, the user's input may include an input for selecting one of a first method and a second method.

The first method may be a method of generating the composite image by combining a first image and a second image based on the first virtual ruler and the second virtual ruler. According to the first method, the medical image obtaining apparatus 200 may overlap points having the same value on the first virtual ruler displayed on the first image and the second virtual ruler displayed on the second image to combine the first image and the second image.

The second method may be a method of generating the composite image by combining the first image and the second image based on a result of analyzing an area of the first image that overlaps the second image and an area of the second image that overlaps with the first image. According to the second image, the medical image obtaining apparatus 200 may compare the first image and the second image and may overlap the overlapped areas based on the result of the analysis, to combine the first image and the second image.

In operation S2850, the medical image obtaining apparatus 200 may generate the composite image by combining the first image and the second image by a method determined based on the user's input.

A time difference occurs between a point when the medical image obtaining apparatus 200 obtains the first image and a point when the medical image obtaining apparatus 200 obtains the second image. When a user moves during this time difference, a location of the user may differ between the point when the first image is obtained and the point when the second image is obtained. Thus, when the medical image obtaining apparatus 200 generates the composite image based on the virtual ruler only, according to the first method, the first image and the second image may be combined non-smoothly.

On the contrary, when the medical image obtaining apparatus 200 generates the composite image by using the second method, a time for analyzing and comparing the images via the medical image obtaining apparatus 200 additionally occurs. Accordingly, the first method is quicker than the second method, and the second method is more suitable for more accurate image composition than the first method.

If the user's input received in operation S2840 is the input for selecting the first method, the medical image obtaining apparatus 200 may compose the first image and the second image by overlapping the points having the same value on the first virtual ruler displayed on the first image and the second virtual ruler displayed on the second image.

If the user's input received in operation S2840 is the input for selecting the second method, the medical image obtaining apparatus 200 may compose the first image and the second image by comparing the first image and the second image and combining the overlapped areas based on the analysis.

The medical image obtaining apparatus 200 may calculate a similarity between at least an area of the first image and at least an area of the second image by comparing the first image and the second image. The medical image obtaining apparatus 200 may determine a matching area between the first image and the second image by comparing the calculated similarity and a threshold value. The medical image obtaining apparatus 200 may combine the first image and the second image by overlapping the matching areas according to the second method.

When combining the first image and the second image according to the second method, the medical image obtaining apparatus 200 may use the first virtual ruler and the second virtual ruler. The medical image obtaining apparatus 200 may compare only areas around the points having the same value on the first virtual ruler and the second virtual ruler so as to reduce the computational load and increase a processing speed, compared with the case when all areas of the first image and the second image are compared.

The medical image obtaining apparatus 200 may quickly or accurately generate the composite image by combining the first image and the second image by using the method determined based on the user's input.

The medical image obtaining apparatus 200 may display the composite image in operation S2860.

The medical image obtaining apparatus 200 may display on the composite image virtual rulers corresponding to a plurality of images forming the composite image. Detailed exemplary embodiments with respect to the display of the virtual ruler on the image may correspond to the descriptions with reference to FIGS. 9 through 12B. Repeated descriptions will be omitted.

According to exemplary embodiments, the virtual ruler is not imaged together with the object, and thus, the virtual ruler may be easily deleted from the image and easily edited separately from the image.

For example, the medical image obtaining apparatus 200 may display only the composite image without the virtual ruler, change a location of the virtual ruler on the composite image, or display the image by changing gaps of gradations included in the virtual ruler, based on a user's input. Alternatively, the medical image obtaining apparatus 200 may adjust a transparency of the virtual ruler based on a user's input.

Also, the medical image obtaining apparatus 200 may change a reference point, which is a reference for generating the virtual ruler, based on a user's input. The medical image obtaining apparatus 200 may receive the user's input changing the reference point. The medical image obtaining apparatus 200 may renew and display the virtual ruler such that the virtual ruler indicates information about a distance from the reference point changed based on the user's input to the image.

Information about a distance from the reference point to the composite image may include information about a distance from the reference point to a portion of an object displayed on the composite image. The information about a distance from the reference point to the composite image may include information about a distance from the reference point to a first side of the composite image and a distance from the reference point to a second side of the composite image.

Figure 29:
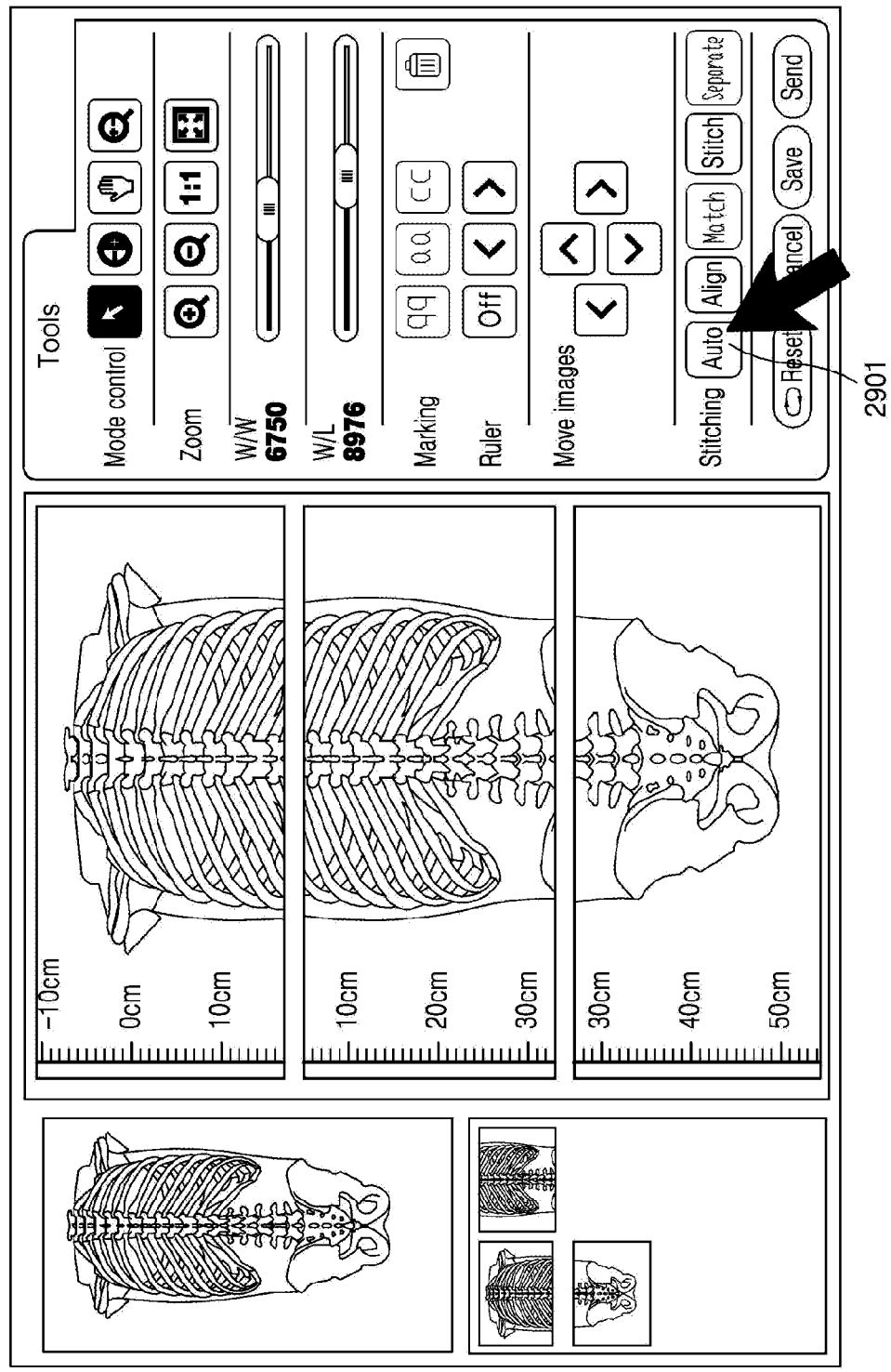

FIGS. 29, 30, and 31 illustrate an example of a screen displayed for generating a composite image, according to an exemplary embodiment.

As illustrated in FIG. 29, the medical image obtaining apparatus 200 may display a plurality of images of a plurality of portions of an object, the virtual ruler being displayed on each of the plurality images.

The virtual ruler generated by the medical image obtaining apparatus 200 is not based on the lead ruler imaged together with the object, and thus, the virtual ruler may be easily deleted from the image and easily edited separately from the image. The medical image obtaining apparatus 200 may change the reference point, which is a reference for generating the virtual ruler, based on a user's input.

The medical image obtaining apparatus 200 may renew and display the virtual ruler based on the user's input changing the reference point. FIG. 29 illustrates an example of a screen on which the virtual ruler is renewed based on a changed reference point when a location of the reference point is moved by 10 cm in a vertical direction, compared with the location of the reference point of FIG. 6.

The user may manually combine a plurality of images by referring to a distance values displayed on gradations of the virtual ruler displayed on each of the plurality of images.

The medical image obtaining apparatus 200 may perform an auto stitching function to automatically combine the plurality of images based on a user's input for selecting an icon 2901 for performing the auto stitching function.

When the medical image obtaining apparatus 200 receives the user's input to perform the auto stitching function, the medical image obtaining apparatus 200 may provide a GUI for receiving the user's input for selecting the method of generating the composite image by combining the plurality of images.

For example, as illustrated in FIG. 30, the medical image obtaining apparatus 200 may provide a GUI 3010 including an icon 3011 for selecting the first method, which is the quick method of composing images by using the virtual ruler, an icon 3013 for selecting the second method, which is the accurate method of composing images based on an analysis of images, and an icon 3015 for cancelling the execution of the auto stitching function.

Alternatively, as illustrated in FIG. 31, the medical image obtaining apparatus 200 may provide a GUI 3110 including an icon 3111 for selecting the first method, which is the quick method of composing images by using the virtual ruler, an icon 3113 for selecting the second method, which is the accurate method of composing images based on an analysis of images, and an icon 3115 for cancelling the execution of the auto stitching function.

The medical image obtaining apparatus 200 may compose the plurality of images by the method determined based on the user's input, thereby quickly or accurately generating the composite image according to a user's preference.

The exemplary embodiments described above may be written as computer programs and may be implemented in general-use digital computers that execute the computer programs using a computer-readable recording medium.

Examples of the computer-readable recording medium include magnetic storage media (e.g., ROM, floppy disks, hard disks, etc.) and optical recording media (e.g., CD-ROMs, and/or DVDs).

The foregoing exemplary embodiments and advantages are merely exemplary and are not to be construed as limiting the present teaching. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. A medical image obtaining apparatus comprising:
   an X-ray emitter configured to emit X-rays towards an object;
   an X-ray detector configured to detect X-rays that have been emitted to obtain an image of a portion of the object;
   a processor configured to generate a virtual ruler which indicates information about a location of the image with respect to a reference point, based on a rotation angle of the X-ray emitter; and
   a display configured to display the virtual ruler on the image,
   wherein the virtual ruler indicates information about a distance from the reference point to a first side of the image and a distance from the reference point to a second side of the image, in a longitudinal direction of the X-ray detector.

2. The medical image obtaining apparatus of claim 1, wherein the processor is configured to rotate the X-ray emitter is rotated so that a direction of the X-rays emitted to the object is changed to obtain the image of the portion of the object, and move the X-ray detector in a linear direction based on a rotation direction of the X-ray emitter.

3. The medical image obtaining apparatus of claim 1, wherein the X-rays emitted by the X-ray emitter pass through a collimator, and
   the processor is configured to generate the virtual ruler based on an opening size of the collimator, a distance from an X-ray tube of the X-ray emitter to the collimator, and a distance from the X-ray tube to the X-ray detector.

4. The medical image obtaining apparatus of claim 1, wherein the processor is configured to generate the virtual ruler based on a size of the X-ray detector and a distance from the X-ray emitter to the X-ray detector.

5. The medical image obtaining apparatus of claim 1, wherein the reference point corresponds to a first side of the X-ray detector when the X-ray detector is located at a reference position, with respect to a floor level or a ceiling level.

6. The medical image obtaining apparatus of claim 1, wherein the virtual ruler comprises gradations which indicate values between the distance from the reference point to the first side of the image and the distance from the reference point to the second side of the image as predetermined gaps.

7. The medical image obtaining apparatus of claim 1, wherein the virtual ruler is one of a plurality of virtual rulers and the image is one of a plurality of images,
   the processor is configured to rotate the X-ray emitter so that a direction of the X-rays emitted towards the object is changed, move the X-ray detector in a linear direction according to a rotation direction of the X-ray emitter in order to divide the object into portions in a predetermined direction, and obtain the plurality of images corresponding to the portions, and
   the processor is configured to generate the plurality of virtual rulers which indicate information about a location of each of the plurality of images, based on the rotation angle of the X-ray emitter to obtain each of the plurality of images.

8. The medical image obtaining apparatus of claim 7, wherein each of the plurality of virtual rulers indicates information about the distance from the reference point to the first side of a respective image, of the plurality of images, and the distance from the reference point to the second side of the respective image, and
   the processor is further configured to determine the first side of the image which is a first-ordered image obtained from the plurality of images, as the reference point.

9. The medical image obtaining apparatus of claim 1, further comprising a user input unit configured to receive a user's input for changing the reference point, and
   the processor is configured to generate the virtual ruler which indicates information about a distance from the reference point that is changed based on the user's input to the image.

10. The medical image obtaining apparatus of claim 1, wherein the processor is configured to generate the virtual ruler based on a distance from the object to the X-ray detector.

11. The medical image obtaining apparatus of claim 1, further comprising a user input unit configured to receive a user's input, and
    the processor is configured to control the display based on the user's input such that only the image without the virtual ruler is displayed, a location of the virtual ruler on the image is changed, or gaps of gradations included in the virtual ruler are changed.

12. A method of displaying a medical image, the method comprising:
    obtaining an image of a portion of an object, by radiating X-rays by an X-ray emitter and detecting the X-rays that have penetrated the object by an X-ray detector;
    generating a virtual ruler which indicates information about a location of the image with respect to a reference point, based on a rotation angle of the X-ray emitter; and
    displaying the virtual ruler on the image, wherein the virtual ruler indicates information about a distance from the reference point to a first side of the image and a distance from the reference point to a second side of the image, in a longitudinal direction of the X-ray detector.

13. A medical image obtaining apparatus comprising:
an X-ray emitter configured to emit X-rays towards an object;
an X-ray detector configured to detect X-rays that have been emitted to obtain an image of a portion of the object;
a processor configured to generate a virtual ruler which indicates information about a location of the image with respect to a reference point based on a moved distance of the X-ray emitter; and
a display configured to display the virtual ruler on the image,
wherein the virtual ruler indicates information about a distance from the reference point to a first side of the image and a distance from the reference point to a second side of the image, in a longitudinal direction of the X-ray detector.

14. A medical image obtaining apparatus comprising:
an X-ray emitter configured to emit X-rays towards an object;
an X-ray detector configured to detect X-rays that have been emitted to obtain a first image of a first portion of the object when the X-ray detector is located at a first position and to obtain a second image of a second portion of the object when the X-ray detector is moved from the first position to a second position;
a processor configured to generate a first virtual ruler indicating information about a location of the first image with respect to a reference point and a second virtual ruler indicating information about a location of the second image with respect to the reference point, based on a size of the X-ray detector; and
a display configured to display the first virtual ruler on the first image and the second virtual ruler on the second image,
wherein the first virtual ruler indicates information about a distance from the reference point to a first side of the first image and a distance from the reference point to a second side of the first image, in a longitudinal direction of the X-ray detector.

15. The medical image obtaining apparatus of claim 14, wherein the processor is configured to generate the second virtual ruler based on at least one among a distance by which the X-ray detector is moved from the first position to the second position and a length of a section by which the X-ray detector located at the first position is overlapped with the X-ray detector located at the second position.

16. The medical image obtaining apparatus of claim 14, wherein
the second virtual ruler indicates information about a distance from the reference point to a first side of the second image and a distance from the reference point to the second side of the second image, in the longitudinal direction of the X-ray detector.

17. The medical image obtaining apparatus of claim 14, wherein the reference point corresponds to a first side of the X-ray detector when the X-ray detector is located at a reference position, with respect to a floor level or a ceiling level.

18. The medical image obtaining apparatus of claim 16, wherein at least one among the first virtual ruler and the second virtual ruler comprises gradations which indicate values between the distance from the reference point to the first side of the at least one among the first image and the second image and the distance from the reference point to the second side of the at least one among the first image and the second image as predetermined gaps.

19. The medical image obtaining apparatus of claim 14, wherein the processor is configured to detect the first side of the first image obtained when the X-ray detector is located at the first position as the reference point.

20. The medical image obtaining apparatus of claim 16, further comprising a user input unit configured to receive a user's input for changing the reference point, and
the processor is configured to generate the first virtual ruler indicating information about a distance from the reference point changed based on the user's input to the first image, and the second virtual ruler indicating information about a distance from the changed reference point to the second image.

21. The medical image obtaining apparatus of claim 14, wherein the processor is configured to generate the first virtual ruler and the second virtual ruler based on a distance from the object to the X-ray detector.

22. The medical image obtaining apparatus of claim 14, further comprising a user input unit configured to receive a user's input, and
the processor is configured to control the display based on the user's input such that only the first image without the first virtual ruler is displayed, only the second image without the second virtual ruler is displayed, a location of the first virtual ruler on the first image or a location of the second virtual ruler on the second image is changed, or gaps of gradations included in the first virtual ruler or in the second virtual ruler are changed.

23. A method of displaying a medical image, the method comprising:
obtaining a first image of a first portion of an object based on detected X-rays, by radiating X-rays towards the object by an X-ray emitter and detecting the X-rays that have penetrated the object by an X-ray detector located at a first position;
obtaining a second image of a second portion of the object based on detected X-rays, by radiating X-rays towards the object and detecting the X-rays that have penetrated the object by the X-ray detector which is moved from the first position to a second position;
generating a first virtual ruler indicating information about a location of the first image with respect to a reference point and a second virtual ruler indicating information about a location of the second image with respect to the reference point based on a size of the X-ray detector; and
displaying the first virtual ruler on the first image and the second virtual ruler on the second image,
wherein the first virtual ruler indicates information about a distance from the reference point to a first side of the first image and a distance from the reference point to a second side of the first image, in a longitudinal direction of the X-ray detector.

24. A medical image obtaining apparatus comprising:
an X-ray emitter configured to emit X-rays towards an object;
an X-ray detector configured to detect X-rays that have been emitted to obtain a first image of a first portion of the object when the X-ray detector is located at a first position and a second image of a second portion of the object when the X-ray detector is moved from the first position to a second position;

a user input unit configured to receive a user's input;

a processor configured to generate a first virtual ruler indicating information about a distance from a reference point to a first side of the first image and a distance from the reference point to a second side of the first image and a second virtual ruler indicating information about a distance from the reference point to a first side of the second image and a distance from the reference point to a second side of the second image, and generate a composite image by combining the first image and the second image in response to the user's input; and a display configured to display the composite image.

25. The medical image obtaining apparatus of claim 24, wherein the user's input is for selection of one among a first method and a second method, the first method is a method for generating the composite image is by combining the first image and the second image based on the first virtual ruler and the second virtual ruler, and the second method is a method for generating the composite image is by combining the first image and the second image based on a result of analyzing a portion of the first image that overlaps the second image and a portion of the second image that overlaps the first image.

26. The medical image obtaining apparatus of claim 25, wherein the processor is configured to generate the first image and the second image by overlapping points having a same value on the first virtual ruler and the second virtual ruler in response to the user's input selecting the first method.

27. A method of displaying a medical image, the method comprising:

obtaining a first image of a first portion of an object based on detected X-rays, by radiating X-rays towards the object and detecting the X-rays that have penetrated the object by an X-ray detector located at a first position;

obtaining a second image of a second portion of the object based on detected X-rays, by radiating X-rays towards the object and detecting the X-rays that have penetrated the object by the X-ray detector that is moved from the first position to a second position;

generating a first virtual ruler indicating information about a distance from a reference point to a first side of the first image and a distance from the reference point to a second side of the first image and a second virtual ruler indicating information about a distance from the reference point to a first side of the second image and a distance from the reference point to a second side of the second image;

receiving a user's input;

generating a composite image by combining the first image and the second image by using a method determined based on the user's input; and displaying the composite image.

28. The medical image obtaining apparatus of claim 1, wherein the processor is configured to control the display to display numerical values on the virtual ruler that indicate corresponding distances of features in the image from the reference point.

29. The medical image obtaining apparatus of claim 24, wherein, when a user input for moving the first image of the composite image along a first direction is received, the processor moves the first image along the first direction without moving the first virtual ruler.

30. The medical image obtaining apparatus of claim 24, wherein, when a user input for moving the first image of the composite image along a second direction is received, the processor moves the first image along the second direction with moving the first virtual ruler along the second direction.

31. The medical image obtaining apparatus of claim 24, wherein, when a user input for moving the first image of the composite image along a first direction is received, the processor moves the first image along the first direction with simultaneously moving the first virtual ruler and the second virtual ruler along the first direction.

* * * * *